US008217223B2

(12) United States Patent
Haertel et al.

(10) Patent No.: US 8,217,223 B2
(45) Date of Patent: Jul. 10, 2012

(54) NUCLEIC ACID MOLECULES ENCODING *WRINKLED1*-LIKE POLYPEPTIDES AND METHODS OF USE IN PLANTS

(75) Inventors: Heiko A. Haertel, Berlin (DE); Garima Bhatt, Durham, NC (US); Volker Mittendorf, Hillsborough, NC (US); Karin J. Shank, Raleigh, NC (US)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 12/953,965

(22) Filed: Nov. 24, 2010

(65) Prior Publication Data
US 2011/0162103 A1 Jun. 30, 2011

Related U.S. Application Data

(62) Division of application No. 11/629,727, filed as application No. PCT/US2005/021500 on Jun. 16, 2005, now abandoned.

(60) Provisional application No. 60/580,334, filed on Jun. 16, 2004, provisional application No. 60/600,466, filed on Aug. 11, 2004.

(51) Int. Cl.
*A01H 1/00* (2006.01)
*A01H 5/00* (2006.01)
*A01H 5/10* (2006.01)
*C12N 5/14* (2006.01)

(52) U.S. Cl. ........ 800/278; 800/290; 800/295; 800/298; 435/410; 435/419; 536/23.6

(58) Field of Classification Search .................. None
See application file for complete search history.

(56) References Cited

U.S. PATENT DOCUMENTS

| | | | |
|---|---|---|---|
| 5,169,770 | A | 12/1992 | Chee et al. |
| 5,322,783 | A | 6/1994 | Tomes et al. |
| 5,376,543 | A | 12/1994 | Chee et al. |
| 5,955,650 | A | 9/1999 | Hitz |
| 6,084,164 | A | 7/2000 | Bidney et al. |
| 7,135,616 | B2 | 11/2006 | Heard et al. |
| 2004/0045049 | A1 | 3/2004 | Zhang et al. |
| 2004/0123343 | A1* | 6/2004 | La Rosa et al. ............. 800/278 |

FOREIGN PATENT DOCUMENTS

| | | |
|---|---|---|
| EP | 0 397 687 B1 | 12/1988 |
| EP | 0 424 047 A1 | 4/1991 |
| WO | WO-89/05859 A1 | 6/1989 |
| WO | WO-02/059332 A2 | 8/2002 |
| WO | WO-02/072775 A2 | 9/2002 |
| WO | WO-03/002751 A2 | 1/2003 |
| WO | WO-2004/035798 A2 | 4/2004 |

OTHER PUBLICATIONS

Dietz et al, Protoplasma, 2010, vol. 245, pp. 3-14.*
Riechmann and Meyerowitz, Biol. Chem., vol. 379, pp. 633-646, Jun. 1998.*
Cernac and Benning, The Plant Journal, Nov. 2004, vol. 40, pp. 575-585.*
BLAST results—Aug. 16, 2011.*
Topfer, R., et al., "Modification of Plant Lipid Synthesis", Science, vol. 268, (1995), pp. 681-686.
Cahoon, E.B., et al., "Expression of a Coriander Desaturase Results in Petroselinic Acid Production in Transgenic Tobacco", PNAS, vol. 89, (1992), pp. 11184-11188.
Van De Loo, F.J., et al., "Chapter 3. Unusual Fatty Acids", Chapter 3 in "Lipid Metabolism in Plants", CRC Press, Inc., 1993, pp. 91-126.
Ohlrogge, J., et al., "Lipid Biosynthesis", The Plant Cell, vol. 7, (1995), pp. 957-970.
Shanklin, J. et al., "Desaturation and Related Modifications of Fatty Acids", Annu. Rev. Plant Physiol. Plant Mol. Biol., vol. 49, (1998), pp. 611-641.
Frentzen, M., "Acyltransferases from Basic Science to Modified Seed Oils", Lipid, vol. 100, Issues 4-5, (1998), pp. 161-166.
Van De Loo, F.J., et al., "An Oleate 12-Hydroxylase from *Ricinus communis* L. is a Fatty Acyl Desaturase Homolog", PNAS, vol. 92, (1995), pp. 6743-6747.
Brenner, R.R., "Regulatory Function of delta6 Desaturase—Key Enzyme of Polyunsaturated Fatty Acid Synthesis", Adv. Exp. Med. Biol., vol. 83, (1977), pp. 85-101.
Focks, N., et al., "*wrinkled1*: A Novel, Low-Seed-Oil Mutant of *Arabidopsis* with a Deficiency in the Seed-Specific Regulation of Carbohydrate Metabolism", Plant Physiol., vol. 118, (1998), pp. 91-101.
The *Arabidopsis* Genome Initiative, "Analysis of the Genome Sequence of the Flowering Plant *Arabidopsis thaliana*", Nature, vol. 408, (2000), pp. 796-815.
Tatusov, R.L., et al., "A Genomic Perspective on Protein Families", Science, vol. 278, (1997), pp. 631-637.
Meinkoth, J., et al., "Hybridization of Nucleic Acids Immobilized on Solid Supports", Analytical Biochemistry, vol. 138, (1984), pp. 267-284.
Kuninaka, A., "Nucleotides and Related Compounds", Chapter 15 in "Biotechnology, A Multi-Volume Comprehensive Treatise", Rehm, H.-J., et al., eds., 2nd Rev. Ed., Wiley-VCH, 2001, vol. 6, pp. 561-612.
Gruber, M.Y., et al., "Vectors for Plant Transformation", Chapter 7 in "Methods in Plant Molecular Biology and Biotechnology", Glick, B.R., et al., eds., CRC Press, 1993, pp. 89-108.
Jenes, B., et al., "Techniques for Gene Transfer", Chapter 4 in "Transgenic Plants, vol. 1, Engineering and Utilization", Kung, S.-D, et al., eds., Academic Press, Inc., 1993, pp. 125-146.
Potrykus, I., "Gene Transfer to Plants: Assessment of Published Approaches and Results", Annu. Rev. Plant Physiol. Plant Mol. Biol. vol. 42, (1991), pp. 205-225.

(Continued)

*Primary Examiner* — Eileen B O Hara

(74) *Attorney, Agent, or Firm* — Connolly Bove Lodge & Hutz LLP

(57) ABSTRACT

Isolated nucleic acids and proteins associated with lipid and sugar metabolism regulation are provided. In particular, lipid metabolism proteins (LMP) and encoding nucleic acids originating from *Arabidopsis thaliana, Brassica napus, Glycine max, Oryza sativa*, and *Triticum aestivum* are provided. The nucleic acids and proteins are used in methods of producing transgenic plants and modulating levels of seed storage compounds. Preferably, the seed storage compounds are lipids, fatty acids, starches, or seed storage proteins. The nucleic acids and proteins also are used in methods of modulating the seed size, seed number, seed weight, root length, and leaf size of plants.

17 Claims, 8 Drawing Sheets

OTHER PUBLICATIONS

Miki, B.L., et al., "Procedures for Introducing Foreign DNA into Plants", Chapter 6 in "Methods in Plant Molecular Biology and Biotechnology", Glick, B.R., et al., eds., CRC Press, 1993, pp. 67-88.

Horsch, R.B., et al., "A Simple and General Method for Transferring Genes into Plants", Science, vol. 227, (1985), pp. 1229-1231.

Malone-Schoneberg, J., et al., "Stable Transformation of Sunflower Using Agrobacterium and Split Embryonic Axis Explants", Plant Science, vol. 103, (1994), pp. 199-207.

Meyer, K., "A Protein Phosphatase 2C Involved in ABA Signal Transduction in *Arabidopsis thaliana*", Science, vol. 264, (1994), pp. 1452-1455.

Hofgen, R. et al., Biochemical and Genetic Analysis of Different Patatin Isoforms Expressed in Various Organs of Potato (*Solanum tuberosum*), Plant Science, vol. 66, (1990), pp. 221-230.

Kermode, A.R., "Mechanisms of Intracellular Protein Transport and Targeting in Plant Cells", Critical Rev. in Plant Sciences, vol. 15 No. 4 (1996), pp. 285-423.

Koncz, C., et al., "The Promoter of $T_L$-DNA Gene 5 Controls the Tissue-Specific Expression of Chimaeric Genes Carried by a Novel Type of Agrobacterium Binary Vector", Mol. Gen. Genet., vol. 204, (1986), pp. 383-396.

Bechtold, N., et al., "*In Planta Agrobacterium* Mediated Gene Transfer by Infiltration of Adult *Arabidopsis thaliana* Plants", Sciences de la Vie: Biologie et Génétique Moléculaire, 1993, vol. 316, pp. 1194-1199.

Bent, A.F., et al., "RPS2 of *Arabidopsis thaliana*: A Leucine-Rich Repeat Class of Plant Disease Resistance Genes", Science, vol. 265, (1994), pp. 1856-1860.

Moloney, M. M., et al., "High Efficiency Transformation of *Brassica napus* Using *Agrobacterium* Vectors", Plant Cell Reports, vol. 8, (1989), pp. 238-242.

De Block, M. et al., "Transformation of *Brassica napus* and *Brassica oleracea* Using *Agrobacterium tumefaciens* and the Expression of the *bar* and *neo* Genes in the Transgenic Plants", Plant Physiol., vol. 91, (1989), pp. 694-701.

Mlynarova, L., et al., "High Efficiency *Agrobacterium*-Mediated Gene Transfer to Flax", Plant Cell Reports, vol. 13, (1994), pp. 282-285.

Kolmar, H. et al., "Membrane Insertion of the Bacterial Signal Transduction Protein ToxR and Requirements of Transcription Activation Studied by Modular Replacement of Different Protein Substructures", The EMBO Journal, vol. 14 No. 16, (1995), pp. 3895-3904.

Gennis, R.B., "Characterization and Structural Principles of Membrane Proteins", Chapter 3 in "Biomembranes: Molecular Structure and Function", Springer-Verlag, 1988, pp. 85-137.

Fiehn, O., et al., "Metabolite Profiling for Plant Functional Genomics", Nature Biotechnology, vol. 18, (2000), pp. 1157-1161.

Christie, W.W., "Structural Analysis of Fatty Acids", Chapter 4 in "Advances in Lipid Methodology—Four", Christie, W.W., ed., Matreya, 1996, pp. 119-169.

Patek, M., et al., "Leucine Synthesis in *Corynebacterium glutamicum*: Enzyme Activities, Structure of *leuA*, and Effect of *leuA* Inactivation on Lysine Synthesis", Applied and Environ. Microbiol., vol. 60, No. 1, (1994), pp. 133-140.

Malakhova, I.I., et al., "Thin-layer Chromatography of Free Amino Acids. Selection of Conditions for the Separation of L-lysine, L-homoserine, and L-threonine", Russian Biotechnology, No. 11, (1996), pp. 26-31.

Schmidt, S., et al., "Near Infrared Spectroscopy in Fermentation and Quality Control for Amino Acid Production", Bioprocess Engineering, vol. 19, (1998), pp. 67-70.

Elvers, B., et al., eds., "7. Riboflavin" and "8. Vitamin $B_6$", in "Ullmann's Encyclopedia of Industrial Chemistry, vol. A27: Thorium and Thorium Compounds to Vitamins", 5th Rev. Ed., Wiley-VCH, 1985. pp. 521-540.

Elvers, B., et al., eds., "9. Vitamin $B_{12}$ (Cobalamins)", in "Ullmann's Encyclopedia of Industrial Chemistry, vol. A27: Thorium and Thorium Compounds to Vitamins", 5th Rev. Ed., Wiley-VCH, 1985. pp. 540-547.

Elvers, B., et al., eds., "11. Pantothenic Acid", in "Ullmann's Encyclopedia of Industrial Chemistry, vol. A27: Thorium and Thorium Compounds to Vitamins", 5th Rev. Ed., Wiley-VCH, 1985. pp. 559-566.

Elvers, B., et al., eds., "13. Folic Acid", in "Ullmann's Encyclopedia of Industrial Chemistry, vol. A27: Thorium and Thorium Compounds to Vitamins", 5th Rev. Ed., Wiley-VCH, 1985. pp. 575-581.

Elvers, B., et al., eds., "14, Niacin (Nicotinic Acid, Nicotinamide)", in "Ullmann's Encyclopedia of Industrial Chemistry, vol. A27: Thorium and Thorium Compounds to Vitamins", 5th Rev. Ed., Wiley-VCH, 1985. pp. 581-587.

Rupp, W.D., "DNA Repair Mechanisms", Chapter 121 in "*Escherichia coli* and *Salmonella*: Cellular and Molecular Biology", Neidhardt, F.C., et al., eds., 2nd Ed., vol. 2, ASM Press, 1996, pp. 2277-2294.

Greener, A., et al., "XL1-Red: A Highly Efficient Random Mutagenesis Strain", Strategies in Molecular Biology, 1994, vol. 7, pp. 32-34.

Schütte, H., et al., "Cell Disruption and Isolation of Non-Secreted Products", Chapter 19 on "Biotechnology, A Multi-Volume Comprehensive Treatise", Rehm, H.-J., et al., eds., 2nd Rev. Ed., Wiley-VCH, 2001, vol. 3, pp. 505-526.

Cleland, J.L., et al., "In Vitro Protein Refolding", Chapter 20 in "Biotechnology, A Multi-Volume Comprehensive Treatise", Rehm, H.-J., et al., eds., 2nd Rev. Ed., Wiley-VCH, 2001, vol. 3, pp. 527-555.

Schügerl, K., et al., "Liquid-Liquid Extraction (Small Molecules)", Chapter 21 in "Biotechnology, A Multi-Volume Comprehensive Treatise", Rehm, H.-J., et al., eds., 2nd Rev. Ed., Wiley-VCH, 2001, vol. 3, pp. 557-592.

Kelley, B.D., et al., "Protein Purification by Liquid-Liquid Extraction", Chapter 22 in "Biotechnology, A Multi-Volume Comprehensive Treatise", Rehm, H.-J., et al., eds., 2nd Rev. Ed., Wiley-VCH, 2001, vol. 3, pp. 593-616.

Janson, J.-C., et al., "Protein Separation and Purification", Chapter 23 in "Biotechnology, A Multi-Volume Comprehensive Treatise", Rehm, H.-J., et al., eds., 2nd Rev, Ed., Wiley-VCH, 2001, vol. 3, pp. 617-642.

Sundaram, S., et al., "Afinity Separations", Chapter 24 in "Biotechnology, A Multi-Volume Comprehensive Treatise", Rehm, H.-J., et al., eds., 2nd Rev. Ed., Wiley-VCH, 2001, vol. 3, pp. 643-677.

Grodzinsky, A.J., et al., "Electrokinetic Separations", Chapter 25 in "Biotechnology, A Multi-Volume Comprehensive Treatise", Rehm, H.-J., et al., eds., 2nd Rev. Ed., Wiley-VCH, 2001, vol. 3, pp. 679-693.

Gölker, C. F., et al., "Final Recovery Steps: Lyophilization, Spray-Drying", Chapter 26 in "Biotechnology, A Multi-Volume Comprehensive Treatise", Rehm, H.-J., et al., eds., 2nd Rev. Ed., Wiley-VCH, 2001, vol. 3, pp. 698-714.

Hills, M. J., "Control of Storage-Product Synthesis in Seeds", Current Opinion in Plant Biology, 2004, vol. 7, No. 3, pp. 302-308.

Ruuska, S. A., et al., "Contrapuntal Networks of Gene Expression during *Arabidopsis* Seed Filling", The Plant Cell, 2002, vol. 14, No. 6, pp. 1191-1206.

Supplemental European Search Report issued in European Patent Application No. 05763044, Dec. 22, 2009.

Gennis, R.B., "Membrane Enzymology", Chapter 6 in "Biomembranes: Molecular Structure and Function", Springer-Verlag, 1988, pp. 199-234.

Gennis, R.B., "Pores, Channels and Transporters", Chapter 8 in "Biomembranes: Molecular Structure and Function", Springer-Verlag, 1988, pp. 270-322.

Gerhartz, W., et al., eds., "5. Chemical Analysis", in "Ullmann's Encyclopedia of Industrial Chemistry, vol. A2: Amines, Aliphatic to Antibiotics", 5th Rev. Ed., Wiley-VCH, 1985. pp. 89-90.

Fallon, A., et al., "Nucleosides and Nucleotides", Chapter 11.1 in "Applications of HPLC in Biochemistry", Elsevier, 1987, pp. 144-168.

Datar, R.V., et al., "Cell and Cell Debris Removal: Centrifugation and Crossflow Filtration", Chapter 18 in "Biotechnology, A Multi-Volume Comprehensive Treatise", Rehm, H.J., et al., eds., 2nd Rev. Ed., Wiley-VCH, 2001, vol. 3, 2nd Ed., 469-503.

Cahoon, E.B., et al., "Biosynthetic Origin of Conjugated Double Bonds: Production of Fatty Acid Components of High-Value Drying Oils in Transgenic Soybean Embryos", Proc. Natl. Acad. Sci. USA, 1999, vol. 96, No. 22, pp. 12935-12940.
Browse, J., et al., "Fatty Acid Composition of Leaf Lipids Determinded after Combined Digestion and Fatty Acid Methyl Ester Formation from Fresh Tissue", Analytical Biochemistry, vol. 152, (1986), pp. 141-145.
Stitt, M., et al., "Metabolite Levels in Specific Cells and Subcellular Compartments of Plant Leaves", Methods in Enzymology, 1989, vol. 174, pp. 518-552.
Hartel, H., et al., "Photosynthetic Light Utilization and Xanthophyll Cycle Activity in the Galactolipid Deficient *dgd1* Mutant of *Arabidopsis thaliana*", Plant Physiol. Biochem., vol. 36, No. 6, (1998), pp. 407-417.
Bradford, M. M., "A Rapid and Sensitive Method for the Quantitation of Microgram Quantities of Protein Utilizing the Principle of Protein-Dye Binding", Analytical Biochemistry, vol. 72, (1976), pp. 248-254.

Renz, A., et al., "Partial Purification from Potato Tubers of Three Fructokinases and Three Hexokinases Which Show Differing Organ and Developmental Specificity", Planta, vol. 190, (1993), pp. 156-165.
Burrell, M. M., et al., "Genetic Manipulation of 6-phosphofructokinase in Potato Tubers", Planta, vol. 194, (1994), pp. 95-101.
Zrenner, R. et al., "Evidence of the Crucial Role of Sucrose Synthase for Sink Strength Using Transgenic Potato Plants (*Solanum tuberosum* L.)", The Plant Journal, vol. 7, No. 1, (1995), pp. 97-107.
Jelitto, T., et al., "Inorganic Pyrophosphate Content and Metabolites in Potato and Tobacco Plants Expressing *E. coli* Pyrophosphatase in their Cytosol", Planta, vol. 188, (1992), pp. 238-244.
Partial European Search Report EP 11 15 7505 dated Nov. 11, 2011.

* cited by examiner

NUCLEIC ACID MOLECULES ENCODING *WRINKLED1*-LIKE POLYPEPTIDES AND METHODS OF USE IN PLANTS

RELATED APPLICATIONS

This application is a divisional of U.S. patent application Ser. No. 11/629,727, filed Jan. 15, 2007, which is a national stage application (under 35 U.S.C. §371) of PCT/US2005/021500 filed Jun. 16, 2005, which claims benefit to U.S. Provisional Application No. 60/580,334 filed Jun. 16, 2004 and to U.S. Provisional Application No. 60/600,466 filed Aug. 11, 2004. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Second_Revised_Sequence_Listing_13987_00133_US. The size of the text file is 168 KB, and the text file was created on Mar. 1, 2011.

FIELD OF THE INVENTION

Described herein are inventions in the field of genetic engineering of plants, including isolated nucleic acid molecules encoding polypeptides that improve agronomic, horticultural, and quality traits. This invention relates generally to nucleic acid sequences encoding proteins that are related to the presence of seed storage compounds in plants. More specifically, the present invention relates to WRINKLED1-like (WRI1-like) nucleic acid sequences encoding sugar and lipid metabolism regulator proteins and the use of these sequences in transgenic plants. In particular, the invention is directed to methods for manipulating sugar-related compounds, for increasing oil levels, and for altering the fatty acid composition in plants and seeds. The invention further relates to methods of using these novel plant polypeptides to stimulate plant growth and/or to increase yield and/or composition of seed storage compounds.

BACKGROUND OF THE INVENTION

The study and genetic manipulation of plants has a long history that began even before the framed studies of Gregor Mendel. In perfecting this science, scientists have accomplished modification of particular traits in plants ranging from potato tubers having increased starch content to oilseed plants such as canola and sunflower having increased or altered fatty acid content. With the increased consumption and use of plant oils, the modification of seed oil content and seed oil levels has become increasingly widespread (e.g. Töpfer et al., 1995, Science 268:681-686). Manipulation of biosynthetic pathways in transgenic plants provides a number of opportunities for molecular biologists and plant biochemists to affect plant metabolism giving rise to the production of specific higher-value products. The seed oil production or composition has been altered in numerous traditional oilseed plants such as soybean (U.S. Pat. No. 5,955,650), canola (U.S. Pat. No. 5,955,650), sunflower (U.S. Pat. No. 6,084,164), and rapeseed (Töpfer et al., 1995, Science 268:681-686), and non-traditional oilseed plants such as tobacco (Cahoon et al., 1992, Proc. Natl. Acad. Sci. USA 89:11184-11188).

Plant seed oils comprise both neutral and polar lipids (See Table 1). The neutral lipids contain primarily triacylglycerol, which is the main storage lipid that accumulates in oil bodies in seeds. The polar lipids are mainly found in the various membranes of the seed cells, e.g. the endoplasmic reticulum, microsomal membranes and the cell membrane. The neutral and polar lipids contain several common fatty acids (See Table 2) and a range of less common fatty acids. Lipids indicated by an asterisk in Table 2 do not normally occur in plant seed oils, but their production in transgenic plant seed oil is of importance in plant biotechnology. The fatty acid composition of membrane lipids is highly regulated, and only a select number of fatty acids are found in membrane lipids. On the other hand, a large number of unusual fatty acids can be incorporated into the neutral storage lipids in seeds of many plant species (Van de Loo et al., 1993, Unusual Fatty Acids in Lipid Metabolism in Plants pp. 91-126, editor T S Moore Jr. CRC Press; Millar et al., 2000, Trends Plant Sci. 5:95-101).

TABLE 1

Plant Lipid Classes

| | |
|---|---|
| Neutral Lipids | Triacylglycerol (TAG) |
| | Diacylglycerol (DAG) |
| | Monoacylglycerol (MAG) |
| Polar Lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

TABLE 2

Common Plant Fatty Acids

| | |
|---|---|
| 16:0 | Palmitic acid |
| 16:1 | Palmitoleic acid |
| 16:3 | Palmitolenic acid |
| 18:0 | Stearic acid |
| 18:1 | Oleic acid |
| 18:2 | Linoleic acid |
| 18:3 | Linolenic acid |
| γ-18:3 | Gamma-linolenic acid* |
| 20:0 | Arachidic acid |
| 20:1 | Eicosenoic acid |
| 22:6 | Docosahexanoic acid (DHA) * |
| 20:2 | Eicosadienoic acid |
| 20:4 | Arachidonic acid (AA) * |
| 20:5 | Eicosapentaenoic acid (EPA) * |
| 22:1 | Erucic acid |

Lipids are synthesized from fatty acids, and their synthesis may be divided into two parts: the prokaryotic pathway and the eukaryotic pathway (Browse et al., 1986, Biochemical J. 235:25-31; Ohlrogge & Browse, 1995, Plant Cell 7:957-970). The prokaryotic pathway is located in plastids that are the primary site of fatty acid biosynthesis. Fatty acid synthesis begins with the conversion of acetyl-CoA to malonyl-CoA by acetyl-CoA carboxylase (ACCase). Malonyl-CoA is converted to malonyl-acyl carrier protein (ACP) by the malonyl-CoA:ACP transacylase. The enzyme beta-keto-acyl-ACP-synthase III (KAS III) catalyzes a condensation reaction, in which the acyl group from acetyl-CoA is transferred to malonyl-ACP to form 3-ketobutyryl-ACP. In a subsequent series of condensation, reduction, and dehydration reactions, the nascent fatty acid chain on the ACP cofactor is elongated by the step-by-step addition (condensation) of two carbon atoms donated by malonyl-ACP until a 16- or 18-carbon saturated fatty acid chain is formed. The plastidial delta-9 acyl-ACP desaturase introduces the first unsaturated double bond into the fatty acid. Thioesterases cleave the fatty acids from the ACP cofactor, and free fatty acids are exported to the cytoplasm where they participate as fatty acyl-CoA esters in the eukaryotic pathway. In this pathway, the fatty acids are esterified by glycerol-3-phosphate acyltransferase and lysophosphatidic acid acyl-transferase to the sn-1 and sn-2 positions of glycerol-3-phosphate, respectively, to yield phosphatidic acid (PA). The PA is the precursor for other polar and neutral lipids, the latter being formed in the Kennedy pathway (Voelker, 1996, Genetic Engineering ed.:Setlow 18:111-113; Shanklin & Cahoon, 1998, Annu. Rev. Plant Physiol. Plant Mol. Biol. 49:611-641; Frentzen, 1998, Lipids 100:161-166; Millar et al., 2000, Trends Plant Sci. 5:95-101).

Storage lipids in seeds are synthesized from carbohydrate-derived precursors. Plants have a complete glycolytic pathway in the cytosol (Plaxton, 1996, Annu. Rev. Plant Physiol. Plant Mol. Biol. 47:185-214), and it has been shown that a complete pathway also exists in the plastids of rapeseeds (Kang & Rawsthorne, 1994, Plant J. 6:795-805). Sucrose is the primary source of carbon and energy, transported from the leaves into the developing seeds. During the storage phase of seeds, sucrose is converted in the cytosol to provide the metabolic precursors glucose-6-phosphate and pyruvate. These are transported into the plastids and converted into acetyl-CoA that serves as the primary precursor for the synthesis of fatty acids. Acetyl-CoA in the plastids is the central precursor for lipid biosynthesis. Acetyl-CoA can be formed in the plastids by different reactions and the exact contribution of each reaction is still being debated (Ohlrogge & Browse, 1995, Plant Cell 7:957-970). It is accepted, however, that a large part of the acetyl-CoA is derived from glucose-6-phosphate and pyruvate that are imported from the cytoplasm into the plastids. Sucrose is produced in the source organs (leaves, or anywhere that photosynthesis occurs) and is transported to the developing seeds that are also termed sink organs. In the developing seeds, sucrose is the precursor for all the storage compounds, i.e. starch, lipids, and partly the seed storage proteins. Therefore, it is clear that carbohydrate metabolism, in which sucrose plays a central role is very important to the accumulation of seed storage compounds.

Storage compounds such as triacylglycerols (seed oil) serve as carbon and energy reserves, which are used during germination and growth of the young seedling. Seed (vegetable) oil is also an essential component of the human diet and a valuable commodity providing feed stocks for the chemical industry. A mutant of *Arabidopsis* affected in seed storage compound metabolism is wrinkled1 (wri1) (Focks and Benning, 1998). The mutant is characterized by a 80% reduction in seed oil content. Additionally, expression of genes involved in sugar metabolism seems to be affected.

Although the lipid and fatty acid content and/or composition of seed oil can be modified by the traditional methods of plant breeding, the advent of recombinant DNA technology has allowed for easier manipulation of the seed oil content of a plant, and in some cases, has allowed for the alteration of seed oils in ways that could not be accomplished by breeding alone (See, e.g., Töpfer et al., 1995, Science 268:681-686). For example, introduction of a $\Delta^{12}$-hydroxylase nucleic acid sequence into transgenic tobacco resulted in the introduction of a novel fatty acid, ricinoleic acid, into the tobacco seed oil (Van de Loo et al., 1995, Proc. Natl. Acad. Sci. USA 92:6743-6747). Tobacco plants have also been engineered to produce low levels of petroselinic acid by the introduction and expression of an acyl-ACP desaturase from coriander (Cahoon et al., 1992, Proc. Natl. Acad. Sci. USA 89:11184-11188).

The modification of seed oil content in plants has significant medical, nutritional, and economic ramifications. With regard to the medical ramifications, the long chain fatty acids (C18 and longer) found in many seed oils have been linked to reductions in hypercholesterolemia and other clinical disorders related to coronary heart disease (Brenner, 1976, Adv. Exp. Med. Biol. 83:85-101). Therefore, consumption of a plant having increased levels of these types of fatty acids may reduce the risk of heart disease. Enhanced levels of seed oil content also increase large-scale production of seed oils and thereby reduce the cost of these oils.

In order to increase or alter the levels of compounds such as seed oils in plants, nucleic acid sequences and proteins regulating lipid and fatty acid metabolism must be identified. As mentioned earlier, several desaturase nucleic acids such as the $\Delta^6$-desaturase nucleic acid, $\Delta^{12}$-desaturase nucleic acid, and acyl-ACP desaturase nucleic acids have been cloned and demonstrated to encode enzymes required for fatty acid synthesis in various plant species. Oleosin nucleic acid sequences from such different species as canola, soybean, carrot, pine, and *Arabidopsis thaliana* also have been cloned and determined to encode proteins associated with the phospholipid monolayer membrane of oil bodies in those plants.

It has also been determined that two phytohormones, gibberellic acid (GA) and absisic acid (ABA), are involved in overall regulatory processes in seed development (e.g. Ritchie & Gilroy, 1998, Plant Physiol. 116:765-776; Arenas-Huertero et al., 2000, Genes Dev. 14:2085-2096). Both the GA and ABA pathways are affected by okadaic acid, a protein phosphatase inhibitor (Kuo et al., 1996, Plant Cell. 8:259-269). The regulation of protein phosphorylation by kinases and phosphatases is accepted as a universal mechanism of cellular control (Cohen, 1992, Trends Biochem. Sci. 17:408-413). Likewise, the plant hormones ethylene (See, e.g., Zhou et al., 1998, Proc. Natl. Acad. Sci. USA 95:10294-10299; Beaudoin et al., 2000, Plant Cell 2000:1103-1115) and auxin (e.g. Colon-Carmona et al., 2000, Plant Physiol. 124:1728-1738) are involved in controlling plant development as well.

Although several compounds are known that generally affect plant and seed development, there is a clear need to specifically identify factors that are more specific for the developmental regulation of storage compound accumulation and to identify genes which have the capacity to confer altered or increased oil production to its host plant and to other plant species. This invention discloses nucleic acid sequences from *Arabidopsis thaliana, Brassica napus, Glycine max, Oryza sativa*, or *Triticum aestivum*. These nucleic acid sequences can be used to alter or increase the levels of seed storage compounds such as proteins, sugars, and oils in plants, including transgenic plants, such as canola, linseed, soybean, sunflower, maize, oat, rye, barley, wheat, rice, pepper, tagetes, cotton, oil palm, coconut palm, flax, castor, and peanut, which are oilseed plants containing high amounts of lipid compounds.

SUMMARY OF THE INVENTION

The present invention provides novel isolated nucleic acid and amino acid sequences associated with the metabolism of seed storage compounds in plants, in particular with sequences that are WRI1-like.

The present invention also provides isolated nucleic acids from *Arabidopsis thaliana, Brassica napus, Glycine max, Oryza sativa*, and *Triticum aestivum* encoding a Lipid Metabolism Protein (LMP), or a portion thereof. These sequences may be used to modify or increase lipids and fatty acids, cofactors and enzymes in microorganisms and plants.

*Arabidopsis* plants are known to produce considerable amounts of fatty acids like linoleic and linolenic acid (See, e.g., Table 2) and for their close similarity in many aspects (gene homology, etc.) to the oil crop plant *Brassica*. Therefore, nucleic acid molecules originating from a plant like *Arabidopsis thaliana, Brassica napus, Glycine max, Oryza sativa*, or *Triticum aestivum*, or related organisms are especially suited to modify the lipid and fatty acid metabolism in a host, especially in microorganisms and plants. Furthermore, nucleic acids from *Arabidopsis thaliana, Brassica napus, Glycine max, Oryza sativa*, or *Triticum aestivum*, or related organisms can be used to identify those DNA sequences and enzymes in other species, which are useful to modify the biosynthesis of precursor molecules of fatty acids in the respective organisms.

The present invention further provides an isolated nucleic acid comprising a fragment of at least 15 nucleotides of a nucleic acid from a plant (*Arabidopsis thaliana, Brassica napus, Glycine max, Oryza sativa*, or *Triticum aestivum*) encoding a Lipid Metabolism Protein (LMP), or a portion thereof.

Also provided by the present invention are polypeptides encoded by the nucleic acids, heterologous polypeptides comprising polypeptides encoded by the nucleic acids, and antibodies to those polypeptides.

Additionally, the present invention relates to and provides the use of LMP nucleic acids in the production of transgenic plants having a modified level or composition of a seed storage compound. With regard to an altered composition, the present invention can be used, for example, to increase the percentage of oleic acid relative to other plant oils. A method of producing a transgenic plant with a modified level or composition of a seed storage compound includes the steps of transforming a plant cell with an expression vector comprising an LMP nucleic acid, and generating a plant with a modified level or composition of the seed storage compound from the plant cell. In one embodiment, the plant is a high oil producing species as described in Kinney et al. (1994, Current Opin. in Biotech. 5:144-151), Töpfer et al. (1995, Science 268:681-686), and Oil Crops of the World-Their Breeding and Utilization (1989, eds. Röbbelen, Downey, and Ashri). In a preferred embodiment, the plant is a high oil producing species selected from the group consisting of canola, linseed, soybean, sunflower, maize, oat, rye, barley, wheat, rice, pepper, tagetes, cotton, oil palm, coconut palm, flax, castor, and peanut, for example.

According to the present invention, the compositions and methods described herein can be used to alter the composition of an LMP in a transgenic plant and to increase or decrease the level of an LMP in a transgenic plant comprising increasing or decreasing the expression of an LMP nucleic acid in the plant. Increased or decreased expression of the LMP nucleic acid can be achieved through transgenic overexpression, cosuppression, antisense inhibition, or in vivo mutagenesis of the LMP nucleic acid. The present invention can also be used to increase or decrease the level of a lipid in a seed oil, to increase or decrease the level of a fatty acid in a seed oil, or to increase or decrease the level of a starch in a seed or plant.

In one embodiment, the present invention includes and provides a method for increasing total oil content in a seed comprising: transforming a plant with a nucleic acid construct that comprises as operatively linked components, a promoter and nucleic acid sequences capable of modulating the level of a WRI1-like mRNA or WRI1-like protein, and growing the plant. Furthermore, the present invention includes and provides a method for increasing the level of oleic acid in a seed comprising: transforming a plant with a nucleic acid construct that comprises as operatively linked components, a promoter and a structural nucleic acid sequence capable of increasing the level of oleic acid, and growing the plant.

The present invention provides transgenic plants having modified levels of seed storage compounds, and in particular, modified levels of a lipid, a fatty acid, or a sugar. Also included herein is a seed produced by a transgenic plant transformed by an LMP DNA sequence, wherein the seed contains the LMP DNA sequence and wherein the plant is true breeding for a modified level of a seed storage compound. The present invention additionally includes a seed oil produced by the aforementioned seed. Further provided by the present invention are vectors comprising the nucleic acids, host cells containing the vectors, and descendent plant materials from a plant produced by transforming a plant cell with the nucleic acids and/or vectors and growing the plant.

According to the present invention, the compounds, compositions, and methods described herein can be used to increase or decrease the relative percentages of a lipid in a seed oil, to increase or decrease the level of a lipid in a seed oil, to increase or decrease the level of a fatty acid in a seed oil, to increase or decrease the level of a starch or other carbohydrate in a seed or plant, or to increase or decrease the level of proteins in a seed or plant. The manipulations described herein can also be used to improve seed germination and growth of the young seedlings and plants and to enhance plant yield of seed storage compounds.

The present invention further provides a method of producing a higher or lower than normal or typical level of storage compound in a transgenic plant expressing an LMP nucleic acid from *Arabidopsis thaliana, Brassica napus, Glycine max, Oryza sativa*, or *Triticum aestivum* in the transgenic plant, wherein the transgenic plant is *Arabidopsis thaliana, Brassica napus, Glycine max, Oryza sativa, Zea mays, Triticum aestivum, Helianthus anuus*, or *Beta vulgaris*, or a species different from *Arabidopsis thaliana, Brassica napus, Glycine max, Oryza sativa*, or *Triticum aestivum*. Also included herein are compositions and methods of the modification of the efficiency of production of a seed storage compound. As used herein, where the phrase *Arabidopsis thaliana, Brassica napus, Glycine max, Oryza sativa, Zea mays, Triticum aestivum, Helianthus anuus*, or *Beta vulgaris* is used, this also means *Arabidopsis thaliana* and/or *Brassica napus* and/or *Glycine max* and/or *Oryza sativa* and/or *Triticum aestivum* and/or *Zea mays* and/or *Helianthus anuus* and/or *Beta vulgaris*.

Accordingly, the present invention provides novel isolated LMP nucleic acids and isolated LMP amino acid sequences from *Arabidopsis thaliana, Brassica napus, Glycine max, Oryza sativa*, and *Triticum aestivum*, as well as active fragments, analogs, and orthologs thereof. Those active fragments, analogs, and orthologs can also be from different plant species, as one skilled in the art will appreciate that other plant species will also contain those or related nucleic acids.

The polynucleotides and polypeptides of the present invention, including agonists and/or fragments thereof, may have uses that include modulating plant growth, and potentially plant yield, preferably increasing plant growth under adverse conditions (drought, cold, light, UV). In addition, antagonists of the present invention may have uses that include modulating plant growth and/or yield, through preferably increasing plant growth and yield. In yet another embodiment, overexpression polypeptides of the present invention using a constitutive promoter may be useful for increasing plant yield under stress conditions (drought, light, cold, UV) by modulating light utilization efficiency. Moreover, polynucleotides and polypeptides of the present invention will improve seed germination and seed dormancy and, hence, will improve plant growth and/or yield of seed storage compounds.

The isolated nucleic acid molecules of the present invention may further comprise an operatively linked promoter or partial promoter region. In one embodiment, the promoter can be a constitutive promoter, an inducible promoter, or a tissue-specific promoter. The constitutive promoter can be, for example, the superpromoter (Ni et al., Plant J. 7:661-676, 1995; U.S. Pat. No. 5,955,646) or the PtxA promoter (PF 55368-2 US, Song et al., 2004, See Example 11). The tissue-specific promoter can be active in vegetative tissue or reproductive tissue. The tissue-specific promoter active in reproductive tissue can be a seed-specific promoter. The tissue-specific promoter active in vegetative tissue can be a root-specific, shoot-specific, meristem-specific, or leaf-specific promoter. The isolated nucleic acid molecule of the present invention can still further comprise a 5' non-translated sequence, 3' non-translated sequence, introns, or a combination thereof.

The present invention also provides methods for increasing the number and/or size of one or more plant organs by expressing in a plant an isolated nucleic acid encoding a Lipid Metabolism Protein (LMP), or a portion thereof, from *Arabidopsis thaliana, Brassica napus, Glycine max, Oryza sativa*, or *Triticum aestivum*. More specifically, seed size, seed number, and/or seed weight is manipulated. Root length also can be increased, alleviating the effects of water depletion from soil, improving plant anchorage/standability and thus reducing lodging, and covering a larger volume of soil and thereby improving nutrient uptake. All of these advantages of altered root architecture have the potential to increase crop yield. Additionally, the number and size of leaves might be increased by the nucleic acid sequences provided in this application, improving photosynthetic light utilization efficiency by increasing photosynthetic light capture capacity and photosynthetic efficiency.

These and other features and advantages of the present invention will become apparent after a review of the following detailed description of the disclosed embodiments and the appended claims.

DETAILED DESCRIPTION OF THE INVENTION

Figure 1:
FIG. 1 is a schematic drawing of the binary vector T-DNA used to transform BnWRI01 and other WRI-like genes into *Arabidopsis thaliana* or crop plants. The abbreviations are defined as follows: LB, left border; pAHAS, *Arabidopsis* AHAS promoter; 3'AHAS, AHAS termination signal; PtxA, PtxA-promoter; BnWRI01, cDNA of BnWRI01; 3'NOS, termination signal; and RB, Right Border.

The present invention may be understood more readily by reference to the following detailed description of the preferred embodiments of the invention and the Examples included therein.

Before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a cell" can mean that at least one cell can be utilized.

The present invention is based, in part, on the isolation and characterization of nucleic acid molecules encoding WRI1-like LMPs from plants including *Arabidopsis thaliana*, canola (*Brassica napus*), soybean (*Glycine max*), rice (*Oryza sativa*), and wheat (*Triticum aestivum*), and other related crop species like maize, barley, linseed, sugar beet, or sunflower.

In accordance with the purposes of this invention, as embodied and described herein, this invention, in one aspect, provides an isolated nucleic acid from a plant (*Arabidopsis thaliana, Brassica napus, Glycine max, Oryza sativa*, or *Triticum aestivum*) encoding a Lipid Metabolism Protein (LMP), or a portion thereof.

One aspect of the invention pertains to isolated nucleic acid molecules that encode LMP polypeptides or biologically active portions thereof, as well as nucleic acid fragments sufficient for use as hybridization probes or primers for the identification or amplification of an LMP-encoding nucleic acid (e.g., LMP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of a gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA. An "isolated" nucleic acid molecule is one which is substantially separated from other nucleic acid molecules which are present in the natural source of the nucleic acid. Preferably, an "isolated" nucleic acid is substantially free of sequences that naturally flank the nucleic acid (i.e., sequences located at the 5' and 3' ends of the nucleic acid) in the genomic DNA of the organism, from which the nucleic acid is derived. For example, in various embodiments, the isolated LMP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Arabidopsis thaliana, Brassica napus, Glycine max, Oryza sativa*, or *Triticum aestivum* cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence as shown in the Appendix, or a portion thereof, can be isolated using standard molecular biology techniques and the sequence information provided herein. For example, an *Arabidopsis thaliana, Brassica napus, Glycine max, Oryza sativa*, or *Triticum aestivum* LMP cDNA can be isolated from an *Arabidopsis thaliana, Brassica napus, Glycine max, Oryza sativa*, or *Triticum aestivum* library using all or portion of one of the sequences as shown in the The Appendixs a hybridization probe and standard hybridization techniques (e.g., as described in Sambrook et al., 1989, *Molecular Cloning: A Laboratory Manual.* 2nd, ed., Cold Spring Harbor Laboratory, Cold Spring Harbor Laboratory Press, Cold Spring Harbor, N.Y.). Moreover, a nucleic acid molecule encompassing all or a portion of one of the sequences as shown in the Appendix can be isolated by the polymerase chain reaction using oligonucleotide primers designed based upon this sequence (e.g., a nucleic acid molecule encompassing all or a portion of one of the sequences as shown in the Appendix can be isolated by the polymerase chain reaction using oligonucleotide primers designed based upon this same sequence as shown in the Appendix). For example, mRNA can be isolated from plant cells (e.g., by the guanidinium-thiocyanate extraction procedure of Chirgwin et al., 1979, Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in The Appendix. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an LMP nucleotide sequence can be prepared by standard synthetic techniques, e.g., using an automated DNA synthesizer.

In a preferred embodiment, an isolated nucleic acid of the invention comprises one of the nucleotide sequences shown in The Appendix. The sequences as shown in the Appendix correspond to the *Arabidopsis thaliana, Brassica napus, Glycine max, Oryza sativa*, or *Triticum aestivum* LMP cDNAs of the invention. These cDNAs comprise sequences encoding LMPs (i.e., the "coding region"), as well as 5' untranslated sequences and 3' untranslated sequences. Alternatively, the nucleic acid molecules can comprise only the coding region of any of the sequences in the Appendix or can contain whole genomic fragments isolated from genomic DNA.

For the purposes of this application, it will be understood that each of the sequences set forth in the Appendix has been assigned an identifying entry number (e.g., BnWRI01). Each of these sequences may generally comprise three parts: a 5' upstream region, a coding region, and a downstream region. A coding region of these sequences is indicated as "ORF position" (Table 3).

In another preferred embodiment, an isolated nucleic acid molecule of the invention comprises a nucleic acid molecule, which is a complement of one of the nucleotide sequences shown in the Appendix, or a portion thereof A nucleic acid molecule which is complementary to one of the nucleotide sequences shown in the Appendix is one which is sufficiently complementary to one of the nucleotide sequences shown in the Appendix such that it can hybridize to one of the nucleotide sequences shown in the Appendix, thereby forming a stable duplex.

In still another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99%, or more homologous to a nucleotide sequence shown in the Appendix, or a portion thereof. In an additional preferred embodiment, an isolated nucleic acid molecule of the invention comprises a nucleotide sequence which hybridizes, e.g., hybridizes under stringent conditions, to one of the nucleotide sequences shown in the Appendix, or a portion thereof. These hybridization conditions include washing with a solution having a salt concentration of about 0.02 molar at pH 7 at about 60° C.

Moreover, the nucleic acid molecule of the invention can comprise only a portion of the coding region of one of the sequences in the Appendix, for example a fragment, which can be used as a probe or primer or a fragment encoding a biologically active portion of an LMP. The nucleotide sequences determined from the cloning of the LMP genes from *Arabidopsis thaliana, Brassica napus, Glycine max, Oryza sativa*, or *Triticum aestivum* allows for the generation of probes and primers designed for use in identifying and/or cloning LMP homologs in other cell types and organisms, as well as LMP homologs from other plants or related species. Therefore this invention also provides compounds comprising the nucleic acids disclosed herein, or fragments thereof. These compounds include the nucleic acids attached to a moiety. These moieties include, but are not limited to, detection moieties, hybridization moieties, purification moieties, delivery moieties, reaction moieties, binding moieties, and the like. The probe/primer typically comprises substantially purified oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of one of the sequences set forth in the Appendix, an anti-sense sequence of one of the sequences set forth in the Appendix, or naturally occurring mutants thereof. Primers based on a nucleotide sequence as shown in the Appendix can be used in PCR reactions to clone LMP homologs. Probes based on the LMP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an LMP, such as by measuring a level of an LMP-encoding nucleic acid in a sample of cells, e.g., detecting LMP mRNA levels or determining whether a genomic LMP gene has been mutated or deleted.

In one embodiment, the nucleic acid molecule of the invention encodes a protein or portion thereof which includes an amino acid sequence which is sufficiently homologous to an amino acid encoded by a sequence as shown in the Appendix such that the protein or portion thereof maintains the same or a similar function as the wild-type protein. As used herein, the language "sufficiently homologous" refers to proteins or portions thereof which have amino acid sequences which include a minimum number of identical or equivalent (e.g., an amino acid residue, which has a similar side chain as an amino acid residue in one of the ORFs of a sequence as shown in the Appendix) amino acid residues to an amino acid sequence such that the protein or portion thereof is able to participate in the metabolism of compounds necessary for the production of seed storage compounds in plants, construction of cellular membranes in microorganisms or plants, or in the transport of molecules across these membranes. Regulatory proteins, such as DNA binding proteins, transcription factors, kinases, phosphatases, or protein members of metabolic pathways such as the lipid, starch, and protein biosynthetic pathways, or membrane transport systems, may play a role in the biosynthesis of seed storage compounds. Examples of such activities are described herein (See putative annotations in Table 3). Examples of LMP-encoding nucleic acid sequences are set forth in the Appendix.

As altered or increased sugar and/or fatty acid production is a general trait wished to be inherited into a wide variety of plants like maize, wheat, rye, oat, triticale, rice, barley, soybean, peanut, cotton, canola, manihot, pepper, sunflower, sugar beet and tagetes, solanaceous plants like potato, tobacco, eggplant, and tomato, *Vicia* species, pea, alfalfa, bushy plants (coffee, cacao, tea), *Salix* species, trees (oil palm, coconut) and perennial grasses and forage crops, these crop plants are also preferred target plants for genetic engineering as one further embodiment of the present invention.

Portions of proteins encoded by the LMP nucleic acid molecules of the invention are preferably biologically active portions of one of the LMPs. As used herein, the term "biologically active portion of an LMP" is intended to include a portion, e.g., a domain/motif, of an LMP that participates in the metabolism of compounds necessary for the biosynthesis of seed storage lipids, or the construction of cellular membranes in microorganisms or plants, or in the transport of molecules across these membranes, or has an activity as set forth in Table 3. To determine whether an LMP or a biologically active portion thereof can participate in the metabolism of compounds necessary for the production of seed storage compounds and cellular membranes, an assay of enzymatic activity may be performed. Such assay methods are well known to those skilled in the art, and as described in Example 14.

Biologically active portions of an LMP include peptides comprising amino acid sequences derived from the amino acid sequence of an LMP (e.g., an amino acid sequence encoded by a nucleic acid as shown in the Appendix or the amino acid sequence of a protein homologous to an LMP, which include fewer amino acids than a full length LMP or the full length protein which is homologous to an LMP) and exhibit at least one activity of an LMP. Typically, biologically active portions (peptides, e.g., peptides which are, for example, 5, 10, 15, 20, 30, 35, 36, 37, 38, 39, 40, 50, 100, or more amino acids in length) comprise a domain or motif with at least one activity of an LMP. Moreover, other biologically active portions, in which other regions of the protein are deleted, can be prepared by recombinant techniques and evaluated for one or more of the activities described herein. Preferably, the biologically active portions of an LMP include one or more selected domains/motifs or portions thereof having biological activity.

Additional nucleic acid fragments encoding biologically active portions of an LMP can be prepared by isolating a portion of one of the sequences, expressing the encoded portion of the LMP or peptide (e.g., by recombinant expression in vitro) and assessing the activity of the encoded portion of the LMP or peptide.

The invention further encompasses nucleic acid molecules that differ from one of the nucleotide sequences shown in the Appendix (and portions thereof) due to degeneracy of the genetic code and thus encode the same LMP as that encoded by the nucleotide sequences shown in the Appendix. In a further embodiment, the nucleic acid molecule of the invention encodes a full length protein which is substantially homologous to an amino acid sequence of a polypeptide encoded by an open reading frame shown in the Appendix. In one embodiment, the full-length nucleic acid or protein or fragment of the nucleic acid or protein is from *Arabidopsis thaliana, Brassica napus, Glycine max, Oryza sativa,* or *Triticum aestivum*.

In addition to the *Arabidopsis thaliana, Brassica napus, Glycine max, Oryza sativa,* or *Triticum aestivum* LMP nucleotide sequences shown in the Appendix, it will be appreciated by those skilled in the art that DNA sequence polymorphisms that lead to changes in the amino acid sequences of LMPs may exist within a population (e.g., the *Arabidopsis thaliana, Brassica napus, Glycine max, Oryza sativa,* or *Triticum aestivum* population). Such genetic polymorphism in the LMP gene may exist among individuals within a population due to natural variation. As used herein, the terms "gene" and "recombinant gene" refer to nucleic acid molecules comprising an open reading frame encoding an LMP, preferably a *Arabidopsis thaliana, Brassica napus, Glycine max, Oryza sativa,* or *Triticum aestivum* LMP. Such natural variations can typically result in 1-40% variance in the nucleotide sequence of the LMP gene. Any and all such nucleotide variations and resulting amino acid polymorphisms in LMP that are the result of natural variation and that do not alter the functional activity of LMPs are intended to be within the scope of the invention.

Nucleic acid molecules corresponding to natural variants and non-*Arabidopsis thaliana,* non-*Brassica napus,* non-*Glycine max,* non-*Oryza sativa,* or non-*Triticum aestivum* orthologs of the *Arabidopsis thaliana, Brassica napus, Gly-* cine max, Oryza sativa, or Triticum aestivum LMP cDNA of the invention can be isolated based on their homology to Arabidopsis thaliana, Brassica napus, Glycine max, Oryza sativa, or Triticum aestivum LMP nucleic acid disclosed herein using the Arabidopsis thaliana, Brassica napus, Glycine max, Oryza sativa, or Triticum aestivum cDNA, or a portion thereof, as a hybridization probe according to standard hybridization techniques under stringent hybridization conditions. As used herein, the term "orthologs" refers to two nucleic acids from different species, but that have evolved from a common ancestral gene by speciation. Normally, orthologs encode proteins having the same or similar functions. Accordingly, in another embodiment, an isolated nucleic acid molecule of the invention is at least 15 nucleotides in length and hybridizes under stringent conditions to the nucleic acid molecule comprising a nucleotide sequence as shown in the Appendix. In other embodiments, the nucleic acid is at least 30, 50, 100, 250, or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y., 1989: 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Another preferred example of stringent hybridization conditions is hybridization in a 6×SSC solution at 65° C. Preferably, an isolated nucleic acid molecule of the invention that hybridizes under stringent conditions to a sequence as shown in the Appendix corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Arabidopsis thaliana, Brassica napus, Glycine max, Oryza sativa,* or *Triticum aestivum* LMP.

In addition to naturally-occurring variants of the LMP sequence that may exist in the population, the skilled artisan will further appreciate that changes can be introduced by mutation into a nucleotide sequence as shown in the Appendix, thereby leading to changes in the amino acid sequence of the encoded LMP, without altering the functional ability of the LMP. For example, nucleotide substitutions leading to amino acid substitutions at "non-essential" amino acid residues can be made in a sequence as shown in the Appendix. A "non-essential" amino acid residue is a residue that can be altered from the wild-type sequence of one of the LMPs (The Appendix) without altering the activity of said LMP, whereas an "essential" amino acid residue is required for LMP activity. Other amino acid residues, however, (e.g., those that are not conserved or only semi-conserved in the domain having LMP activity) may not be essential for activity and thus are likely to be amenable to alteration without altering LMP activity.

Accordingly, another aspect of the invention pertains to nucleic acid molecules encoding LMPs that contain changes in amino acid residues that are not essential for LMP activity. Such LMPs differ in amino acid sequence from a sequence yet retain at least one of the LMP activities described herein.

In one embodiment, the isolated nucleic acid molecule comprises a nucleotide sequence encoding a protein, wherein the protein comprises an amino acid sequence at least about 50% homologous to an amino acid sequence encoded by a nucleic acid as shown in the rhe Appendix and is capable of participation in the metabolism of compounds necessary for the production of seed storage compounds in *Arabidopsis thaliana, Brassica napus, Glycine max, Oryza sativa,* or *Triticum aestivum,* or cellular membranes, or has one or more activities set forth in Table 3. Preferably, the protein encoded by the nucleic acid molecule is at least about 50-60% homologous to one of the sequences encoded by a nucleic acid as shown in the Appendix, more preferably at least about 60-70% homologous to one of the sequences encoded by a nucleic acid as shown in the Appendix, even more preferably at least about 70-80%, 80-90%, 90-95% homologous to one of the sequences encoded by a nucleic acid as shown in the Appendix, and most preferably at least about 96%, 97%, 98%, or 99% homologous to one of the sequences encoded by a nucleic acid as shown in the Appendix.

To determine the percent homology of two amino acid sequences (e.g., one of the sequences encoded by a nucleic acid as shown in the The Appendix and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences encoded by a nucleic acid as shown in the Appendix) is occupied by the same amino acid residue or nucleotide as the corresponding position in the other sequence (e.g., a mutant form of the sequence selected from the polypeptide encoded by a nucleic acid as shown in the Appendix), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

An isolated nucleic acid molecule encoding an LMP homologous to a protein sequence encoded by a nucleic acid as shown in the Appendix can be created by introducing one or more nucleotide substitutions, additions, or deletions into a nucleotide sequence as shown in the Appendix such that one or more amino acid substitutions, additions, or deletions are introduced into the encoded protein. Mutations can be introduced into one of the sequences as shown in the Appendix by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted non-essential amino acid residue in an LMP is preferably replaced with another amino acid residue from the same side chain family. Alternatively, in another embodiment, mutations can be introduced randomly along all or part of an LMP coding sequence, such as by saturation mutagenesis, and the resultant mutants can be screened for an LMP activity described herein to identify mutants that retain LMP activity. Following mutagenesis of one of the sequences as shown in the Appendix, the encoded protein can be expressed recombinantly, and the activity of the protein can be determined using, for example, assays described herein (See Examples 14-15 and 17-18).

LMPs are preferably produced by recombinant DNA techniques. For example, a nucleic acid molecule encoding the protein is cloned into an expression vector (as described above), the expression vector is introduced into a host cell (as described herein) and the LMP is expressed in the host cell. The LMP can then be isolated from the cells by an appropriate purification scheme using standard protein purification techniques. Alternative to recombinant expression, an LMP or peptide thereof can be synthesized chemically using standard peptide synthesis techniques. Moreover, native LMP can be isolated from cells, for example using an anti-LMP antibody, which can be produced by standard techniques utilizing an LMP or fragment thereof of this invention.

The invention also provides LMP chimeric or fusion proteins. As used herein, an LMP "chimeric protein" or "fusion protein" comprises an LMP polypeptide operatively linked to a non-LMP polypeptide. An "LMP polypeptide" refers to a polypeptide having an amino acid sequence corresponding to an LMP, whereas a "non-LMP polypeptide" refers to a polypeptide having an amino acid sequence corresponding to a protein which is not substantially homologous to the LMP, e.g., a protein which is different from the LMP and which is derived from the same or a different organism. With respect to the fusion protein, the term "operatively linked" is intended to indicate that the LMP polypeptide and the non-LMP polypeptide are fused to each other so that both sequences fulfill the proposed function attributed to the sequence used. The non-LMP polypeptide can be fused to the N-terminus or C-terminus of the LMP polypeptide. For example, in one embodiment, the fusion protein is a GST-LMP (glutathione S-transferase) fusion protein in which the LMP sequences are fused to the C-terminus of the GST sequences. Such fusion proteins can facilitate the purification of recombinant LMPs. In another embodiment, the fusion protein is an LMP containing a heterologous signal sequence at its N-terminus. In certain host cells (e.g., mammalian host cells), expression and/or secretion of an LMP can be increased through use of a heterologous signal sequence.

Preferably, an LMP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (See, for example, Current Protocols in Molecular Biology, eds. Ausubel et al., John Wiley & Sons: 1992). Moreover, many expression vectors are commercially available that already encode a fusion moiety (e.g., a GST polypeptide). An LMP-encoding nucleic acid can be cloned into such an expression vector such that the fusion moiety is linked in-frame to the LMP.

In addition to the nucleic acid molecules encoding LMPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LMP coding strand, or to only a portion thereof. In one embodiment, an antisense nucleic acid molecule is antisense to a "coding region" of the coding strand of a nucleotide sequence encoding an LMP. The term "coding region" refers to the region of the nucleotide sequence comprising codons that are translated into amino acid residues (e.g., the entire coding region of BnWRI01 comprises nucleotides 1 to 1245). In another embodiment, the antisense nucleic acid molecule is antisense to a "noncoding region" of the coding strand of a nucleotide sequence encoding LMP. The term "noncoding region" refers to 5' and 3' sequences that flank the coding region that are not translated into amino acids (i.e., also referred to as 5' and 3' untranslated regions).

Given the coding strand sequences encoding LMP disclosed herein (e.g., the sequences set forth in the Appendix), antisense nucleic acids of the invention can be designed according to the rules of Watson and Crick base pairing. The antisense nucleic acid molecule can be complementary to the entire coding region of LMP mRNA, but more preferably is an oligonucleotide that is antisense to only a portion of the coding or noncoding region of LMP mRNA. For example, the antisense oligonucleotide can be complementary to the region surrounding the translation start site of LMP mRNA. An antisense oligonucleotide can be, for example, about 5, 10, 15, 20, 25, 30, 35, 40, 45, or 50 nucleotides in length. An antisense or sense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydrouracil, beta-D-galactosylqueosine, inosine, N-6-isopentenyladenine, 1-methyl-guanine, 1-methylinosine, 2,2-dimethylguanine, 2-methyladenine, 2-methylguanine, 3-methylcytosine, 5-methyl-cytosine, N-6-adenine, 7-methylguanine, 5-methyl-aminomethyluracil, 5-methoxyamino-methyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diamino-purine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another variation of the antisense technology, a double-strand interfering RNA construct can be used to cause a down-regulation of the LMP mRNA level and LMP activity in transgenic plants. This requires transforming the plants with a chimeric construct containing a portion of the LMP sequence in the sense orientation fused to the antisense sequence of the same portion of the LMP sequence. A DNA linker region of variable length can be used to separate the sense and antisense fragments of LMP sequences in the construct.

The antisense nucleic acid molecules of the invention are typically administered to a cell or generated in situ such that they hybridize with or bind to cellular mRNA and/or genomic DNA encoding an LMP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic including plant promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual units, the strands run parallel to each other (Gaultier et al., 1987, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

In still another embodiment, an antisense nucleic acid of the invention is a ribozyme. Ribozymes are catalytic RNA molecules with ribonuclease activity, which are capable of cleaving a single-stranded nucleic acid, such as an mRNA, to which they have a complementary region. Thus, ribozymes (e.g., hammerhead ribozymes (described in Haselhoff & Gerlach, 1988, Nature 334:585-591)) can be used to catalytically cleave LMP mRNA transcripts to thereby inhibit translation of LMP mRNA. A ribozyme having specificity for an LMP-encoding nucleic acid can be designed based upon the nucleotide sequence of an LMP cDNA disclosed herein (e.g., Bn01 in the Appendix) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an LMP-encoding mRNA (See, e.g., Cech et al., U.S. Pat. No. 4,987,071 and Cech et al., U.S. Pat. No. 5,116,742). Alternatively, LMP mRNA can be used to select a catalytic RNA having a specific ribonuclease activity from a pool of RNA molecules (See, e.g., Bartel & Szostak, 1993, Science 261:1411-1418).

Alternatively, LMP gene expression can be inhibited by targeting nucleotide sequences complementary to the regulatory region of an LMP nucleotide sequence (e.g., an LMP promoter and/or enhancers) to form triple helical structures that prevent transcription of an LMP gene in target cells (See, e.g., Helene, 1991, Anticancer Drug Des. 6:569-84; Helene et al., 1992, Ann. N.Y. Acad. Sci. 660:27-36; and Maher, 1992, Bioassays 14:807-15).

Another aspect of the invention pertains to vectors, preferably expression vectors, containing a nucleic acid encoding an LMP (or a portion thereof). As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. With respect to a recombinant expression vector, "operatively linked" is intended to mean that the nucleotide sequence of interest is linked to the regulatory sequence(s) in a manner which allows for expression of the nucleotide sequence and both sequences are fused to each other so that each fulfills its proposed function (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel; Gene Expression Technology: Methods in Enzymology 185, Academic Press, San Diego, Calif. (1990), or see: Gruber and Crosby, in: Methods in Plant Molecular Biology and Biotechnolgy, CRC Press, Boca Raton, Fla., eds.: Glick & Thompson, Chapter 7, 89-108 including the references therein. Regulatory sequences include those that direct constitutive expression of a nucleotide sequence in many types of host cell and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc.

The expression vectors of the invention can be introduced into host cells to thereby produce proteins or peptides, including fusion proteins or peptides, encoded by nucleic acids as described herein (e.g., LMPs, mutant forms of LMPs, fusion proteins, etc.).

The recombinant expression vectors of the invention can be designed for expression of LMPs in prokaryotic or eukaryotic cells. For example, LMP genes can be expressed in bacterial cells, insect cells (using baculovirus expression vectors), yeast, and other fungal cells (See Romanos et al., 1992, Foreign gene expression in yeast: a review, Yeast 8:423-488; van den Hondel, C.A.M.J.J. et al. 1991, Heterologous gene expression in filamentous fungi, in: More Gene Manipulations in Fungi, Bennet & Lasure, eds., p. 396-428:Academic Press: an Diego; and van den Hondel & Punt 1991, Gene transfer systems and vector development for filamentous fungi, in: Applied Molecular Genetics of Fungi, Peberdy et al., eds., p. 1-28, Cambridge University Press: Cambridge), algae (Falciatore et al., 1999, Marine Biotechnology 1:239-251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and *Stylonychia*, especially of the genus *Stylonychia lemnae* with vectors following a transformation method as described in WO 98/01572, and multicellular plant cells (See Schmidt & Willmitzer, 1988, Plant Cell Rep.:583-586; Plant Molecular Biology and Biotechnology, C Press, Boca Raton, Fla., chapter 6/7, S.71-119 (1993); White et al., Techniques for Gene Transfer, in: Transgenic Plants, Vol. 1, Engineering and Utilization, eds.: Kung and Wu, Academic Press 1993, 128-43; Potrykus, 1991, Annu. Rev. Plant Physiol. Plant Mol. Biol. 42:205-225 (and references cited therein)), or mammalian cells. Suitable host cells are discussed further in Goeddel, Gene Expression Technology: Methods in Enzymology 185, Academic Press, San Diego, Calif. 1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve one or more of the following purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase.

Typical fusion expression vectors include pGEX (Pharmacia Biotech Inc; Smith & Johnson 1988, Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the LMP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant LMP unfused to GST can be recovered by cleavage of the fusion protein with thrombin.

Examples of suitable inducible non-fusion *E. coli* expression vectors include pTrc (Amann et al., 1988, Gene 69:301-315) and pET 11d (Studier et al., 1990, Gene Expression Technology: Methods in Enzymology 185, Academic Press, San Diego, Calif. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, 1990, Gene Expression Technology: *Methods in Enzymology* 185:119-128, Academic Press, San Diego, Calif.). Another strategy is to alter the nucleic acid sequence of the nucleic acid to be inserted into an expression vector so that the individual codons for each amino acid are those preferentially utilized in the bacterium chosen for expression (Wada et al., 1992, Nucleic Acids Res. 20:2111-2118). Such alteration of nucleic acid sequences of the invention can be carried out by standard DNA synthesis techniques.

In another embodiment, the LMP expression vector is a yeast expression vector. Examples of vectors for expression in yeast *S. cerevisiae* include pYepSec1 (Baldari et al., 1987, Embo J. 6:229-234), pMFa (Kurjan & Herskowitz, 1982, Cell 30:933-943), pJRY88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: van den Hondel & Punt, 1991, in: Applied Molecular Genetics of Fungi, Peberdy et al., eds., p. 1-28, Cambridge University Press: Cambridge.

Alternatively, the LMPs of the invention can be expressed in insect cells using baculovirus expression vectors. Baculovirus vectors available for expression of proteins in cultured insect cells (e.g., Sf 9 cells) include the pAc series (Smith et al., 1983, Mol. Cell. Biol. 3:2156-2165) and the pVL series (Lucklow & Summers, 1989, Virology 170:31-39).

In yet another embodiment, a nucleic acid of the invention is expressed in mammalian cells using a mammalian expression vector. Examples of mammalian expression vectors include pCDM8 (Seed, 1987, Nature 329:840) and pMT2PC (Kaufman et al., 1987, EMBO J. 6:187-195). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells see chapters 16 and 17 of Sambrook, Fritsh and Maniatis, *Molecular Cloning: A Laboratory Manual.* 2nd, ed., Cold Spring Harbor Laboratory, Cold Spring Harbor Laboratory Press, Cold Spring Harbor, N.Y., 1989.

In another embodiment, the LMPs of the invention may be expressed in uni-cellular plant cells (such as algae, see Falciatore et al., 1999, Marine Biotechnology 1:239-251, and references therein) and plant cells from higher plants (e.g., the spermatophytes, such as crop plants). Examples of plant expression vectors include those detailed in: Becker et al., 1992, Plant Mol. Biol. 20:1195-1197; Bevan, 1984, Nucleic Acids Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

A plant expression cassette preferably contains regulatory sequences capable to drive gene expression in plant cells and which are operatively linked so that each sequence can fulfil its function such as termination of transcription, including polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof but also all other terminators functionally active in plants are suitable.

As plant gene expression is very often not limited on transcriptional levels a plant expression cassette preferably contains other operatively linked sequences like translational enhancers such as the overdrive-sequence containing the 5'-untranslated leader sequence from tobacco mosaic virus enhancing the protein per RNA ratio (Gallie et al., 1987, Nucleic Acids Res. 15:8693-8711).

Plant gene expression has to be operatively linked to an appropriate promoter conferring gene expression in a timely, cell-, or tissue specific manner. Preferred are promoters driving constitutive expression (Benfey et al., 1989, EMBO J. 8:2195-2202) like those derived from plant viruses like the 35S CAMV (Franck et al., 1980, Cell 21:285-294), the 19S CaMV (See U.S. Pat. No. 5,352,605 and WO 84/02913), or plant promoters like those from Rubisco small subunit described in U.S. Pat. No. 4,962,028. Even more preferred are seed-specific promoters driving expression of LMP proteins during all or selected stages of seed development. Seed-specific plant promoters are known to those of ordinary skill in the art and are identified and characterized using seed-specific mRNA libraries and expression profiling techniques. Seed-specific promoters include the napin-gene promoter from rapeseed (U.S. Pat. No. 5,608,152), the USP-promoter from *Vicia faba* (Baeumlein et al., 1991, Mol. Gen. Genetics 225:459-67), the oleosin-promoter from *Arabidopsis* (WO 98/45461), the phaseolin-promoter from *Phaseolus vulgaris* (U.S. Pat. No. 5,504,200), the Bce4-promoter from *Brassica* (WO 91/13980) or the legumin B4 promoter (LeB4; Baeumlein et al., 1992, Plant J. 2:233-239) as well as promoters conferring seed specific expression in monocot plants like maize, barley, wheat, rye, rice etc. Suitable promoters to note are the lpt2 or lpt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the *Sorghum* kasirin-gene, and the rye secalin gene).

Plant gene expression can also be facilitated via an inducible promoter (for a review see Gatz 1997, Annu. Rev. Plant Physiol. Plant Mol. Biol. 48:89-108). Chemically inducible promoters are especially suitable if gene expression is desired in a time specific manner. Examples for such promoters are a salicylic acid inducible promoter (WO 95/19443), a tetracycline inducible promoter (Gatz et al. 1992, Plant J. 2:397-404) and an ethanol inducible promoter (WO 93/21334).

Promoters responding to biotic or abiotic stress conditions are also suitable promoters such as the pathogen inducible PRP1-gene promoter (Ward et al., 1993, Plant. Mol. Biol. 22:361-366), the heat inducible hsp80-promoter from tomato (U.S. Pat. No. 5,187,267), cold inducible alpha-amylase promoter from potato (WO 96/12814) or the wound-inducible pinII-promoter (EP 375091).

Other preferred sequences for use in plant gene expression cassettes are targeting-sequences necessary to direct the gene-product in its appropriate cell compartment (For review, see Kermode, 1996, Crit. Rev. Plant Sci. 15:285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes, and other compartments of plant cells. Also especially suited are promoters that confer plastid-specific gene expression, as plastids are the compartment where precursors and some end products of lipid biosynthesis are synthesized. Suitable promoters such as the viral RNA polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to LMP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub et al. (1986, Antisense RNA as a molecular tool for genetic analysis, Reviews—Trends in Genetics, Vol. 1) and Mol et al. (1990, FEBS Lett. 268:427-430).

Another aspect of the invention pertains to host cells into which a recombinant expression vector of the invention has been introduced. The terms "host cell" and "recombinant host cell" are used interchangeably herein. It is to be understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an LMP can be expressed in bacterial cells, insect cells, fungal cells, mammalian cells (such as Chinese hamster ovary cells (CHO) or COS cells), algae, ciliates, or plant cells. Other suitable host cells are known to those skilled in the art.

Vector DNA can be introduced into prokaryotic or eukaryotic cells via conventional transformation or transfection techniques. As used herein, the terms "transformation," "transfection," "conjugation," and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells including plant cells can be found in Sambrook et al. (1989, Molecular Cloning: A Laboratory Manual. 2nd, ed., Cold Spring Harbor Laboratory, Cold Spring Harbor Laboratory Press, Cold Spring Harbor, N.Y.) and other laboratory manuals such as Methods in Molecular Biology 1995, Vol. 44, *Agrobacterium* protocols, ed: Gartland and Davey, Humana Press, Totowa, N.J.

For stable transfection of mammalian and plant cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin, kanamycin, and methotrexate, or in plants that confer resistance towards an herbicide such as glyphosate or glufosinate. A nucleic acid encoding a selectable marker can be introduced into a host cell on the same vector as that encoding an LMP or can be introduced on a separate vector. Cells stably transfected with the introduced nucleic acid can be identified by, for example, drug selection (e.g., cells that have incorporated the selectable marker gene will survive, while the other cells die).

To create a homologous recombinant microorganism, a vector is prepared which contains at least a portion of an LMP gene into which a deletion, addition, or substitution has been introduced to thereby alter, e.g., functionally disrupt, the LMP gene. Preferably, this LMP gene is an *Arabidopsis thaliana*, *Brassica napus*, *Glycine max*, *Oryza sativa*, or *Triticum aestivum* LMP gene, but it can be a homolog from a related plant or even from a mammalian, yeast, or insect source. In a preferred embodiment, the vector is designed such that, upon homologous recombination, the endogenous LMP gene is functionally disrupted (i.e., no longer encodes a functional protein; also referred to as a knock-out vector). Alternatively, the vector can be designed such that, upon homologous recombination, the endogenous LMP gene is mutated or otherwise altered but still encodes functional protein (e.g., the upstream regulatory region can be altered to thereby alter the expression of the endogenous LMP). To create a point mutation via homologous recombination, DNA-RNA hybrids can be used in a technique known as chimeraplasty (Cole-Strauss et al., 1999, Nucleic Acids Res. 27:1323-1330 and Kmiec, 1999, American Scientist 87:240-247). Homologous recombination procedures in *Arabidopsis thaliana* or other crops are also well known in the art and are contemplated for use herein.

In a homologous recombination vector, the altered portion of the LMP gene is flanked at its 5' and 3' ends by additional nucleic acid of the LMP gene to allow for homologous recombination to occur between the exogenous LMP gene carried by the vector and an endogenous LMP gene in a microorganism or plant. The additional flanking LMP nucleic acid is of sufficient length for successful homologous recombination with the endogenous gene. Typically, several hundreds of base pairs up to kilobases of flanking DNA (both at the 5' and 3' ends) are included in the vector (See e.g., Thomas & Capecchi, 1987, Cell 51:503, for a description of homologous recombination vectors). The vector is introduced into a microorganism or plant cell (e.g., via polyethyleneglycol mediated DNA). Cells in which the introduced LMP gene has homologously recombined with the endogenous LMP gene are selected using art-known techniques.

In another embodiment, recombinant microorganisms can be produced which contain selected systems, which allow for regulated expression of the introduced gene. For example, inclusion of an LMP gene on a vector placing it under control of the lac operon permits expression of the LMP gene only in the presence of IPTG. Such regulatory systems are well known in the art.

A host cell of the invention, such as a prokaryotic or eukaryotic host cell in culture can be used to produce (i.e., express) an LMP. Accordingly, the invention further provides methods for producing LMPs using the host cells of the invention. In one embodiment, the method comprises culturing a host cell of the invention (into which a recombinant expression vector encoding an LMP has been introduced, or which contains a wild-type or altered LMP gene in it's genome) in a suitable medium until LMP is produced. In another embodiment, the method further comprises isolating LMPs from the medium or the host cell.

Another aspect of the invention pertains to isolated LMPs, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of LMP in which the protein is separated from cellular components of the cells in which it is naturally or recombinantly produced. In one embodiment, the language "substantially free of cellular material" includes preparations of LMP having less than about 30% (by dry weight) of non-LMP (also referred to herein as a "contaminating protein"), more preferably less than about 20% of non-LMP, still more preferably less than about 10% of non-LMP, and most preferably less than about 5% non-LMP. When the LMP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of LMP in which the protein is separated from chemical precursors or other chemicals that are involved in the synthesis of the protein. In one embodiment, the language "substantially free of chemical precursors or other chemicals" includes preparations of LMP having less than about 30% (by dry weight) of chemical precursors or non-LMP chemicals, more preferably less than about 20% chemical precursors or non-LMP chemicals, still more preferably less than about 10% chemical precursors or non-LMP chemicals, and most preferably less than about 5% chemical precursors or non-LMP chemicals. In preferred embodiments, isolated proteins or biologically active portions thereof lack contaminating proteins from the same organism from which the LMP is derived. Typically, such proteins are produced by recombinant expression of, for example, an *Arabidopsis thaliana*, *Brassica napus*, *Glycine max*, *Oryza sativa*, or *Triticum aestivum* LMP in other plants than *Arabidopsis thaliana*, *Brassica napus*, *Glycine max*, *Oryza sativa*, or *Triticum aestivum* or microorganisms, algae, or fungi.

An isolated LMP or a portion thereof of the invention can participate in the metabolism of compounds necessary for the production of seed storage compounds in *Arabidopsis thaliana*, *Brassica napus*, *Glycine max*, *Oryza sativa*, or *Triticum aestivum* or of cellular membranes, or has one or more of the activities set forth in Table 3. In preferred embodiments, the protein or portion thereof comprises an amino acid sequence which is sufficiently homologous to an amino acid sequence encoded by a nucleic acid as shown in the Appendix such that the protein or portion thereof maintains the ability to participate in the metabolism of compounds necessary for the construction of cellular membranes in *Arabidopsis thaliana*,

*Brassica napus, Glycine max, Oryza sativa*, or *Triticum aestivum*, or in the transport of molecules across these membranes. The portion of the protein is preferably a biologically active portion as described herein. In another preferred embodiment, an LMP of the invention has an amino acid sequence encoded by a nucleic acid as shown in the Appendix. In yet another preferred embodiment, the LMP has an amino acid sequence which is encoded by a nucleotide sequence which hybridizes, e.g., hybridizes under stringent conditions, to a nucleotide sequence as shown in the Appendix. In still another preferred embodiment, the LMP has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99%, or more homologous to one of the amino acid sequences encoded by a nucleic acid as shown in the Appendix. The preferred LMPs of the present invention also preferably possess at least one of the LMP activities described herein. For example, a preferred LMP of the present invention includes an amino acid sequence encoded by a nucleotide sequence which hybridizes, e.g., hybridizes under stringent conditions, to a nucleotide sequence as shown in the Appendix, and which can participate in the metabolism of compounds necessary for the construction of cellular membranes in *Arabidopsis thaliana, Brassica napus, Glycine max, Oryza sativa*, or *Triticum aestivum*, or in the transport of molecules across these membranes, or which has one or more of the activities set forth in Table 3.

In other embodiments, the LMP is substantially homologous to an amino acid sequence encoded by a nucleic acid as shown in the Appendix and retains the functional activity of the protein of one of the sequences encoded by a nucleic acid as shown in the Appendix yet differs in amino acid sequence due to natural variation or mutagenesis, as described in detail above. Accordingly, in another embodiment, the LMP is a protein which comprises an amino acid sequence which is at least about 50-60%, preferably at least about 60-70%, and more preferably at least about 70-80, 80-90, 90-95%, and most preferably at least about 96%, 97%, 98%, 99%, or more homologous to an entire amino acid sequence and which has at least one of the LMP activities described herein. In another embodiment, the invention pertains to a full *Arabidopsis thaliana, Brassica napus, Glycine max, Oryza sativa*, or *Triticum aestivum* protein which is substantially homologous to an entire amino acid sequence encoded by a nucleic acid as shown in the Appendix.

Dominant negative mutations or trans-dominant suppression can be used to reduce the activity of an LMP in transgenics seeds in order to change the levels of seed storage compounds. To achieve this a mutation that abolishes the activity of the LMP is created and the inactive non-functional LMP gene is overexpressed in the transgenic plant. The inactive trans-dominant LMP protein competes with the active endogenous LMP protein for substrate or interactions with other proteins and dilutes out the activity of the active LMP. In this way the biological activity of the LMP is reduced without actually modifying the expression of the endogenous LMP gene. This strategy was used by Pontier et al to modulate the activity of plant transcription factors (Pontier et al., Plant J 2001 27(6): 529-38).

Homologs of the LMP can be generated by mutagenesis, e.g., discrete point mutation or truncation of the LMP. As used herein, the term "homolog" refers to a variant form of the LMP that acts as an agonist or antagonist of the activity of the LMP. An agonist of the LMP can retain substantially the same, or a subset, of the biological activities of the LMP. An antagonist of the LMP can inhibit one or more of the activities of the naturally occurring form of the LMP by, for example, competitively binding to a downstream or upstream member of the cell membrane component metabolic cascade which includes the LMP, or by binding to an LMP which mediates transport of compounds across such membranes, thereby preventing translocation from taking place.

In an alternative embodiment, homologs of the LMP can be identified by screening combinatorial libraries of mutants, e.g., truncation mutants, of the LMP for LMP agonist or antagonist activity. In one embodiment, a variegated library of LMP variants is generated by combinatorial mutagenesis at the nucleic acid level and is encoded by a variegated gene library. A variegated library of LMP variants can be produced by, for example, enzymatically ligating a mixture of synthetic oligonucleotides into gene sequences such that a degenerate set of potential LMP sequences is expressible as individual polypeptides, or alternatively, as a set of larger fusion proteins (e.g., for phage display) containing the set of LMP sequences therein. There are a variety of methods that can be used to produce libraries of potential LMP homologs from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LMP sequences. Methods for synthesizing degenerate oligonucleotides are known in the art (See, e.g., Narang, 1983, Tetrahedron 39:3; Itakura et al., 1984, Annu. Rev. Biochem. 53:323; Itakura et al. 1984, Science 198:1056; Ike et al. 1983, Nucleic Acids Res. 11:477).

In addition, libraries of fragments of the LMP coding sequences can be used to generate a variegated population of LMP fragments for screening and subsequent selection of homologs of an LMP. In one embodiment, a library of coding sequence fragments can be generated by treating a double stranded PCR fragment of an LMP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S nuclease, and ligating the resulting fragment library into an expression vector. By this method, an expression library can be derived which encodes N-terminal, C-terminal, and internal fragments of various sizes of the LMP.

Several techniques are known in the art for screening gene products of combinatorial libraries made by point mutations or truncation, and for screening cDNA libraries for gene products having a selected property Such techniques are adaptable for rapid screening of the gene libraries generated by the combinatorial mutagenesis of LMP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify LMP homologs (Arkin & Yourvan, 1992, Proc. Natl. Acad. Sci. USA 89:7811-7815; Delgrave et al., 1993, Protein Engineering 6:327-331). In another embodiment, cell based assays can be exploited to analyze a variegated LMP library, using methods well known in the art.

The nucleic acid molecules, proteins, protein homologs, fusion proteins, primers, vectors, and host cells described herein can be used in one or more of the following methods: identification of *Arabidopsis thaliana, Brassica napus, Glycine max, Oryza sativa*, or *Triticum aestivum* and related organisms; mapping of genomes of organisms related to *Arabidopsis thaliana, Brassica napus, Glycine max, Oryza sativa*, or *Triticum aestivum*; identification and localization of *Arabidopsis thaliana, Brassica napus, Glycine max, Oryza sativa*, or *Triticum aestivum* sequences of interest; evolutionary studies; determination of LMP regions required for function; modulation of an LMP activity; modulation of the metabolism of one or more cell functions; modulation of the transmembrane transport of one or more compounds; modulation of seed storage compound accumulation; modulation of the number and/or size of a plant organ; modulation of seed size, number, or weight; modulation of root length; and modulation of leaf size.

The plant *Arabidopsis thaliana* represents one member of higher (or seed) plants. It is related to other plants such as *Brassica napus, Glycine max, Oryza sativa*, and *Triticum aestivum* which require light to drive photosynthesis and growth. Plants like *Arabidopsis thaliana, Brassica napus, Glycine max, Oryza sativa*, and *Triticum aestivum* share a high degree of homology on the DNA sequence and polypeptide level, allowing the use of heterologous screening of DNA molecules with probes evolving from other plants or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of *Arabidopsis* genomes, or of genomes of related organisms.

The LMP nucleic acid molecules of the invention have a variety of uses. First, the nucleic acid and protein molecules of the invention may serve as markers for specific regions of the genome. This has utility not only in the mapping of the genome, but also for functional studies of *Arabidopsis thaliana, Brassica napus, Glycine max, Oryza sativa*, or *Triticum aestivum* proteins. For example, to identify the region of the genome to which a particular *Arabidopsis thaliana, Brassica napus, Glycine max, Oryza sativa*, or *Triticum aestivum* DNA-binding protein binds, the *Arabidopsis thaliana, Brassica napus, Glycine max, Oryza sativa*, or *Triticum aestivum* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Arabidopsis thaliana, Brassica napus, Glycine max, Oryza sativa*, or *Triticum aestivum*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related plants.

The LMP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the LMP nucleic acid molecules of the invention may result in the production of LMPs having functional differences from the wild-type LMPs. These proteins may be improved in efficiency or activity, may be present in greater numbers in the cell than is usual, or may be decreased in efficiency or activity.

There are a number of mechanisms by which the alteration of an LMP of the invention may directly affect the accumulation and/or composition of seed storage compounds. In the case of plants expressing LMPs, increased transport can lead to altered accumulation of compounds and/or solute partitioning within the plant tissue and organs which ultimately could be used to affect the accumulation of one or more seed storage compounds during seed development. An example is provided by Mitsukawa et al. (1997, Proc. Natl. Acad. Sci. USA 94:7098-7102), where overexpression of an *Arabidopsis* high-affinity phosphate transporter gene in tobacco cultured cells enhanced cell growth under phosphate-limited conditions. Phosphate availability also affects significantly the production of sugars and metabolic intermediates (Hurry et al., 2000, Plant J. 24:383-396) and the lipid composition in leaves and roots (Härtel et al., 2000, Proc. Natl. Acad. Sci. USA 97:10649-10654). Likewise, the activity of the plant ACCase has been demonstrated to be regulated by phosphorylation (Savage & Ohlrogge, 1999, Plant J. 18:521-527), and alterations in the activity of the kinases and phosphatases (LMPs) that act on the ACCase could lead to increased or decreased levels of seed lipid accumulation. Moreover, the presence of lipid kinase activities in chloroplast envelope membranes suggests that signal transduction pathways and/ or membrane protein regulation occur in envelopes (See, e.g., Müller et al., 2000, J. Biol. Chem. 275:19475-19481 and literature cited therein). The ABI1 and ABI2 genes encode two protein serine/threonine phosphatases 2C, which are regulators in abscisic acid signaling pathway, and thereby in early and late seed development (e.g. Merlot et al., 2001, Plant J. 25:295-303).

The present invention also provides antibodies that specifically bind to an LMP polypeptide, or a portion thereof, as encoded by a nucleic acid disclosed herein or as described herein. Antibodies can be made by many well-known methods (See, e.g. Harlow and Lane, "Antibodies; A Laboratory Manual" Cold Spring Harbor Laboratory, Cold Spring Harbor, N.Y., 1988). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced (See, for example, Kelly et al. 1992, Bio/Technology 10:163-167; Bebbington et al., 1992, Bio/Technology 10:169-175).

The phrase "selectively binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immuno-assays are routinely used to select antibodies selectively immunoreactive with a protein. See Harlow and Lane. "Antibodies, A Laboratory Manual" Cold Spring Harbor Publications, New York (1988), for a description of immunoassay formats and conditions that could be used to determine selective binding. In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It also will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and Examples be considered as exemplary only, with a true scope and spirit of the invention being indicated by the claims included herein.

EXAMPLES

Example 1

General Processes
a) General Cloning Processes:

Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989, Cold Spring Harbor Laboratory Press: ISBN 0-87969-309-6) or Kaiser, Michaelis and Mitchell (1994, "Methods in Yeast Genetics," Cold Spring Harbor Laboratory Press: ISBN 0-87969-451-3).
b) Chemicals:

The chemicals used were obtained, if not mentioned otherwise in the text, in p.a. quality from the companies Fluka (Neu-Ulm), Merck (Darmstadt), Roth (Karlsruhe), Serva (Heidelberg), and Sigma (Deisenhofen). Solutions were prepared using purified, pyrogen-free water, designated as $H_2O$ in the following text, from a Milli-Q water system water purification plant (Millipore, Eschborn). Restriction endonucleases, DNA-modifying enzymes and molecular biology kits were obtained from the companies AGS (Heidelberg), Amersham (Braunschweig), Biometra (Göttingen), Boehringer (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). They were used, if not mentioned otherwise, according to the manufacturer's instructions.
c) Plant Material and Growth:
*Arabidopsis* Plants For this study, root material, leaves, siliques and seeds of wild-type and mutant plants of *Arabidopsis thaliana* were used. The wri1 mutation was isolated from an ethyl methanesulfonate-mutagenized population of the Columbia ecotype as described (Benning et al. 1998, Plant Physiol. 118:91-101). Wild type and wri1 *Arabidopsis* seeds were preincubated for three days in the dark at 4° C. before placing them into an incubator (AR-75, Percival Scientific, Boone, Iowa) at a photon flux density of 60-80 $\mu mol\ m^{-2}\ s^{-1}$ and a light period of 16 hours (22° C.), and a dark period of 8 hours (18° C.). All plants were started on half-strength MS medium (Murashige & Skoog, 1962, Physiol. Plant. 15, 473-497), pH 6.2, 2% sucrose and 1.2% agar. Seeds were sterilized for 20 minutes in 20% bleach 0.5% triton X100 and rinsed 6 times with excess sterile water. Plants were either grown as described above or on soil under standard conditions as described in Focks & Benning (1998, Plant Physiol. 118:91-101).
*Brassica napus*

*Brassica napus* varieties AC Excel and Cresor were used for this study to create cDNA libraries. Seed, seed pod, flower, leaf, stem and root tissues were collected from plants that were in some cases dark-, salt-, heat- and drought-treated. However, this study focused on the use of seed and seed pod tissues for cDNA libraries. Plants were tagged to harvest seeds collected 60-75 days after planting from two time points: 1-15 days and 15-25 days after anthesis. Plants have been grown in Metromix (Scotts, Marysville, Ohio) at 71° F. under a 14 hour photoperiod. Six seed and seed pod tissues of interest in this study were collected to create the following cDNA libraries: Immature seeds, mature seeds, immature seed pods, mature seed pods, night-harvested seed pods, and Cresor variety (high erucic acid) seeds. Tissue samples were collected within specified time points for each developing tissue and multiple samples within a time frame pooled together for eventual extraction of total RNA. Samples from immature seeds were taken between 1-25 days after anthesis (daa), mature seeds between 25-50 daa, immature seed pods between 1-15 daa, mature seed pods between 15-50 daa, night-harvested seed pods between 1-50 daa and Cresor seeds 5-25 daa.
*Glycine max*

*Glycine max* cv. Resnick was used for this study to create cDNA libraries. Seed, seed pod, flower, leaf, stem and root tissues were collected from plants that were in some cases dark-, salt-, heat- and drought-treated. In some cases plants have been nematode infected as well. However, this study focused on the use of seed and seed pod tissues for cDNA libraries. Plants were tagged to harvest seeds at the set days after anthesis: 5-15, 15-25, 25-35, and 33-50.
*Oryza sativa*

*Oryza sativa* ssp. Japonica cv. Nippon-bane was used for this study to create cDNA libraries. Seed, seed pod, flower, leaf, stem, and root tissues were collected from plants that were in some cases dark-, salt-, heat- and drought-treated. This study focused on the use of seed embryo tissues for cDNA libraries. Embryo and endosperm were collected separately in case endosperm tissue might interfere with RNA extraction. Plants have been grown in the greenhouse on Wisconsin soil (has high organic matter) at 85° F. under a 14-hour photoperiod. Rice embryos were dissected out of the developing seeds.

*Triticum aestivum*

*Triticum aestivum* cv. Galeon was used for this study to create cDNA libraries. Seed, flower, fruits, leaf, stem, and root tissues were collected from plants that were in some cases dark-, salt-, heat- and drought-treated. Plants have been grown in the greenhouse in metromix under a 12-h photoperiod at 72° F. during the day period and 65° F. during the night period.

Example 2

Total DNA Isolation from Plants

The details for the isolation of total DNA relate to the working up of one gram fresh weight of plant material.

CTAB buffer: 2% (w/v) N-cethyl-N,N,N-trimethylammonium bromide (CTAB); 100 mM Tris HCl pH 8.0; 1.4 M NaCl; 20 mM EDTA. N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 μl of N-laurylsarcosine buffer, 20 μl of (3-mercaptoethanol and 10 μl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000 g at room temperature for 15 minutes in each case. The DNA was then precipitated at −70° C. for 30 minutes using ice-cold isopropanol. The precipitated DNA was sedimented at 4° C. and 10,000 g for 30 min and resuspended in 180 μl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 μl of H$_2$O+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and poly-(A)+ RNA from Plants

*Arabidopsis thaliana*

For the investigation of transcripts, both total RNA and poly-(A)+ RNA were isolated. RNA was isolated from siliques of *Arabidopsis* plants according to the following procedure:

RNA preparation from *Arabidopsis* Seeds—"Hot" Extraction:
1. Buffers, Enzymes, and Solutions
  2 M KCl
  Proteinase K
  Phenol (for RNA)
  Chloroform:Isoamylalcohol
  (Phenol:choloroform 1:1; pH adjusted for RNA)
  4 M LiCl, DEPC-treated
  DEPC-treated water
  3M NaOAc, pH 5, DEPC-treated
  Isopropanol
  70% ethanol (made up with DEPC-treated water)
  Resuspension buffer:
  0.5% SDS, 10 mM Tris pH 7.5, 1 mM EDTA made up with DEPC-treated water as this solution can not be DEPC-treated
  Extraction Buffer:
  0.2 M Na Borate
  30 mM EDTA
  30 mM EGTA
  1% SDS (250 nl of 10% SDS-solution for 2.5 ml buffer)
  1% Deoxycholate (25 mg for 2.5 ml buffer)
  2% PVPP (insoluble—50 mg for 2.5 ml buffer)
  2% PVP 40K (50 mg for 2.5 ml buffer)
  10 mM DTT
  100 mM β-Mercaptoethanol (fresh, handle under fume hood—use 35 μl of 14.3 M solution for 5 ml buffer)
2. Extraction The extraction buffer was heated to 80° C. Tissues were ground in liquid nitrogen-cooled mortar, and tissue powder was transferred to 1.5 ml tubes. Because tissue should be kept frozen until buffer is added, the sample was transferred with a pre-cooled spatula, and the tube was kept in liquid nitrogen at all times. Then 350 μl preheated extraction buffer was added (here, for 100 mg tissue, buffer volume was as much as 500 nl for bigger samples) to tube, vortexed, heated to 80° C. for approximately 1 minute, and then kept on ice. Samples were vortexed and then ground additionally with electric mortar.

3. Digestion

Proteinase K (0.15 mg/100 mg tissue) was added. Then the samples were vortexed and kept at 37° C. for one hour.

First Purification

First, 27 μl 2M KCl was added, and then the samples were chilled on ice for 10 minutes. The samples were then centrifuged at 12,000 rpm for 10 minutes at room temperature and then the supernatant was transferred to fresh, RNAase-free tubes One phenol extraction was performed, followed by a chloroform:isoamylalcohol extraction. One volume isopropanol was added to the supernatant, and the mixture was chilled on ice for 10 minutes. RNA was pelleted by centrifugation (7,000 rpm for 10 minutes at room temperature). The RNA pellets were dissolved in 1 ml 4 M LiCl by vortexing for 10 to 15 minutes, followed by pelleting the RNA by a 5 minute centrifugation.

Second Purification

The pellets were resuspended in 500 μl Resuspension buffer. Then, 500 μl phenol was added, and the samples were vortexed. Then, 250 μl chloroform:isoamylalcohol was added, the samples were vortexed and centrifuged for 5 minutes. The supernatant was transferred to a fresh tube, and chloform:isoamylalcohol extraction was repeated until the interface was clear. The supernatant was transferred to a fresh tube, and 1/10 volume 3 M NaOAc, pH 5 and 600 μl isopropanol were added. The samples were kept at −20° C. for 20 minutes or longer. RNA was pelleted by a 10 minute centrifugation. The pellets were washed once with 70% ethanol. All remaining alcohol was removed before resolving pellet with 15 to 20 μl DEPC-treated water. The quantity and quality was determined by measuring the absorbance of a 1:200 dilution at 260 and 280 nm. 40 μg RNA/ml=1 OD260

RNA from wild-type and the wri1 mutant of *Arabidopsis* was isolated as described (Hosein, 2001, Plant Mol. Biol. Rep., 19:65a-65e; Ruuska et al., 2002, Plant Cell, 14:1191-1206). The mRNA was prepared from total RNA, using the Amersham Pharmacia Biotech mRNA purification kit, which utilizes oligo(dT)-cellulose columns.

Poly-(A)+ RNA was isolated using Dyna Beads® (Dynal, Oslo, Norway) following the manufacturer's instructions. After determination of the concentration of the RNA or of the poly(A)+ RNA, the RNA was precipitated by addition of 1/10 volumes of 3 M sodium acetate pH 4.6 and 2 volumes of ethanol and stored at −70° C.

*Brassica napus, Glycine max, Oryza sativa* and *Triticum aestivum*

*Brassica napus* and *Glycine max* seeds were separated from pods to create homogeneous materials for seed and seed pod cDNA libraries. Tissues were ground into fine powder under liquid $N_2$ using a mortar and pestle and transferred to a 50 ml tube. Tissue samples were stored at −80° C. until extractions could be performed.

In the case of *Oryza sativa*, 5K-10K embryos and endosperm were isolated through dissection. Tissues were place in small tubes or petri dishes on ice during dissection. Containers were placed on dry ice, then stored at −80° C.

In the case of *Triticum aestivum*, seed germination samples of Galeon wheat seeds were planted at a depth of 2" in metromix in a 20"×12" flat. The soil was soaked liberally with water and then watered twice daily. Then, 3-4 days later when the coleopiles were approximately 1 cm, the seedlings were washed with water and blotted. To create flower cDNA libraries an equal number of heads are collected at 30%, 60%, and 100% head emergence from the sheath on each of two days. There were no anthers showing yet. In order to generate seed tissue cDNA libraries grains were either watery ripe or in milk stage depending on the position of grains in the head; for later seed developmental stages, only the seed heads were harvested. For the root libraries, only roots were harvested. Plants had one main stem and three strong tillers. Plants were grown in pots, the medium was washed off, and the roots were saved for this sample. Plants were untreated.

Total RNA was extracted from tissues using RNeasy Maxi kit (Qiagen) according to the manufacturer's protocol, and mRNA was processed from total RNA using the Oligotex mRNA Purification System kit (Qiagen), also according to the manufacturer's protocol. Then mRNA was sent to Hyseq Pharmaceuticals Incorporated (Sunnyville, Calif.) for further processing of the mRNA from each tissue type into cDNA libraries and for use in their proprietary processes in which similar inserts in plasmids are clustered based on hybridization patterns.

Example 4 cDNA Library Construction

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

*Brassica napus, Glycine max, Oryza sativa*, and *Triticum aestivum* cDNA libraries were generated at Hyseq Pharmaceuticals Incorporated (Sunnyville, Calif.). No amplification steps were used in the library production to retain expression information. Hyseq's genomic approach involves grouping the genes into clusters and then sequencing representative members from each cluster. cDNA libraries were generated from oligo dT column purified mRNA. Colonies from transformation of the cDNA library into *E. coli* were randomly picked, and the cDNA inserts were amplified by PCR and spotted on nylon membranes. A set of $^{33}$-P radiolabeled oligonucleotides were hybridized to the clones and the resulting hybridization pattern determined to which cluster a particular clone belonged. cDNA clones and their DNA sequences were obtained for use in overexpression in transgenic plants and in other molecular biology processes described herein.

Example 5

Identification of LMP Genes of Interest that are WRI1-Like wri1 Mutant of *Arabidopsis thaliana*

The wri1 *Arabidopsis* mutant was used to identify LMP-encoding genes. The wri1 mutant is characterized by an 80% reduction in seed storage lipids (Focks & Benning, 1998, Plant Physiol. 118:91-101). The WRI1 gene has been cloned and described (Benning & Cernac, 2002, WO 02/072775 A2).

*Brassica napus, Glycine max, Oryza sativa* and *Triticum aestivum*

This example illustrates how cDNA clones encoding WRI1-like polypeptides of *Brassica napus, Glycine max, Oryza sativa*, and *Triticum aestivum* were identified and isolated.

In order to identify WRI1-like genes, a similarity analysis using BLAST software (Basic Local Alignment Search Tool, Altschul et al., 1990, J. Mol. Biol. 215:403-410) was performed. The amino acid sequence of the *Arabidopsis* WRI1 polypeptide was used as a query to search and align DNA databases from *Brassica napus, Glycine max, Oryza sativa*, and *Triticum aestivum* that were translated in all six reading frames, using the TBLASTN algorithm. Such similarity analysis of proprietary databases resulted in the identification of numerous ESTs and cDNA contigs.

RNA expression profile data obtained from the Hyseq clustering process was used to determine organ-specificity. Clones showing a greater expression in seed libraries compared to the other tissue libraries were selected as LMP candidate genes. The *Brassica napus, Glycine max, Oryza sativa*, and *Triticum aestivum* clones were selected for overexpression in *Arabidopsis* based on their expression profile.

Example 6

Cloning of Full-Length cDNAs and Orthologs of Identified LMP Genes

Clones corresponding to full-length sequences and partial cDNAs from *Arabidopsis thaliana, Brassica napus, Glycine max, Oryza sativa*, and *Triticum aestivum* had been identified in the proprietary databases. The clones were sequenced using a ABI 377 slab gel sequencer and BigDye Terminator Ready Reaction kits (PE Biosystems, Foster City, Calif.).

Sequence alignments were done to determine whether the clones were full-length or partial clones. In cases where the clones were determined to be partial cDNAs, the following procedure was used to isolate the full-length sequences. Full-length cDNAs were isolated by RACE PCR using the SMART RACE cDNA amplification kit from Clontech allowing both 5'- and 3' rapid amplification of cDNA ends (RACE). The RACE PCR primers were designed based on the clone sequences. The isolation of full-length cDNAs and the RACE PCR protocol used were based on the manufacturer's conditions. The RACE product fragments were extracted from agarose gels with a QIAquick Gel Extraction Kit (Qiagen) and ligated into the TOPO pCR 2.1 vector (Invitrogen) following the manufacturer's instructions. Recombinant vectors were transformed into TOP10 cells (Invitrogen) using standard conditions (Sambrook et al., 1989). Transformed cells were grown overnight at 37° C. on LB agar containing 50 µg/ml kanamycin and spread with 40 µl of a 40 mg/ml stock solution of X-gal in dimethylformamide for blue-white selection. Single white colonies were selected and used to inoculate 3 ml of liquid LB containing 50 µg/ml kanamycin and grown overnight at 37° C. Plasmid DNA was extracted using the QIAprep Spin Miniprep Kit (Qiagen) following the manufacturer's instructions. Subsequent analyses of clones and restriction mapping was performed according to standard molecular biology techniques (Sambrook et al., 1989).

Full-length cDNAs were isolated and cloned into binary vectors by using the following procedure: Gene specific primers were designed using the full-length sequences obtained from the clones or subsequent RACE amplification products. Full-length sequences and genes were amplified utilizing the clones or cDNA libraries as DNA template using touch-down PCR. In some cases, primers were designed to add an "AACA" Kozak-like sequence just upstream of the gene start codon, and two bases downstream were, in some cases, changed to GC to facilitate increased gene expression levels (Chandrashekhar et al., 1997, Plant Molecular Biology 35:993-1001). PCR reaction cycles were: 94° C., 5 minutes; 9 cycles of 94° C., 1 minutes, 65° C., 1 minute, 72° C., 4 minutes and in which the anneal temperature was lowered by 1° C. each cycle; 20 cycles of 94° C., 1 minute, 55° C., 1 minute, 72° C., 4 minutes; and the PCR cycle was ended with 72° C., 10 minutes. Amplified PCR products were gel purified from 1% agarose gels using GenElute-EtBr spin columns (Sigma) and after standard enzymatic digestion, were ligated into the plant binary vector pBPS-GB1 for transformation of Arabidopsis. The binary vector was amplified by overnight growth in E. coli DH5 in LB media and appropriate antibiotic, and plasmid was prepared for downstream steps using Qiagen MiniPrep DNA preparation kit. The insert was verified throughout the various cloning steps by determining its size through restriction digest and inserts were sequenced to ensure the expected gene was used in Arabidopsis transformation.

Gene sequences can be used to identify homologous or heterologous genes (orthologs, the same LMP gene from another plant) from cDNA or genomic libraries. This can be done by designing PCR primers to conserved sequences identified by multiple sequence alignments. Orthologs are often identified by designing degenerate primers to full-length or partial sequences of genes of interest.

Gene sequences can be used to identify homologs or orthologs from cDNA or genomic libraries. Homologous genes (e.g. full-length cDNA clones) can be isolated via nucleic acid hybridization using for example cDNA libraries: Depending on the abundance of the gene of interest, 100,000 up to 1,000,000 recombinant bacteriophages are plated and transferred to nylon membranes. After denaturation with alkali, DNA is immobilized on the membrane by, e.g., UV cross linking. Hybridization is carried out at high stringency conditions. Aqueous solution hybridization and washing is performed at an ionic strength of 1 M NaCl and a temperature of 68° C. Hybridization probes are generated by e.g. radioactive ($^{32}P$) nick transcription labeling (High Prime, Roche, Mannheim, Germany). Signals are detected by autoradiography.

Partially homologous or heterologous genes that are related but not identical can be identified in a procedure analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homology (or sequence identity/similarity) only in a distinct domain of (for example 10-20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by for example nick transcription. Hybridization is normally performed at low stringency conditions using high oligonucleotide concentrations.

Oligonucleotide Hybridization Solution:
6×SSC
0.01 M sodium phosphate
1 mM EDTA (pH 8)
0.5 SDS
100 µg/ml denaturated salmon sperm DNA
0.1% nonfat dried milk During hybridization, temperature is lowered stepwise to 5-10° C. below the estimated oligonucleotide $T_m$ or down to room temperature followed by washing steps and autoradiography. Washing is performed with low stringency such as 3 washing steps using 4×SSC. Further details are described by Sambrook et al. (1989, "Molecular Cloning: A Laboratory Manual", Cold Spring Harbor Laboratory Press) or Ausubel et al. (1994, "Current Protocols in Molecular Biology", John Wiley & Sons).

TABLE 3

Putative functions of the WRI1-like LMPs
(full length nucleic acid sequences can be found in the
Appendix using the sequence codes in Table 3)

| Seq ID | Sequence name | Species | Function | ORF position |
|---|---|---|---|---|
| 1 | AtWRI01 | Arabidopsis thaliana | WRINKLED 1 transcription factor involved in glycolysis/oil biosynthesis | 117-1406 |
| 4 | BnWRI22743-1 | Brassica napus | Ap2 domain transcription factor | 6-1340 |

TABLE 3-continued

Putative functions of the WRI1-like LMPs
(full length nucleic acid sequences can be found in the
Appendix using the sequence codes in Table 3)

| Seq ID | Sequence name | Species | Function | ORF position |
|---|---|---|---|---|
| 7 | pcw4-1 | Brassica napus | WRINKLED 1 transcription factor involved in glycolysis/oil biosynthesis | 3-1241 |
| 10 | pcw5a-1 | Brassica napus | WRINKLED 1 transcription factor involved in glycolysis/oil biosynthesis | 3-1232 |
| 13 | pcw5b-1 | Brassica napus | WRINKLED 1 transcription factor involved in glycolysis/oil biosynthesis | 3-1250 |
| 16 | BnWRI01 | Brassica napus | WRINKLED 1 transcription factor involved in glycolysis/oil biosynthesis | 62-1306 |
| 19 | BnWRI08 | Brassica napus | Ovule development protein | 126-1235 |
| 22 | psw2 | Glycine max | Ovule development protein | 206-1753 |
| 25 | psw6 | Glycine max | Aintegumenta-like protein | 85-1668 |
| 28 | GmWRI02 | Glycine max | Ovule development protein | 142-1680 |
| 31 | GmWRI03 | Glycine max | Aintegumenta-like protein | 235-2385 |
| 34 | GmWRI05 | Glycine max | Aintegumenta-like protein | 1-1995 |
| 37 | GmWRI08 | Glycine max | Aintegumenta-like protein | 1-1989 |
| 40 | OsWRI01 | Oryza sativa | Ap2/EREBP transcription factor | 49-1386 |
| 43 | OsWRI07 | Oryza sativa | Aintegumenta-like protein | 478-1578 |
| 46 | OsWRI03 | Oryza sativa | Ovule development protein aintegumenta | 71-1996 |
| 49 | TaWRI01 | Triticum aestivum | Ovule development protein | 603-1727 |
| 52 | GmWRI01-1 | Glycine max | Ovule development protein | 175-1764 |
| 55 | GmWRI11 | Glycine max | Ovule development protein | 120-2027 |

Example 7

Identification of Genes of Interest by Screening Expression Libraries with Antibodies c-DNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins can be used to produce specific antibodies for example by using standard techniques for rabbit immunization. Antibodies are affinity purified using a Ni-NTA column saturated with the recombinant antigen as described by Gu et al. (1994, BioTechniques 17:257-262). The antibody can then be used to screen expression cDNA libraries to identify homologous or heterologous genes via an immunological screening (Sambrook et al. 1989, Molecular Cloning: A Laboratory Manual", Cold Spring Harbor Laboratory Press or Ausubel et al. 1994, "Current Protocols in Molecular Biology", John Wiley & Sons).

Example 8

Northern-Hybridization

For RNA hybridization, 20 μg of total RNA or 1 μg of poly-(A)+ RNA is separated by gel electrophoresis in 1.25% agarose gels using formaldehyde as described in Amasino (1986, Anal. Biochem. 152:304), transferred by capillary attraction using 10×SSC to positively charged nylon membranes (Hybond N+, Amersham, Braunschweig), immobilized by UV light and pre-hybridized for 3 hours at 68° C. using hybridization buffer (10% dextran sulfate w/v, 1 M NaCl, 1% SDS, 100 μg/ml of herring sperm DNA). The labeling of the DNA probe with the Highprime DNA labeling kit (Roche, Mannheim, Germany) is carried out during the pre-hybridization using alpha-32P dCTP (Amersham, Braunschweig, Germany). Hybridization is carried out after addition of the labeled DNA probe in the same buffer at 68° C. overnight. The washing steps are carried out twice for 15 minutes using 2×SSC and twice for 30 minutes using 1×SSC, 1% SDS at 68° C. The exposure of the sealed filters is carried out at −70° C. for a period of 1 day to 14 days.

Example 9

DNA Sequencing and Computational Functional Analysis cDNA libraries can be used for DNA sequencing according to standard methods, in particular by the chain termination method using the ABI PRISM Big Dye Terminator Cycle Sequencing Ready Reaction Kit (Perkin-Elmer, Weiterstadt, Germany). Random sequencing can be carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA can be prepared from overnight grown *E. coli* cultures grown in Luria-Broth medium containing ampicillin (See Sambrook et al. (1989, Cold Spring Harbor Laboratory Press: ISBN 0-87969-309-6) on a Qiagene DNA preparation robot (Qiagen, Hilden) according to the manufacturer's protocols). Sequences can be processed and annotated using the software package EST-MAX commercially provided by Bio-Max (Munich, Germany). The program incorporates bioinformatics methods important for functional and structural characterization of protein sequences. For reference see pedant.mips.biochem.mpg.de.website.

The most important algorithms incorporated in Genomax and Pedant Pro are: FASTA: Very sensitive protein sequence database searches with estimates of statistical significance (Pearson W. R., 1990, Rapid and sensitive sequence comparison with FASTP and FASTA. Methods Enzymol. 183:63-98); BLAST: Very sensitive protein sequence database searches with estimates of statistical significance (Altschul S. F. et al., Basic local alignment search tool. J. Mol. Biol. 215:403-410); PREDATOR: High-accuracy secondary structure prediction from single and multiple sequences (Frishman & Argos 1997, 75% accuracy in protein secondary structure prediction. Proteins 27:329-335); CLUSTALW: Multiple sequence alignment (Thompson, J. D. et al., 1994, CLUSTAL W: improving the sensitivity of progressive multiple sequence alignment through sequence weighting, positions-specific gap penalties and weight matrix choice, Nucleic Acids Res. 22:4673-4680); TMAP: Transmembrane region prediction from multiply aligned sequences (Persson B. & Argos P. 1994, Prediction of transmembrane segments in proteins utilizing multiple sequence alignments, J. Mol. Biol. 237:182-192); ALOM2: Transmembrane region prediction from single sequences (Klein P., Kanehisa M., and DeLisi C. 1984, Prediction of protein function from sequence properties: A discriminant analysis of a database. Biochim. Biophys. Acta 787:221-226. Version 2 by Dr. K. Nakai); PROSEARCH: Detection of PROSITE protein sequence patterns (Kolakowski L. F. Jr. et al., 1992, ProSearch: fast searching of protein sequences with regular expression patterns related to protein structure and function. Biotechniques 13:919-921); BLIMPS: Similarity searches against a database of ungapped blocks (Wallace & Henikoff 1992, PATMAT:A searching and extraction program for sequence, pattern and block queries and databases, CABIOS 8:249-254. Written by Bill Alford); PFAM and BLOCKS searches of protein motifs and domains.

Example 10

Plasmids for Plant Transformation

For plant transformation binary vectors such as pBinAR can be used (Höfgen & Willmitzer, 1990, Plant Sci. 66:221-230). Construction of the binary vectors can be performed by ligation of the cDNA in sense or antisense orientation into the T-DNA. 5-prime to the cDNA a plant promoter activates transcription of the cDNA. A polyadenylation sequence is located 3'-prime to the cDNA. Tissue-specific expression can be achieved by using a tissue specific promoter. For example, seed-specific expression can be achieved by cloning the napin or LeB4 or USP promoter 5-prime to the cDNA. Also, any other seed specific promoter element can be used. For constitutive expression within the whole plant the CaMV 35S promoter can be used. The expressed protein can be targeted to a cellular compartment using a signal peptide, for example for plastids, mitochondria or endoplasmic reticulum (Kermode, 1996, Crit. Rev. Plant Sci. 15:285-423). The signal peptide is cloned 5-prime in frame to the cDNA to achieve subcellular localization of the fusion protein.

Further examples for plant binary vectors are the pBPS-GB1, pSUN2-GW, or pBPS-GB047 vectors into which the LMP gene candidates are cloned. These binary vectors contain an antibiotic resistance gene driven under the control of the AtAct2-I promoter and a USP seed-specific promoter or the PtxA promoter (See Appendix for sequence) in front of the candidate gene with the NOSpA terminator or the OCS terminator. Partial or full-length LMP cDNA is cloned into the multiple cloning site of the plant binary vector in sense or antisense orientation behind the USP seed-specific or PtxA promoters. The recombinant vector containing the gene of interest is transformed into Top10 cells (Invitrogen) using standard conditions. Transformed cells are selected for on LB agar containing 50 µg/ml kanamycin grown overnight at 37° C. Plasmid DNA is extracted using the QIAprep Spin Miniprep Kit (Qiagen) following manufacturer's instructions. Analysis of subsequent clones and restriction mapping is performed according to standard molecular biology techniques (Sambrook et al., 1989, Molecular Cloning, A Laboratory Manual. 2nd Edition. Cold Spring Harbor Laboratory Press. Cold Spring Harbor, N.Y.).

Example 11

Agrobacterium Mediated Plant Transformation

Agrobacterium mediated plant transformation with the LMP nucleic acids described herein can be performed using standard transformation and regeneration techniques (Gelvin & Schilperoort, Plant Molecular Biology Manual, 2nd ed. Kluwer Academic Publ., Dordrecht 1995 in Sect., Ringbuc Zentrale Signatur:BT11-P; Glick, Bernard R. and Thompson, John E. Methods in Plant Molecular Biology and Biotechnology, S. 360, CRC Press, Boca Raton 1993). For example, Agrobacterium mediated transformation can be performed using the GV3 (pMP90) (Koncz & Schell, 1986, Mol. Gen. Genet. 204:383-396) or LBA4404 (Clontech) Agrobacterium tumefaciens strain.

Arabidopsis thaliana can be grown and transformed according to standard conditions (Bechtold, 1993, Acad. Sci. Paris. 316:1194-1199; Bent et al., 1994, Science 265:1856-1860). Additionally, rapeseed can be transformed with the LMP nucleic acids of the present invention via cotyledon or hypocotyl transformation (Moloney et al., 1989, Plant Cell Report 8:238-242; De Block et al. 1989, Plant Physiol. 91:694-701). Use of antibiotics for Agrobacterium and plant selection depends on the binary vector and the Agrobacterium strain used for transformation. Rapeseed selection is normally performed using a selectable plant marker. Additionally, Agrobacterium mediated gene transfer to flax can be performed using, for example, a technique described by Mlynarova et al. (1994, Plant Cell Report 13:282-285).

The Arabidopsis WRI1 or WRI1-like gene was cloned into a binary vector and expressed under the PtxA promoter (the promoter of the Pisum sativum PtxA gene, see Appendix), which is a promoter active in virtually all plant tissues. However, in seeds and flowers, there is no expression activity detectable by GUS staining and low expression activity detectable with the more sensitive method of RT-PCR (Song et al., 2004, PF 55368-2 US). Only in plant lines comprising multiple copies of a transgenic ptxA-promoter/GUS expression construct some expression could be detected in part of the flowers and the siliques (for more details see Song et al., 2004, PF 55368-2 US). Alternatively, the superpromoter, which is a constitutive promoter (Stanton B. Gelvin, U.S. Pat. Nos. 5,428,147 and 5,217,903) or seed-specific promoters like USP (unknown seed protein) from Vicia faba (Baeumlein et al., 1991, Mol. Gen. Genetics 225:459-67), or the legumin B4 promoter (LeB4; Baeumlein et al., 1992, Plant J. 2:233-239), as well as promoters conferring seed-specific expression in monocot plants like maize, barley, wheat, rye, and rice etc. were used. The Arabidopsis AHAS (AtAHAS) gene was used as a selectable marker in these constructs. FIG. 1 shows the scheme of a binary vector construct containing an Arabidopsis WRI1-like sequence from Brassica napus.

Transformation of soybean can be performed using for example a technique described in EP 0424 047, U.S. Pat. No. 5,322,783 (Pioneer Hi-Bred International) or in EP 0397 687, U.S. Pat. No. 5,376,543, or U.S. Pat. No. 5,169,770 (University Toledo), or by any of a number of other transformation procedures known in the art. Soybean seeds are surface sterilized with 70% ethanol for 4 minutes at room temperature with continuous shaking, followed by 20% (v/v) CLOROX supplemented with 0.05% (v/v) TWEEN for 20 minutes with continuous shaking. Then the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

The method of plant transformation is also applicable to *Brassica napus* and other crops. In particular, seeds of canola are surface sterilized with 70% ethanol for 4 minutes at room temperature with continuous shaking, followed by 20% (v/v) CLOROX supplemented with 0.05% (v/v) TWEEN for 20 minutes, at room temperature with continuous shaking. Then, the seeds are rinsed 4 times with distilled water and placed on moistened sterile filter paper in a Petri dish at room temperature for 18 hours. The seed coats are removed and the seeds are air dried overnight in a half-open sterile Petri dish. During this period, the seeds lose approximately 85% of their water content. The seeds are then stored at room temperature in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature and resuspended in MS (Murashige & Skoog, 1962, Physiol. Plant. 15:473-497) medium supplemented with 100 mM acetosyringone. Bacteria cultures are incubated in this pre-induction medium for 2 hours at room temperature before use. The axis of soybean zygotic seed embryos at approximately 44% moisture content are imbibed for 2 hours at room temperature with the pre-induced *Agrobacterium* suspension culture. (The imbibition of dry embryos with a culture of *Agrobacterium* is also applicable to maize embryo axes). The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/l carbenicillin or 300 mg/l cefotaxime to kill the agrobacteria. The liquid medium is used to moisten the sterile filter paper. The embryos are incubated during 4 weeks at 25° C., under 440 µmol m$^{-2}$s$^{-1}$ and 12 hours photoperiod. Once the seedlings have produced roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 440 µmol m$^{-2}$s$^{-1}$ light intensity and 12 h photoperiod for about 80 days.

Samples of the primary transgenic plants (T$_0$) are analyzed by PCR to confirm the presence of T-DNA. These results are confirmed by Southern hybridization wherein DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labeled probe by PCR as recommended by the manufacturer.

Figure 2:
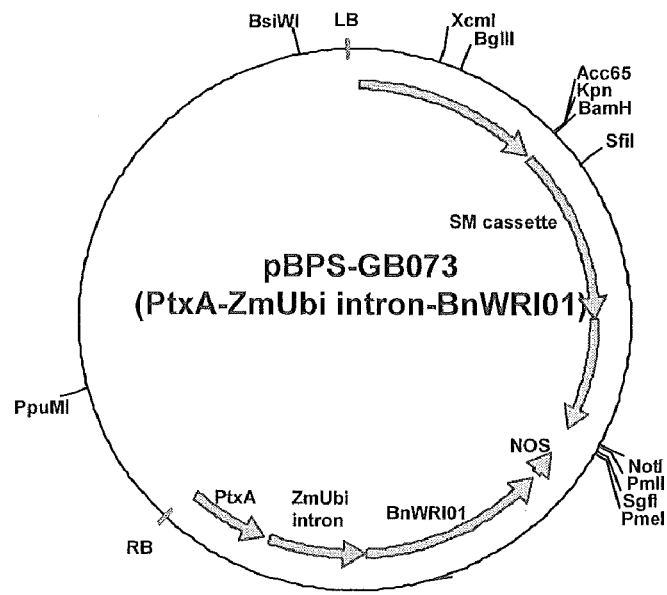
FIG. 2 is a map of the ptxA promoter::ZmUbiquitin intron::BnWRI01 chimeric construct (PtxAZmUbi intron-Bn-WRI01). The plasmid comprises an expression construct containing a ptxA promoter (ptxA) operatively linked to maize Ubiquitin intron (ZmUbi intron), *Brassica napus* WRINKLED 1 (BnWRI01), and 3' untranslated region and termination derived from the nopaline synthase gene (NOS). SM cassette stands for a selectable marker cassette.

As an example for monocot transformation, the construction of ptxA promoter in combination with maize Ubiquitin intron and WRI1 or WRI1-like nucleic acid molecules is described. The PtxA-WRI1 ortholog gene construct in pUC is digested with PacI and XmaI. pBPSMM348 is digested with PacI and XmaI to isolate maize Ubiquitin intron (ZmUbi intron) followed by electrophoresis and the QIAEX II Gel Extraction Kit (cat#20021). The ZmUbi intron is ligated into the PtxA-WRI1 or WRI1-like nucleic acid molecule in pUC to generate pUC based PtxA-ZmUbi intron-WRI1 or WRI1-like nucleic acid molecule construct followed by restriction enzyme digestion with AfeI and PmeI. PtxA-ZmUbi intron WRI1 or WRI1-like gene cassette is cut out of a Seaplaque low melting temperature agarose gel (SeaPlaque® GTG® Agarose catalog No. 50110) after electrophoresis. A monocotyledonous base vector containing a selectable marker cassette (Monocot base vector) is digested with PmeI. The WRI1 or WRI1-like nucleic acid molecule expression cassette containing ptxA promoter-ZmUbi intron is ligated into the Monocot base vector to generate PtxA-ZmUbi intron-Bn-WRI01 construct (FIG. 2). Subsequently, the PtxA-ZmUbi intron-WRI1 or WRI1-like nucleic acid molecule construct is transformed into a recombinant LBA4404 strain containing pSB1 (super vir plasmid) using electroporation following a general protocol in the art. *Agrobacterium*-mediated transformation in maize is performed using immature embryo following a protocol described in U.S. Pat. No. 5,591,616. An imidazolinoneherbicide selection is applied to obtain transgenic maize lines. In GUS expression experiments using the ptxA promoter::ZmUbi intron in maize strong expression was described in embryonic calli and roots (Song et al., 2004, PF 55368-2 US).

In general, a rice (or other monocot) WRI1 gene or WRI1-like gene under a plant promoter like PtxA could be transformed into corn, or another crop plant, to generate effects of monocot WRI1 genes in other monocots, or dicot WRI1 genes in other dicots, or monocot genes in dicots, or vice versa. The plasmids containing these WRI1 or WRI1-like coding sequences, 5' of a promoter and 3' of a terminator would be constructed in a manner similar to those described for construction of other plasmids herein.

Example 12

In Vivo Mutagenesis

In vivo mutagenesis of microorganisms can be performed by incorporation and passage of the plasmid (or other vector) DNA through *E. coli* or other microorganisms (e.g. *Bacillus* spp. or yeasts such as *Saccharomyces cerevisiae*) that are impaired in their capabilities to maintain the integrity of their genetic information. Typical mutator strains have mutations in the genes for the DNA repair system (e.g., mutHLS, mutD, mutT, etc.; for reference, see Rupp, 1996, DNA repair mechanisms, in: *Escherichia coli* and *Salmonella*, p. 2277-2294, ASM: Washington.) Such strains are well known to those skilled in the art. The use of such strains is illustrated, for example, in Greener and Callahan, 1994, Strategies 7:32-34. Transfer of mutated DNA molecules into plants is preferably done after selection and testing in microorganisms. Transgenic plants are generated according to various examples within the exemplification of this document.

Example 13

Assessment of the mRNA Expression and Activity of a Recombinant Gene Product in the Transformed Organism The activity of a recombinant gene product in the transformed host organism can be measured on the transcriptional and/or on the translational level. A useful method to ascertain the level of transcription of the gene (an indicator of the amount of mRNA available for translation to the gene product) is to perform a Northern blot (for reference see, for example, Ausubel et al., 1988, Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from plant cells, tissues, or organs by several methods, all well-known in the art, such as that described in Bormann et al. (1992, Mol. Microbiol. 6:317-326).

To assess the presence or relative quantity of protein translated from this mRNA, standard techniques, such as a Western blot, may be employed (see, for example, Ausubel et al., 1988, Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label, which may be readily detected. The presence and quantity of label observed indicates the presence and quantity of the desired mutant protein present in the cell.

The activity of LMPs that bind to DNA can be measured by several well-established methods, such as DNA band-shift assays (also called gel retardation assays). The effect of such LMP on the expression of other molecules can be measured using reporter gene assays (such as that described in Kolmar H. et al., 1995, EMBO J. 14:3895-3904 and references cited therein). Reporter gene test systems are well known and established for applications in both prokaryotic and eukaryotic cells, using enzymes such as beta-galactosidase, green fluorescent protein, and several others.

The determination of activity of lipid metabolism membrane-transport proteins can be performed according to techniques such as those described in Gennis R. B. (1989 Pores, Channels and Transporters, in Biomembranes, Molecular Structure and Function, Springer: Heidelberg, pp. 85-137, 199-234 and 270-322).

Example 14

In Vitro Analysis of the Function of *Arabidopsis thaliana, Brassica napus, Glycine max, Oryza sativa,* or *Triticum aestivum* WRI1 and WRI1-Like Genes in Transgenic Plants The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon & Webb, 1979, Enzymes. Longmans: London; Fersht, (1985) Enzyme Structure and Mechanism. Freeman: New York; Walsh (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, 3rd ed. Academic Press: New York; Bisswanger, H., (1994) Enzymkinetik, 2nd ed. VCH: Weinheim (ISBN 3527300325); Bergmeyer, H. U., Bergmeyer, J., Graβl, M., eds. (1983-1986) Methods of Enzymatic Analysis, 3rd ed., vol. I-XII, Verlag Chemie: Weinheim; and Ullmann's Encyclopedia of Industrial Chemistry (1987) vol. A9, Enzymes. VCH: Weinheim, p. 352-363.

Example 15

Figure 3:
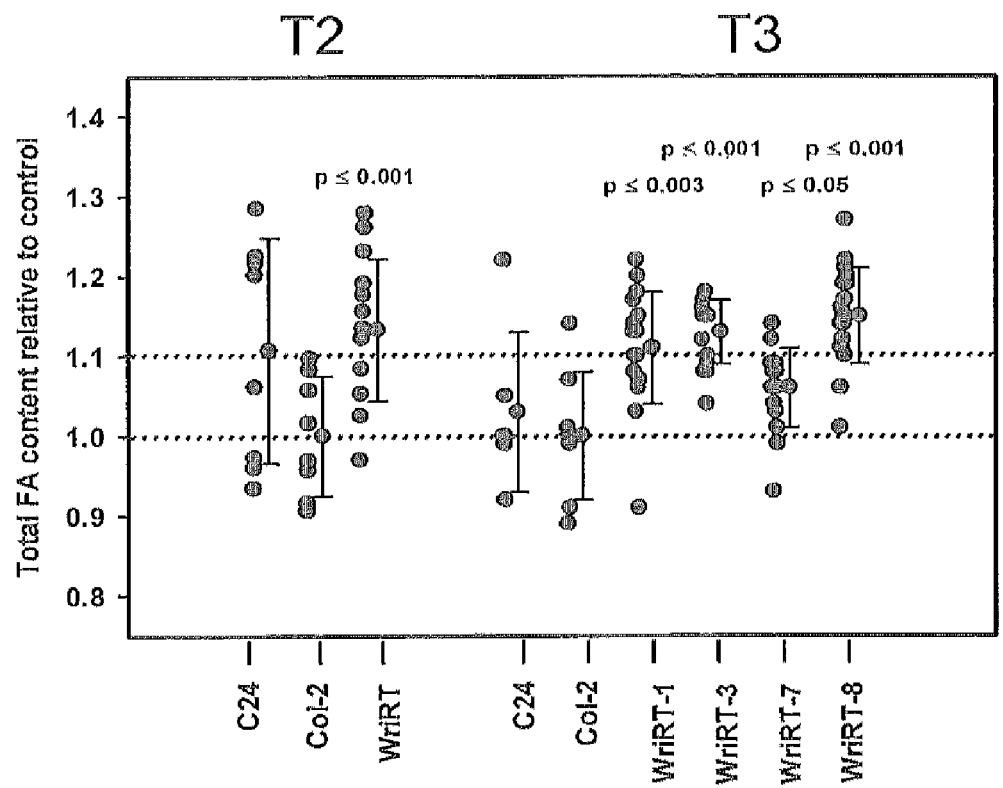
FIG. 3 is a graph showing total seed oil content in *A. thaliana* plants in T2 and T3 seed generation overexpressing WRI. Each circle represents the value obtained with one individual plant, and independent transgenic events are shown. Statistical analysis was by t-Test. The abbreviations, are defined as follows: C24, Columbia24; Col-2, Columbia 2.
Figure 4:
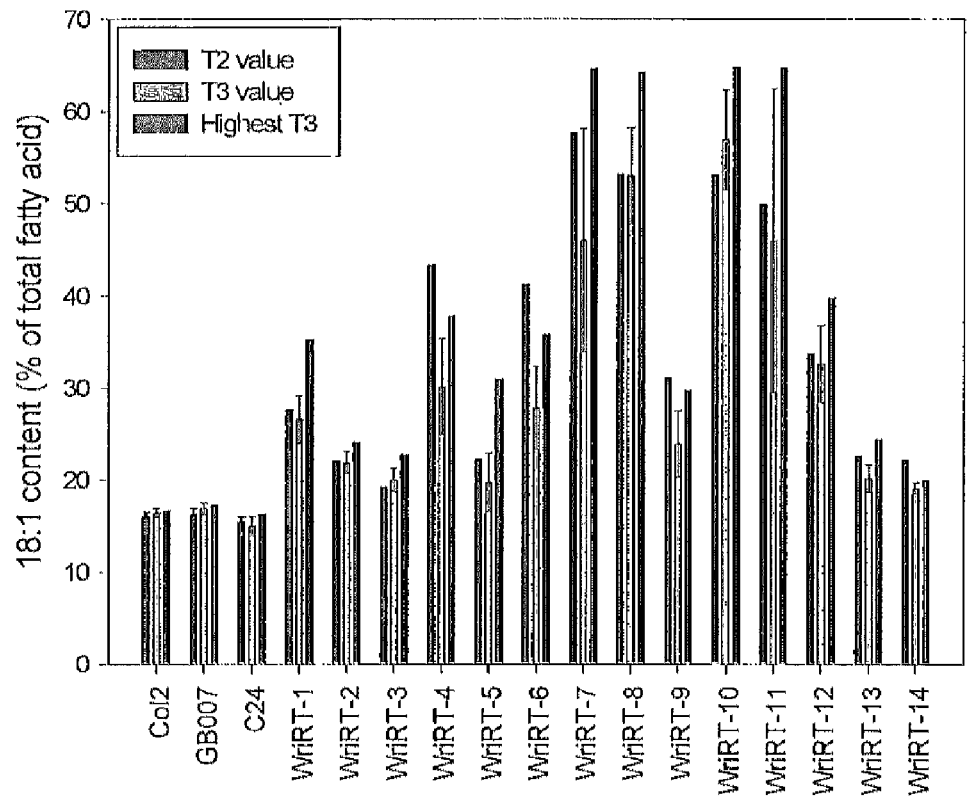
FIG. 4 is a graph showing oleic acid (C18:1) levels in *A. thaliana* plants in the T2 and T3 seed generation overexpressing WRI. Col2, wild type Columbia-2, GB007, empty vector control in Columbia 2 genetic background; C24, Columbia 24, WriRT, independent transgenic events of PtxA::WRI1 overexpressors. Each bar shows the average obtained with 20 plants each.

Analysis of the Impact of Recombinant Proteins on the Production of a Desired Seed Storage Compound Seeds from transformed *Arabidopsis thaliana* plants were analyzed by gas chromatography (GC) for total oil content and fatty acid profile. GC analysis reveals that *Arabidopsis* plants transformed with pBPS-GB047 containing Ptxa promoter driving the *Arabidopsis* WRI1 gene and the AHAS gene as selectable marker show an increase in total seed oil content by 10-15% compared with Columbia-2 in both segregating T2 and homozygous T3 seed generation (FIG. 3). The total seed protein level was virtually the same level as compared with a control plant (data not shown). *Arabidopsis* PtxA::WRI1 overexpressors (AtWRI01) showed an increased percentage of total seed oil content from about 35% in Columbia wild type and PtxA empty vector control to about 40% in T2 and T3 seeds of transgenic lines. FIG. 4 shows the effect of PtxA::WRI1 on the content of oleic acid (18:1) in seeds. There is a highly significant increase in some of the transgenic lines, as compared to Columbia-2 (the genetic background), GB007 (the empty vector control), and Columbia-24 (a high oil control used in the experiment). The relative amount of oleic acid increased from about 18% in controls to 63-65% in some of the transgenic WRI1 overexpressors. The effect on the oleic acid increase appears to be very stable in T2 and T3 seed generations. We conclude from the correlation between the increase in total seed oil content and the increased percentage in oleic acid in the T2 and T3 seed generation as shown in FIGS. 3 and 4 that the trait is genetically inheritable.

Figure 5:
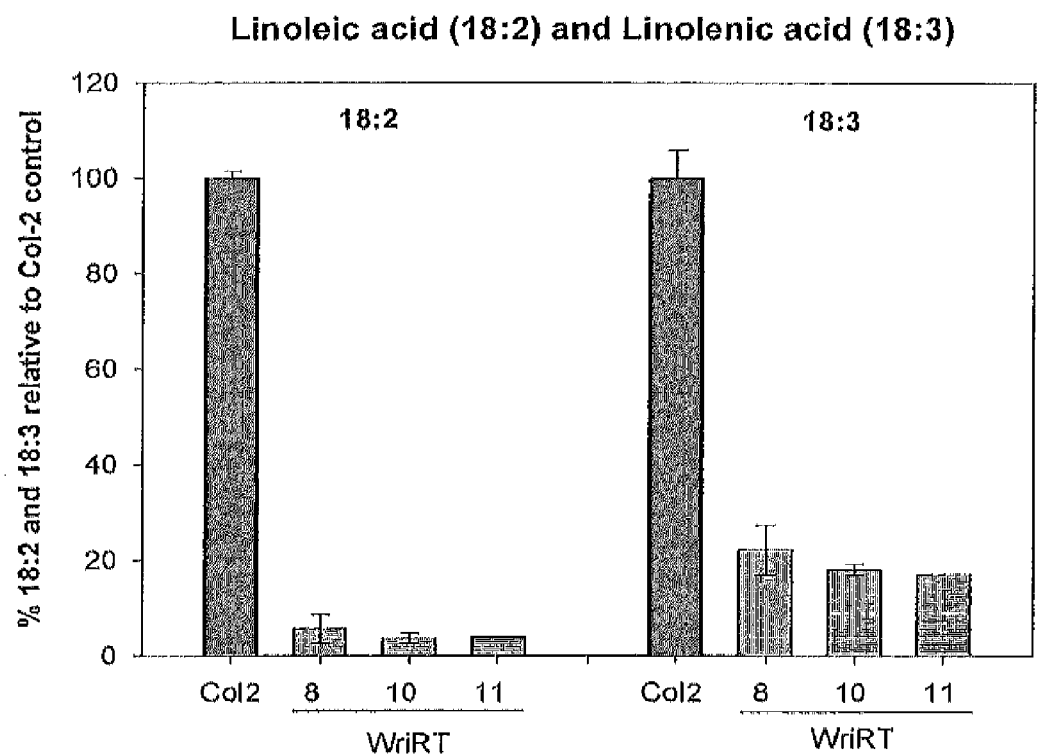
FIG. 5 is a graph showing linoleic and linolenic acid levels in homozygous *A. thaliana* plants in T2 and T3 seed generation overexpressing WRI. Each bar shows the average obtained with 20 plants. C18:2 content was reduced by 95%, and C18:3 content was reduced by 80% in homozygous *A. thaliana* plants in T3 seed generation overexpressing WRI. The abbreviations used are defined as follows: Col2, *Arabidopsis* ecotype Columbia-2; WRI1-8, 10, 11, independent transgenic events of PtxA::WRI1.
Figure 6:
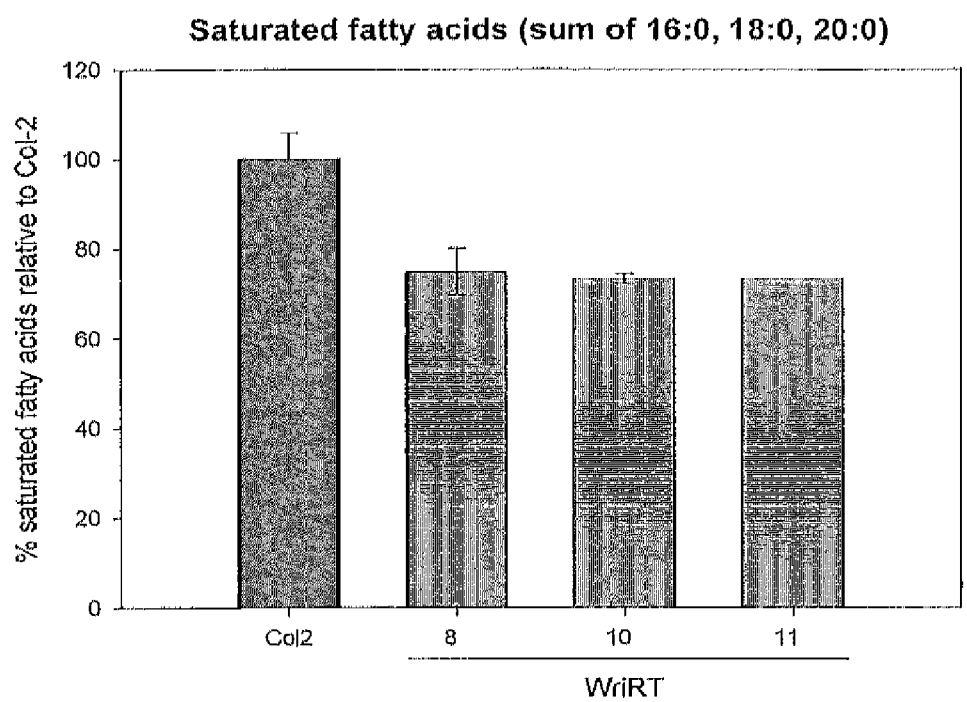
FIG. 6 is a graph showing saturated fatty acid levels in homozygous *A. thaliana* overexpressing WRI: Homozygous T3 seeds show 30% reduction in saturates in WRI1 overexpressors. The abbreviations used are defined as follows: Col2, *Arabidopsis* ecotype Columbia-2; WRI1-8,10,11, independent transgenic events of PtxA::WRI1.

The increase in the percentage oleic acid in seeds is accompanied with a significant reduction in the relative amount of linoleic and linolenic acid (FIG. 5). Linoleic acid in transgenic seeds was less than 5% of the wild type content and linolenic acid was 20% and less relative to the wild type content. In parallel, the relative amount of saturated fatty acids (sum of 16:0, 18:0, 20:0) decreased in transgenic seeds by at least 20% as compared to the wild type (FIG. 6).

The effect of other promoter/WRI1 gene combinations was tested. Transgenic plants expressing WRI1 under the control of the seed-specific promoter LeB4 did not show any detectable effect on the fatty acid composition in seeds. The results suggest that WRI1 overexpression with a promoter like PtxA allows the manipulation of total seed oil content and of the fatty acid composition particularly oleic acid, linoleic acid, and linolenic acid.

The effect of the genetic modification in plants on a desired seed storage compound (such as a sugar, lipid, or fatty acid) can be assessed by growing the modified plant under suitable conditions and analyzing the seeds or any other plant organ for increased production of the desired product (i.e., a lipid or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullman, 1985, Encyclopedia of Industrial Chemistry, vol. A2, pp. 89-90 and 443-613, VCH: Weinheim; Fallon et al., 1987, Applications of HPLC in Biochemistry in: Laboratory Techniques in Biochemistry and Molecular Biology, vol. 17; Rehm et al., 1993, Product recovery and purification, Biotechnology, vol. 3, Chapter III, pp. 469-714, VCH: Weinheim; Belter, P. A. et al., 1988 Bioseparations: downstream processing for biotechnology, John Wiley & Sons; Kennedy & Cabral, 1992, Recovery processes for biological materials, John Wiley and Sons; Shaeiwitz & Henry, 1988, Biochemical separations in: Ulmann's Encyclopedia of Industrial Chemistry, Separation and purification techniques in biotechnology, vol. B3, Chapter 11, pp. 1-27, VCH: Weinheim; and Dechow F. J. 1989).

Besides the above-mentioned methods, plant lipids are extracted from plant material as described by Cahoon et al. (1999, Proc. Natl. Acad. Sci. USA 96, 22:12935-12940) and Browse et al. (1986, Anal. Biochemistry 442:141-145). Qualitative and quantitative lipid or fatty acid analysis is described in Christie, William W., Advances in Lipid Methodology. Ayr/Scotland:Oily Press.—(Oily Press Lipid Library; Christie, William W., Gas Chromatography and Lipids. A Practical Guide—Ayr, Scotland:Oily Press, 1989 Repr. 1992.—IX, 307 S.—(Oily Press Lipid Library; and "Progress in Lipid Research, Oxford: Pergamon Press, 1 (1952)-16 (1977) Progress in the Chemistry of Fats and Other Lipids CODEN.

Unequivocal proof of the presence of fatty acid products can be obtained by the analysis of transgenic plants following standard analytical procedures: GC, GC-MS, or TLC as described by Christie and references therein (1997 in: Advances on Lipid Methodology 4th ed.: Christie, Oily Press, Dundee, pp. 119-169; 1998). Detailed methods are described for leaves by Lemieux et al. (1990, Theor. Appl. Genet. 80:234-240) and for seeds by Focks & Benning (1998, Plant Physiol. 118:91-101).

Positional analysis of the fatty acid composition at the sn-1, sn-2 or sn-3 positions of the glycerol backbone is determined by lipase digestion (See, e.g., Siebertz & Heinz, 1977, Z. Naturforsch. 32c:193-205, and Christie 1987, Lipid Analysis 2nd Edition, Pergamon Press, Exeter, ISBN 0-08-023791-6).

Total seed oil levels can be measured by any appropriate method. Quantitation of seed oil contents is often performed with conventional methods, such as near infrared analysis (NIR) or nuclear magnetic resonance imaging (NMR). NIR spectroscopy has become a standard method for screening seed samples whenever the samples of interest have been amenable to this technique. Samples studied include canola, soybean, maize, wheat, rice, and others. NIR analysis of single seeds can be used (See, e.g., Velasco et al., 'Estimation of seed weight, oil content and fatty acid composition in intact single seeds of rapeseed (*Brassica napus* L.) by near-infrared reflectance spectroscopy,' Euphytica, Vol. 106, 1999, pp. 79-85). NMR has also been used to analyze oil content in seeds (See, e.g., Robertson & Morrison, Journal of the American Oil Chemists Society, 1979, Vol. 56, 1979, pp. 961-964, which is herein incorporated by reference in its entirety).

A typical way to gather information regarding the influence of increased or decreased protein activities on lipid and sugar biosynthetic pathways is for example via analyzing the carbon fluxes by labeling studies with leaves or seeds using $^{14}C$-acetate or $^{14}C$-pyruvate (See, e.g., Focks & Benning, 1998, Plant Physiol. 118:91-101; Eccleston & Ohlrogge, 1998, Plant Cell 10:613-621). The distribution of $^{14}C$ into lipids and aqueous soluble components can be determined by liquid scintillation counting after the respective separation (for example, on TLC plates) including standards like $^{14}C$-sucrose and $^{14}C$-malate (Eccleston & Ohlrogge, 1998, Plant Cell 10:613-621).

Material to be analyzed can be disintegrated via sonication, glass milling, liquid nitrogen, and grinding or via other applicable methods. The material has to be centrifuged after disintegration. The sediment is re-suspended in distilled water, heated for 10 minutes at 100° C., cooled on ice, and centrifuged again, followed by extraction in 0.5 M sulfuric acid in methanol containing 2% dimethoxypropane for 1 hour at 90° C. leading to hydrolyzed oil and lipid compounds, resulting in transmethylated lipids. These fatty acid methyl esters are extracted in petrolether and finally subjected to GC analysis using a capillary column (Chrompack, WCOT Fused Silica, CP-Wax-52 CB, 25 m, 0.32 mm) at a temperature gradient between 170° C. and 240° C. for 20 minutes, and then 5 minutes at 240° C. The identity of resulting fatty acid methylesters is defined by the use of standards available form commercial sources (i.e., Sigma). In case of fatty acids where standards are not available, molecule identity is shown via derivatization and subsequent GC-MS analysis. For example, the localization of triple bond fatty acids is shown via GC-MS after derivatization via 4,4-Dimethoxy-oxazolin-Derivaten (Christie, Oily Press, Dundee, 1998).

A common standard method for analyzing sugars, especially starch, is published by Stitt et al. (1989, Methods Enzymol. 174:518-552). For other methods, see also Hartel et al. (1998, Plant Physiol. Biochem. 36:407-417) and Focks & Benning (1998, Plant Physiol. 118:91-101).

For the extraction of soluble sugars and starch, 50 seeds are homogenized in 500 µl of 80% (v/v) ethanol in a 1.5-ml polypropylene test tube and incubated at 70° C. for 90 minutes. Following centrifugation at 16,000 g for 5 minutes, the supernatant is transferred to a new test tube. The pellet is extracted twice with 500 µl of 80% ethanol. The solvent of the combined supernatants is evaporated at room temperature under a vacuum. The residue is dissolved in 50 µl of water, representing the soluble carbohydrate fraction. The pellet left from the ethanol extraction, which contains the insoluble carbohydrates including starch, is homogenized in 200 µA of 0.2 N KOH, and the suspension is incubated at 95° C. for 1 hour to dissolve the starch. Following the addition of 35 µl of 1 N acetic acid and centrifugation for 5 minutes at 16,000 g, the supernatant is used for starch quantification.

To quantify soluble sugars, 10 µl of the sugar extract is added to 990 of reaction buffer containing 100 mM imidazole, pH 6.9, 5 mM $MgCl_2$, 2 mM NADP, 1 mM ATP, and 2 units 2 $ml^{-1}$ of Glucose-6-P-dehydrogenase. For enzymatic determination of glucose, fructose and sucrose, 4.5 units of hexokinase, 1 unit of phosphoglucoisomerase, and 2 µl of a saturated fructosidase solution are added in succession. The production of NADPH is photometrically monitored at a wavelength of 340 nm. Similarly, starch is assayed in 30 µl of the insoluble carbohydrate fraction with a kit from Boehringer Mannheim.

An example for analyzing the protein content in leaves and seeds can be found in Bradford (1976, Anal. Biochem. 72:248-254). For quantification of total seed protein, 15-20 seeds are homogenized in 250 µl of acetone in a 1.5-ml polypropylene test tube. Following centrifugation at 16,000 g, the supernatant is discarded, and the vacuum-dried pellet is resuspended in 250 µl of extraction buffer containing 50 mM Tris-HCl, pH 8.0, 250 mM NaCl, 1 mM EDTA, and 1% (w/v) SDS. Following incubation for 2 hours at 25° C., the homogenate is centrifuged at 16,000 g for 5 minutes, and 200 ml of the supernatant will be used for protein measurements. In the assay, γ-globulin is used for calibration. For protein measurements, Lowry DC protein assay (Bio-Rad) or Bradford-assay (Bio-Rad) is used.

Enzymatic assays of hexokinase and fructokinase are performed spectrophotometrically according to Renz et al. (1993, Planta 190:156-165), of phosphogluco-isomerase, ATP-dependent 6-phosphofructokinase, pyrophosphate-dependent 6-phospho-fructokinase, Fructose-1,6-bisphosphate aldolase, triose phosphate isomerase, glyceral-3-P dehydrogenase, phosphoglycerate kinase, phosphoglycerate mutase, enolase, and pyruvate kinase are performed according to Burrell et al. (1994, Planta 194:95-101) and of UDP-Glucose-pyrophosphorylase according to Zrenner et al. (1995, Plant J. 7:97-107).

Intermediates of the carbohydrate metabolism, like Glucose-1-phosphate, Glucose-6-phosphate, Fructose-6-phosphate, Phosphoenolpyruvate, Pyruvate, and ATP are measured as described in Hartel et al. (1998, Plant Physiol. Biochem. 36:407-417) and metabolites are measured as described in Jelitto et al. (1992, Planta 188:238-244).

In addition to the measurement of the final seed storage compound (i.e., lipid, starch or storage protein) it is also possible to analyze other components of the metabolic pathways utilized for the production of a desired seed storage compound, such as intermediates and side-products, to determine the overall efficiency of production of the compound (Fiehn et al., 2000, Nature Biotech. 18:1447-1161). For example, yeast expression vectors comprising the nucleic acids disclosed herein, or fragments thereof, can be constructed and transformed into *Saccharomyces cerevisiae* using standard protocols. The resulting transgenic cells can then be assayed for alterations in sugar, oil, lipid, or fatty acid contents. Similarly, plant expression vectors comprising the nucleic acids disclosed herein, or fragments thereof, can be constructed and transformed into an appropriate plant cell such as *Arabidopsis*, soybean, rapeseed, rice, maize, wheat, *Medicago truncatula*, etc., using standard protocols. The resulting transgenic cells and/or plants derived there from can then be assayed for alterations in sugar, oil, lipid, or fatty acid contents.

Additionally, the sequences disclosed herein, or fragments thereof, can be used to generate knockout mutations in the genomes of various organisms, such as bacteria, mammalian cells, yeast cells, and plant cells (Girke at al., 1998, Plant J. 15:39-48). The resultant knockout cells can then be evaluated for their composition and content in seed storage compounds, and the effect on the phenotype and/or genotype of the mutation. Other methods of gene inactivation include those described in U.S. Pat. No. 6,004,804 and Puttaraju et al. (1999, Nature Biotech. 17:246-252).

Example 16

Purification of the Desired Product from Transformed Organisms

An LMP can be recovered from plant material by various methods well known in the art. Organs of plants can be separated mechanically from other tissue or organs prior to isolation of the seed storage compound from the plant organ. Following homogenization of the tissue, cellular debris is removed by centrifugation and the supernatant fraction containing the soluble proteins is retained for further purification of the desired compound. If the product is secreted from cells grown in culture, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin, while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey & Ollis, 1986, Biochemical Engineering Fundamentals, McGraw-Hill:New York).

The identity and purity of the isolated compounds may be assessed by techniques standard in the art. These include high-performance liquid chromatography (HPLC), spectroscopic methods, staining methods, thin layer chromatography, analytical chromatography such as high performance liquid chromatography, NIRS, enzymatic assay, or microbiologically. Such analysis methods are reviewed in: Patek et al. (1994, Appl. Environ. Microbiol. 60:133-140), Malakhova et al. (1996, Biotekhnologiya 11:27-32), Schmidt et al. (1998, Bioprocess Engineer 19:67-70), Ulmann's Encyclopedia of Industrial Chemistry (1996, Vol. A27, VCH: Weinheim, p. 89-90, p. 521-540, p. 540-547, p. 559-566, 575-581 and p. 581-587), and Michal G. (1999, Biochemical Pathways: An Atlas of Biochemistry and Molecular Biology, John Wiley and Sons; Fallon, A. et al. 1987, Applications of HPLC in Biochemistry in: Laboratory Techniques in Biochemistry and Molecular Biology, vol. 17).

Example 17

Screening for Increased Seed Size

Figure 7:
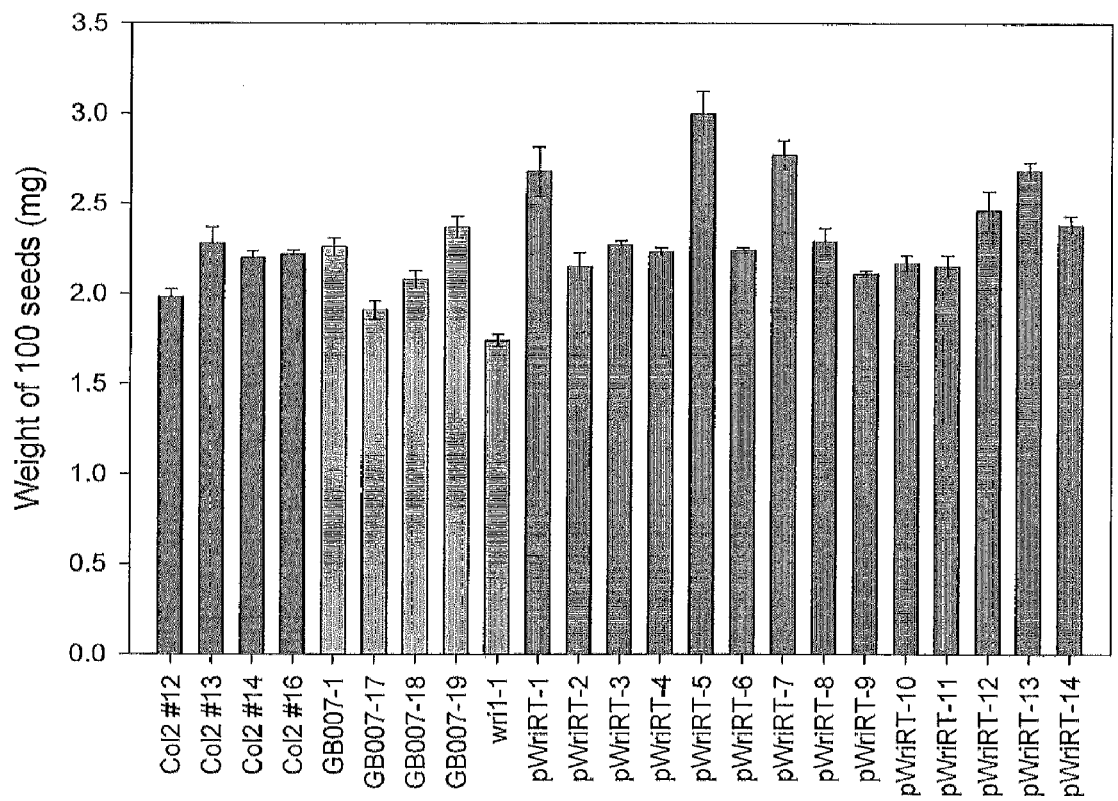
FIG. 7 is a graph showing seed weight in the *Arabidopsis* wri1 mutant and independent transgenic lines of *Arabidopsis* PtxA::WRI1 overexpressors in T2 seed generation. Values shown in the graph represent average values of seed weight obtained with seeds from a single plant. The abbreviations used are defined as follows: Col2, *Arabidopsis* ecotype Columbia-2; GB007, empty vector control.

The conditional expression of WRI1 and of the crop WRI1-like genes resulted in an increased seed size of the transgenic plants when compared to the wild type variety of the plants. Transgenic *Arabidopsis* plants expressing WRI1 under the control of the PtxA promoter were produced as described in Example 11 and found to produce seeds larger than the wild-type plants' seeds. This size increase was typically observed by using a microscope. In addition, the seed weight was found to be increased in PtxA::WRI1 overexpressors. For example, writ mutant seeds showed a 20% reduction in seed weight as compared with the wild type (FIG. 7). In the segregating T2 seed generation of the independent transgenic lines pWriRT-7 and pWriRT-5, the weight of 100 seeds was increased by 30 and 40%, respectively (FIG. 7). In homozygous T3 seeds the seed weight was increased up to 60% as compared with the empty vector control (data not shown). Increased seed weight was reflected in an increased seed size of WRI1 or WRI1-like gene overexpressors. Increased seed size leads to greater yield in many economically important crop plants. Therefore, increased seed size is one goal of genetically engineering and selection using WRI1 or WRI-like nucleic acid molecules as described in this application.

Example 18

Screening for Increased Root Length

In Vitro Root Analysis

For in vitro root analysis, square plates measuring 12 cm×12 cm were used. For each plate, 52 ml of MS media (0.5×MS salts, 0.5% sucrose, 0.5 g/L MES buffer, 1% Phytagar) without selection was used. Plates were allowed to dry in the sterile hood for one hour to reduce future condensation.

Seed aliquots were sterilized in glass vials with ethanol for 5 minutes, the ethanol was removed, and the seeds were allowed to dry in the sterile hood for one hour. Seeds were spotted in the plates using the Vacuseed Device (Lehle). After the seeds were spotted on the plates, the plates were wrapped with Ventwrap and placed vertically in racks in the dark at 4° C. for four days to stratify the seeds. The plates were transferred to a C5 Percival Growth Chamber and placed vertically. The growth chamber conditions were 23° C. day/21° C. night and 16 hour day/8 hour night.

Figure 8:
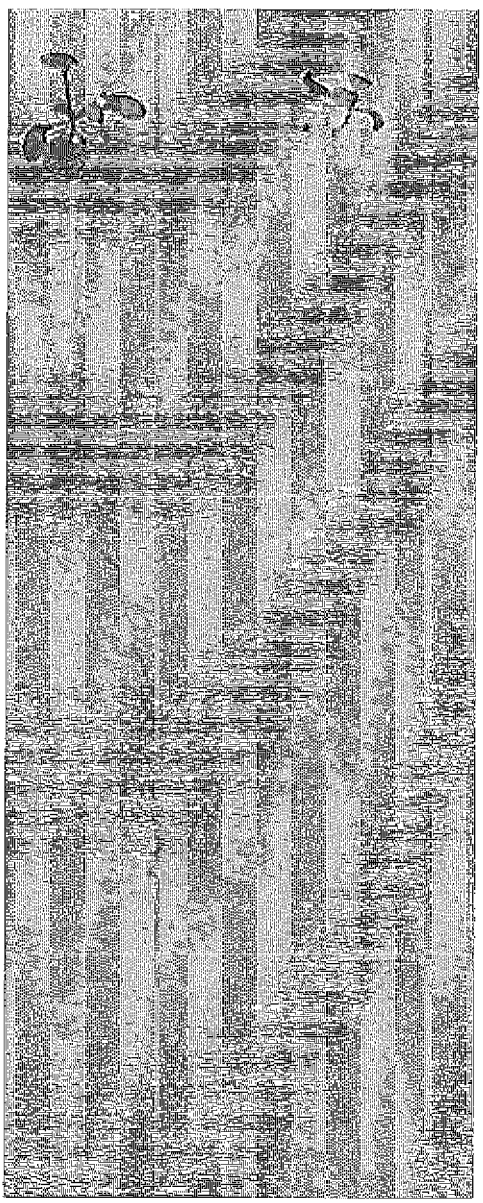
FIG. 8 is a photograph showing the root length of *Arabidopsis* wild-type Columbia-2 in comparison with the wri1 mutant after 14 days of growth on agar plates. The abbreviations used are defined as follows: WT, wild type Columbia 2; wri1, wrinkled 1 mutant.

For data collection a high resolution flat-bed scanner was used. Analysis of the roots was done using the WinRhizo software package. A comparison of the root length obtained with *Arabidopsis* wild type and the wri1 mutant indicated a 50% reduction in root length in wri1 mutants. This reduction in root length was found to be associated with a delayed germination and a reduced number of leaves at a defined time point of development as compared with the wild type (FIG. 8). Overexpressing WRI1 or WRI1-like genes in wild type background may improve seed germination, increase root length, and increase speed of leaf development and number of leaves. The latter may improve photosynthetic performance of plants resulting in increase yield of biomass and in increased amounts and/or size of seeds associated with increased amounts of seed storage compounds like oil, protein, and sugars.

Soil Root Analysis

For soil root analysis, seeds may be imbibed at 4° C. for 2 days in water and planted directly in soil with no selection. Deepots (Hummert D40) will be used with a saturated peat pellet (Jiffy 727) at the base and filled with water saturated Metromix. After planting, pots will be covered with plastic wrap to prevent drying. Plants may be grown using only water present at media preparation, as the water in the soil in these large pots is sufficient for 3 weeks of growth, and encourages rapid root growth. The plastic wrapping of the pots will be removed after 12 days and morphological data documented. At day 17, the aerial parts of the plant will be harvested, dried (65° C. for 2 days) and dry weight measured. To examine the roots, the peat pellet will be pushed towards the top of the pot to remove the soil and roots as a unit. The soil will then be separated from the roots in a tray and the maximum root length will be measured. Root length of all plants for all transgenic lines will be averaged and compared against the average of the wild type plants.

Those skilled in the art will recognize, or will be able to ascertain using no more than routine experimentation, many equivalents to the specific embodiments of the invention described herein. Such equivalents are intended to be encompassed by the claims to the invention disclosed and claimed herein.

---

We claim:

1. A method of producing a transgenic plant having an increase in seed weight comprising, transforming a plant cell with an expression vector comprising a lipid metabolism protein (LMP) nucleic acid and generating from the plant cell the transgenic plant, wherein the nucleic acid encodes a polypeptide that increases seed weight in the plant, and wherein the nucleic acid comprises a polynucleotide sequence selected from the group consisting of:
   a) the polynucleotide sequence of SEQ ID NO: 40 or SEQ ID NO: 41;
   b) a polynucleotide sequence encoding the polypeptide of SEQ ID NO: 42;
   c) a polynucleotide sequence having at least 90% sequence identity with the full-length LMP nucleic acid of a) or b) above;
   d) a polynucleotide sequence that encodes a polypeptide having at least 90% sequence identity with the amino acid sequence of SEQ ID NO: 42;
   e) a polynucleotide sequence that is complementary to the full-length LMP nucleic acid of a) or b) above; and
   f) a polynucleotide sequence that hybridizes under stringent conditions to the full-length LMP nucleic acid of a) or b) above, wherein the stringent conditions comprise hybridization in 6×SSC at about 45° C. followed by one or more washes in 0.2×SSC, 0.1% SDS at 50 to 65° C., wherein the seed weight is increased in the transgenic plant as compared to an untransformed wild type variety of the plant.

2. The method of claim 1, wherein the LMP nucleic acid comprises the polynucleotide sequence of SEQ ID NO: 40 or SEQ ID NO: 41.

3. The method of claim 1, wherein the LMP nucleic acid comprises a polynucleotide sequence encoding the polypeptide of SEQ ID NO: 42.

4. The method of claim 1, wherein the LMP nucleic acid comprises a polynucleotide sequence selected from the group consisting of:
   a) a polynucleotide sequence having at least 95% sequence identity with the polynucleotide sequence of a) or b) of claim 1; and
   b) a polynucleotide sequence that encodes a polypeptide having 95% sequence identity with the amino acid sequence of SEQ ID NO: 42.

5. The method of claim 1, wherein the LMP nucleic acid hybridizes under stringent conditions to the LMP nucleic acid of a) or b) of claim 1, wherein the stringent conditions comprise hybridization in 6×SSC at about 45° C. followed by one or more washes in 0.2×SSC, 0.1% SDS at 50 to 65° C.

6. The method of claim 1, wherein the LMP nucleic acid comprises a polynucleotide sequence complementary to the full-length LMP nucleic acid of a) or b) of claim 1.

7. The method of claim 1, wherein the LMP nucleic acid is operatively linked to a heterologous promoter selected from the group consisting of a seed-specific promoter, a root-specific promoter, and a non-tissue-specific promoter.

8. The method of claim 1, wherein the LMP nucleic acid is operatively linked to the ptxA promoter.

9. A method of increasing seed weight in a plant comprising, expressing a Lipid Metabolism Protein (LMP) nucleic acid in the plant, wherein the LMP nucleic acid comprises a polynucleotide sequence selected from the group consisting of:
   a) the polynucleotide sequence of SEQ ID NO: 40 or SEQ ID NO: 41;
   b) a polynucleotide sequence encoding the polypeptide of SEQ ID NO: 42;
   c) a polynucleotide sequence having at least 90% sequence identity with the full-length LMP nucleic acid of a) or b) above;
   d) a polynucleotide sequence that encodes a polypeptide having at least 90% sequence identity with the amino acid sequence of SEQ ID NO: 42;
   e) a polynucleotide sequence that is complementary to the full-length LMP nucleic acid of a) or b) above; and
   f) a polynucleotide sequence that hybridizes under stringent conditions to the full-length LMP nucleic acid of a) or b) above, wherein the stringent conditions comprise hybridization in 6×SSC at about 45° C. followed by one or more washes in 0.2×SSC, 0.1% SDS at 50 to 65° C., wherein the seed weight is increased in the plant as compared to an untransformed wild type variety of the plant.

10. A transgenic plant made by a method comprising, transforming a plant cell with an expression vector comprising a lipid metabolism protein (LMP) nucleic acid, and generating from the plant cell the transgenic plant, wherein the nucleic acid encodes a polypeptide that increases seed weight in the plant, and the nucleic acid comprises a polynucleotide sequence selected from the group consisting of:
   a) the polynucleotide sequence of SEQ ID NO: 40 or SEQ ID NO: 41;
   b) a polynucleotide sequence encoding the polypeptide of SEQ ID NO: 42;
   c) a polynucleotide sequence having at least 90% sequence identity with the full-length LMP nucleic acid of a) or b) above;
   d) a polynucleotide sequence that encodes a polypeptide having at least 90% sequence identity with the amino acid sequence of SEQ ID NO: 42;
   e) a polynucleotide sequence that is complementary to the full-length LMP nucleic acid of a) or b) above; and
   f) a polynucleotide sequence that hybridizes under stringent conditions to the full-length LMP nucleic acid of a) or b) above, wherein the stringent conditions comprise hybridization in 6×SSC at about 45° C. followed by one or more washes in 0.2×SSC, 0.1% SDS at 50 to 65° C., wherein the seed weight is increased in the transgenic plant as compared to an untransformed wild type variety of the plant.

11. The transgenic plant of claim 10, wherein the plant is a dicotyledonous plant.

12. The transgenic plant of claim 10, wherein the plant is a monocotyledonous plant.

13. The transgenic plant of claim 10, wherein the plant is a high oil producing plant.

14. The method of claim 1, wherein the LMP nucleic acid comprises a polynucleotide sequence selected from the group consisting of:
   a) a polynucleotide sequence having at least 99% sequence identity with SEQ ID NO: 41 or 42; and
   b) a polynucleotide sequence encoding a polypeptide having 99% sequence identity with the amino acid sequence of SEQ ID NO: 42.

15. The transgenic plant of claim 10, wherein the polynucleotide sequence is selected from the group consisting of:
   a) a polynucleotide sequence having at least 95% sequence identity with the nucleic acid sequence of SEQ ID NO: 40 or 41; and
   b) a polynucleotide sequence encoding a polypeptide having 95% sequence identity with the amino acid sequence of SEQ ID NO: 42.

16. The transgenic plant of claim 10, wherein the polynucleotide sequence is selected from the group consisting of:
   a) a polynucleotide sequence having at least 99% sequence identity with the nucleic acid sequence of SEQ ID NO: 40 or 41; and
   b) a polynucleotide sequence encoding a polypeptide having 99% sequence identity with the amino acid sequence of SEQ ID NO: 42.

17. The transgenic plant of claim 10, wherein the polynucleotide sequence is selected from the group consisting of:
   a) the polynucleotide sequence of SEQ ID NO: 40 or 41; and
   b) a polynucleotide sequence encoding the amino acid sequence of SEQ ID NO: 42.

* * * * *

SEQUENCE LISTING

```
<160> NUMBER OF SEQ ID NOS: 58

<210> SEQ ID NO 1
<211> LENGTH: 1577
<212> TYPE: DNA
<213> ORGANISM: Arabidopsis thaliana

<400> SEQUENCE: 1
aaaccactct gcttcctctt cctctgagaa atcaaatcac tcacactcca aaaaaaaatc      60
taaactttct cagagtttac gcccttggta ccaaatctaa actttctcag agtttaatga     120
agaagcgctt aaccacttcc acttgttctt cttctccatc ttcctctgtt tcttcttcta     180
ctactacttc ctctcctatt cagtcggagg ctccaaggcc taaacgagcc aaaagggcta     240
agaaatcttc tccttctggt gataaatctc ataacccgac aagccctgct tctacccgac     300
gcagctctat ctacagagga gtcactagac atagatggac tgggagattc gaggctcatc     360
tttgggacaa aagctcttgg aattcgattc agaacaagaa aggcaaacaa gtttatctgg     420
gagcatatga cagtgaagaa gcagcagcac atacgtacga tctggctgct ctcaagtact     480
ggggacccga caccatcttg aattttccgg cagagacgta cacaaggaa ttggaagaaa      540 tgcagagagt gacaaaggaa gaatatttgg cttctctccg ccgccagagc agtggtttct     600
ccagaggcgt ctctaaatat cgcggcgtcg ctaggcatca ccacaacgga agatgggagg     660
ctcggatcgg aagagtgttt gggaacaagt acttgtacct cggcacctat aatacgcagg     720
aggaagctgc tgcagcatat gacatggctg cgattgagta tcgaggcgca aacgcggtta     780
ctaatttcga cattagtaat tacattgacc ggttaaagaa gaaggtgtt ttcccgttcc      840 ctgtgaacca agctaaccat caagagggta ttcttgttga agccaaacaa gaagttgaaa     900
```

```
cgagagaagc gaaggaagag cctagagaag aagtgaaaca acagtacgtg gaagaaccac    960
cgcaagaaga agaagagaag gaagaagaga aagcagagca acaagaagca gagattgtag   1020
gatattcaga agaagcagca gtggtcaatt gctgcataga ctcttcaacc ataatggaaa   1080
tggatcgttg tggggacaac aatgagctgg cttggaactt ctgtatgatg gatacagggt   1140
tttctccgtt tttgactgat cagaatctcg cgaatgagaa tcccatagag tatccggagc   1200
tattcaatga gttagcattt gaggacaaca tcgacttcat gttcgatgat gggaagcacg   1260
agtgcttgaa cttggaaaat ctggattgtt gcgtggtggg aagagagagc ccaccctctt   1320
cttcttcacc attgtcttgc ttatctactg actctgcttc atcaacaaca acaacaacaa   1380
cctcggtttc ttgtaactat ttggtctgag agagagagct ttgccttcta gtttgaattt   1440
ctatttcttc cgcttcttct tcttttttttt cttttgttgg gttctgctta gggttttgtat  1500 ttcagtttca gggcttgttc gttggttctg aataatcaat gtctttgccc cttttctaat   1560
gggtacctga agggcga                                                  1577

<210> SEQ ID NO 2
<211> LENGTH: 1293
<212> TYPE: DNA
<213> ORGANISM: Arabidopsis thaliana

<400> SEQUENCE: 2
atgaagaagc gcttaaccac ttccacttgt tcttcttctc catcttcctc tgtttcttct     60
tctactacta cttcctctcc tattcagtcg gaggctccaa ggcctaaacg agccaaaagg    120
gctaagaaat cttctccttc tggtgataaa tctcataacc cgacaagccc tgcttctacc    180
cgacgcagct ctatctacag aggagtcact agacatagat ggactgggag attcgaggct    240
catctttggg acaaaagctc ttggaattcg attcagaaca gaaaggcaa  caagtttat     300 ctgggagcat atgacagtga agaagcagca gcacatacgt acgatctggc tgctctcaag    360
tactggggac ccgacaccat cttgaatttt ccggcagaga cgtacacaaa ggaattggaa    420
gaaatgcaga gagtgacaaa ggaagaatat ttggcttctc tccgccgcca gagcagtggt    480
ttctccagag gcgtctctaa atatcgcggc gtcgctaggc atcaccacaa cggaagatgg    540
gaggctcgga tcggaagagt gtttgggaac aagtacttgt acctcggcac ctataatacg    600
caggaggaag ctgctgcagc atatgacatg gctgcgattg agtatcgagg cgcaaacgcg    660
gttactaatt tcgacattag taattacatt gaccggttaa agaagaaagg tgttttcccg    720
ttccctgtga accaagctaa ccatcaagag ggtattcttg ttgaagccaa acaagaagtt    780
gaaacgagag aagcgaagga agagcctaga aagaagtga aacaacagta cgtggaagaa    840
ccaccgcaag aagaagaaga gaaggaagaa gagaaagcag agcaacaaga agcagagatt    900
gtaggatatt cagaagaagc agcagtggtc aattgctgca tagactcttc aaccataatg    960
gaaatggatc gttgtgggga caacaatgag ctggcttgga acttctgtat gatggataca   1020
gggttttctc cgttttttgac tgatcagaat ctcgcgaatg agaatcccat agagtatccg   1080
gagctattca atgagttagc atttgaggac aacatcgact tcatgttcga tgatgggaag   1140
cacgagtgct tgaacttgga aaatctggat tgttgcgtgg tgggaagaga gagcccaccc   1200
tcttcttctt caccattgtc ttgcttatct actgactctg cttcatcaac aacaacaaca   1260
acaacctcgg tttcttgtaa ctatttggtc tga                                1293

<210> SEQ ID NO 3
<211> LENGTH: 430
```

```
<212> TYPE: PRT
<213> ORGANISM: Arabidopsis thaliana

<400> SEQUENCE: 3

Met Lys Lys Arg Leu Thr Thr Ser Thr Cys Ser Ser Ser Pro Ser Ser
 1               5                  10                  15

Ser Val Ser Ser Thr Thr Thr Ser Ser Pro Ile Gln Ser Glu Ala
                20                  25                  30

Pro Arg Pro Lys Arg Ala Lys Arg Ala Lys Lys Ser Ser Pro Ser Gly
            35                  40                  45

Asp Lys Ser His Asn Pro Thr Ser Pro Ala Ser Thr Arg Arg Ser Ser
        50                  55                  60

Ile Tyr Arg Gly Val Thr Arg His Arg Trp Thr Gly Arg Phe Glu Ala
 65                  70                  75                  80

His Leu Trp Asp Lys Ser Ser Trp Asn Ser Ile Gln Asn Lys Lys Gly
                85                  90                  95

Lys Gln Val Tyr Leu Gly Ala Tyr Asp Ser Glu Glu Ala Ala Ala His
            100                 105                 110

Thr Tyr Asp Leu Ala Ala Leu Lys Tyr Trp Gly Pro Asp Thr Ile Leu
        115                 120                 125

Asn Phe Pro Ala Glu Thr Tyr Thr Lys Glu Leu Glu Glu Met Gln Arg
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Ala Arg Ile Gly Arg Val Phe Gly Asn Lys Tyr
            180                 185                 190

Leu Tyr Leu Gly Thr Tyr Asn Thr Gln Glu Glu Ala Ala Ala Ala Tyr
        195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Glu Pro Arg Glu Glu
            260                 265                 270

Val Lys Gln Gln Tyr Val Glu Glu Pro Pro Gln Glu Glu Glu Glu Lys
        275                 280                 285

Glu Glu Glu Lys Ala Glu Gln Gln Gly Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
            340                 345                 350

Asn Glu Asn Pro Ile Glu Tyr Pro Glu Leu Phe Asn Glu Leu Ala Phe
        355                 360                 365

Glu Asp Asn Ile Asp Phe Met Phe Asp Asp Gly Lys His Glu Cys Leu
    370                 375                 380

Asn Leu Glu Asn Leu Asp Cys Cys Val Val Gly Arg Glu Ser Pro Pro
385                 390                 395                 400
```

| Ser | Ser | Ser | Ser | Pro | Leu | Ser | Cys | Leu | Ser | Thr | Asp | Ser | Ala | Ser | Ser |
|-----|-----|-----|-----|-----|-----|-----|-----|-----|-----|-----|-----|-----|-----|-----|-----|
|     |     |     | 405 |     |     |     | 410 |     |     |     | 415 |     |     |     |     |

| Thr | Thr | Thr | Thr | Thr | Thr | Ser | Val | Ser | Cys | Asn | Tyr | Leu | Val |
|-----|-----|-----|-----|-----|-----|-----|-----|-----|-----|-----|-----|-----|-----|
| 420 |     |     |     |     |     | 425 |     |     |     |     | 430 |     |     |

<210> SEQ ID NO 4
<211> LENGTH: 1509
<212> TYPE: DNA
<213> ORGANISM: Brassica napus

<400> SEQUENCE: 4

```
cttgcacaca gtgcgtcttt ggttttctct ttcctagggt ttgtgttttg gttctgatca      60
tggcgtcgat gtcgtcgccg gatcaggggc ctaagacaga ggcgggagga ggaggagaga     120
gctcggagaa tgtgtcggcg agtgatcaga tgttgctgta tagaagtttt aagaaggcga     180
agaaggagag aggatgcaca gctaaggagc gtatcagtaa aatgccgccc tgcacagctg     240
gcaaaaggag ttctatttac cgtggagtca ccagacatag atggacaggt cggtacgaag     300
ctcacctttg ggacaagagt acttggaacc aaaaccagaa caagaagggc aaacaagttt     360
atctaggagc atatgatgat gaagaggctg ctgctagagc ctacgacctt gctgccttga     420
aatactgggg acctggaaca cttatcaatt ttccggtgac tgattactct agggatttag     480
aagaaatgca aagtctctca agggaagaat accttgcaac tctacgtaga aaaagcagcg     540
gtttctcaag gggaatagcc aaatatcgtg gccttcaaag ccgatgggaa gcatcagcca     600
gtcggatgcc tggacctgaa tacttcggta gccttcatta cggtgatgaa cgaggagcag     660
aaggtgactt tcttggcagc ttttgtctgg aaagaaagat tgatctaacg ggatacataa     720
agtggtgggg agtcaacaaa cccggtcaac cagaatcttc atcaaaggca tcagaggatg     780
caaaggtaga agatgcaggt actgagctta agacactgga cacgcttcc caggcaacag     840
agccatacaa agcaccaaac tttggcgttc atcatggcac tcagaggaaa ggaaaacaaa     900
taacatcgcc gtcctccacc tcttctgctt taagcatttt gtctgcgtca cctgcttaca     960
agagtctgga ggagaaagtg atgaagatcc aagaaagtag cagcactaga gaaaacgatg    1020
agaatgcaaa ccgtaacatc aatagtattg agaagagtca cggtaaggaa atagagaaac    1080
caccggtcgt gagtcatgga gtttctctag gcagtggtgg tggtgttgct cctgctgctg    1140
ctgctttgtc tcttcagaaa agcatgtacc cacttgcctc tctcttaact gctccactgc    1200
tcagcaatta caatacattg gatccccttg gagagcctat tctctggaca ccgttccttc    1260
acccaggatc ttctcatact ttagaggtga caaagacaga gcaagttgt tccacataca    1320
gttacctccc acaagagaag tgagccgttc ccctttagac tgtttgtgaa aatgatctga    1380
agcaggaatg tacaggtttt tgtcagtgtt ttatgtgtat tttcagtgtg gaatatatat    1440
agaatcatta tacttaaatg taaaacaggc aaaatttatg attatacagt agtataaagg    1500
tttgctctt                                                           1509
```

<210> SEQ ID NO 5
<211> LENGTH: 1284
<212> TYPE: DNA
<213> ORGANISM: Brassica napus

<400> SEQUENCE: 5

```
atggcgtcga tgtcgtcgcc ggatcagggg cctaagacag aggcgggagg aggaggagag      60
agctcggaga atgtgtcggc gagtgatcag atgttgctgt atagaagttt taagaaggcg     120
aagaaggaga gaggatgcac agctaaggag cgtatcagta aaatgccgcc tgcacagct     180
```

-continued

```
ggcaaaagga gttctatttta ccgtggagtc accagacata gatggacagg tcggtacgaa    240
gctcaccttt gggacaagag tacttggaac caaaaccaga acaagaaggg caaacaagtt    300
tatctaggag catatgatga tgaagaggct gctgctagag cctacgacct tgctgccttg    360
aaatactggg gacctggaac acttatcaat tttccggtga ctgattactc tagggattta    420
gaagaaatgc aaagtctctc aagggaagaa taccttgcaa ctctacgtag aaaaagcagc    480
ggtttctcaa ggggaatagc caaatatcgt ggccttcaaa gccgatggga agcatcagcc    540
agtcggatgc ctggacctga atacttcggt agccttcatt acggtgatga acgaggagca    600
gaaggtgact tcttggcag cttttgtctg gaaagaaaga ttgatctaac gggatacata    660
aagtggtggg gagtcaacaa acccggtcaa ccagaatctt catcaaaggc atcagaggat    720
gcaaaggtag aagatgcagg tactgagctt aagacactgg aacacgcttc ccaggcaaca    780
gagccataca aagcaccaaa ctttggcgtt catcatggca ctcagaggaa aggaaaacaa    840
ataacatcgc cgtcctccac ctcttctgct ttaagcattt tgtctgcgtc acctgcttac    900
aagagtctgg aggagaaagt gatgaagatc aagaaagta gcagcactag agaaaacgat    960
gagaatgcaa accgtaacat caatagtatt gagaagagtc acggtaagga aatagagaaa   1020
ccaccggtcg tgagtcatgg agtttctcta ggcagtggtg gtggtgttgc tcctgctgct   1080
gctgctttgt ctcttcagaa aagcatgtac ccacttgcct ctctcttaac tgctccactg   1140
ctcagcaatt acaatacatt ggatccccctt ggagagccta ttctctggac accgttcctt   1200
cacccaggat cttctcatac tttagaggtg acaaagacag agacaagttg ttccacatac   1260
agttaccctcc cacaagagaa gtga                                          1284

<210> SEQ ID NO 6
<211> LENGTH: 427
<212> TYPE: PRT
<213> ORGANISM: Brassica napus

<400> SEQUENCE: 6

Met Ala Ser Met Ser Ser Pro Asp Gln Gly Pro Lys Thr Glu Ala Gly
 1               5                  10                  15

Gly Gly Gly Glu Ser Ser Glu Asn Val Ser Ala Ser Asp Gln Met Leu
            20                  25                  30

Leu Tyr Arg Ser Phe Lys Lys Ala Lys Lys Glu Arg Gly Cys Thr Ala
        35                  40                  45

Lys Glu Arg Ile Ser Lys Met Pro Pro Cys Thr Ala Gly Lys Arg Ser
    50                  55                  60

Ser Ile Tyr Arg Gly Val Thr Arg His Arg Trp Thr Gly Arg Tyr Glu
65                  70                  75                  80

Ala His Leu Trp Asp Lys Ser Thr Trp Asn Gln Asn Gln Asn Lys Lys
                85                  90                  95

Gly Lys Gln Val Tyr Leu Gly Ala Tyr Asp Asp Glu Glu Ala Ala Ala
            100                 105                 110

Arg Ala Tyr Asp Leu Ala Ala Leu Lys Tyr Trp Gly Pro Gly Thr Leu
        115                 120                 125

Ile Asn Phe Pro Val Thr Asp Tyr Ser Arg Asp Leu Glu Glu Met Gln
    130                 135                 140

Ser Leu Ser Arg Glu Glu Tyr Leu Ala Thr Leu Arg Arg Lys Ser Ser
145                 150                 155                 160

Gly Phe Ser Arg Gly Ile Ala Lys Tyr Arg Gly Leu Gln Ser Arg Trp
                165                 170                 175

Glu Ala Ser Ala Ser Arg Met Pro Gly Pro Glu Tyr Phe Gly Ser Leu
```

His Tyr Gly Asp Glu Arg Gly Ala Glu Gly Asp Phe Leu Gly Ser Phe
            180                 185                 190

Cys Leu Glu Arg Lys Ile Asp Leu Thr Gly Tyr Ile Lys Trp Trp Gly
        195                 200                 205

Val Asn Lys Pro Gly Gln Pro Glu Ser Ser Lys Ala Ser Glu Asp
    210                 215                 220

Val Asn Lys Pro Gly Gln Pro Glu Ser Ser Lys Ala Ser Glu Asp
225                 230                 235                 240

Ala Lys Val Glu Asp Ala Gly Thr Glu Leu Lys Thr Leu Glu His Ala
                245                 250                 255

Ser Gln Ala Thr Glu Pro Tyr Lys Ala Pro Asn Phe Gly Val His His
            260                 265                 270

Gly Thr Gln Arg Lys Gly Lys Gln Ile Thr Ser Pro Ser Thr Ser
        275                 280                 285

Ser Ala Leu Ser Ile Leu Ser Ala Ser Pro Ala Tyr Lys Ser Leu Glu
    290                 295                 300

Glu Lys Val Met Lys Ile Gln Glu Ser Ser Thr Arg Glu Asn Asp
305                 310                 315                 320

Glu Asn Ala Asn Arg Asn Ile Asn Ser Ile Glu Lys Ser His Gly Lys
                325                 330                 335

Glu Ile Glu Lys Pro Pro Val Val Ser His Gly Val Ser Leu Gly Ser
            340                 345                 350

Gly Gly Gly Val Ala Pro Ala Ala Ala Leu Ser Leu Gln Lys Ser
        355                 360                 365

Met Tyr Pro Leu Ala Ser Leu Leu Thr Ala Pro Leu Leu Ser Asn Tyr
    370                 375                 380

Asn Thr Leu Asp Pro Leu Gly Glu Pro Ile Leu Trp Thr Pro Phe Leu
385                 390                 395                 400

His Pro Gly Ser Ser His Thr Leu Glu Val Thr Lys Thr Glu Thr Ser
                405                 410                 415

Cys Ser Thr Tyr Ser Tyr Leu Pro Gln Glu Lys
            420                 425

<210> SEQ ID NO 7
<211> LENGTH: 1392
<212> TYPE: DNA
<213> ORGANISM: Brassica napus

<400> SEQUENCE: 7
taatgaagag acccttaacc acttctcctt cttcctcctc ttctacttct tcttcggcct       60
gtatacttcc gactcaatca gagactccaa ggcccaaacg agccaaaagg ctaagaaat      120 cttctctgcg ttctgatgtt aaaccacaga atcccaccag tcctgcctcc accagacgca      180
gctctatcta cagaggagtc actagacata gatggacagg gagatacgaa gctcatctat      240
gggacaaaag ctcgtggaat tcgattcaga acaagaaagg caaacaagtt tatctgggag      300
catatgacag cgaggaagca gcagcacata cgtacgatct agctgctctc aagtactggg      360
gtcccaacac catcttgaac tttccggttg agacgtacac aaaggagctg aggagatgc      420 agagatgtac aaaggaagag tatttggctt ctctccgccg ccagagcagt ggtttctcta      480
gaggcgtctc taaatatcgc ggcgtcgcca ggcatcacca taacggaaga tgggaagctc      540
ggattggaag ggtgtttgga aacaagtact tgtacctcgg cacctataat acgcaggagg      600
aagctgcagc tgcatatgac atggcggcta tagagtacag aggtgcaaac gcagtgacca      660
acttcgacat tagtaactac atcgaccggt taaagaaaaa aggtgtcttc ccgttccccg      720
tgagccaagc taatcatcaa gaagctgttc ttgctgaaac caaacaagaa gtggaagcta      780

| aagaagagcc tacagaagaa gtgaagcagt gtgtcgaaaa agaagaagct aaagaagaga | 840 |
| agactgagaa aaaacaacaa caagaagtgg aggaggcggt gatcacttgc tgcattgatt | 900 |
| cttcagagag caatgagctg gcttgggact tctgtatgat ggattcaggg tttgctccgt | 960 |
| ttttgactga ttcaaatctc tcgagtgaga atcccattga gtatcctgag cttttcaatg | 1020 |
| agatgggttt tgaggataac attgacttca tgttcgagga agggaagcaa gactgcttga | 1080 |
| gcttggagaa tcttgattgt tgcgatggtg ttgttgtggt gggaagagag agcccaactt | 1140 |
| cattgtcgtc ttctccgttg tcctgcttgt ctactgactc tgcttcatca acaacaacaa | 1200 |
| cagcaacaac agtaacctct gtttcttgta actattctgt ctgaggggg agagctttgc | 1260 |
| atttctaggt tgaattttct atttcttttg cttcttttt ttttgttgag ttctgctagg | 1320 |
| gtttgtattc tgtttcaggg cttactcatt ggttctgaca gtcaatgttt agctctcttt | 1380 |
| tccgctcgtc ta | 1392 |

<210> SEQ ID NO 8
<211> LENGTH: 1242
<212> TYPE: DNA
<213> ORGANISM: Brassica napus

<400> SEQUENCE: 8

| atgaagagac ccttaaccac ttctccttct tcctcctctt ctacttcttc ttcggcctgt | 60 |
| atacttccga ctcaatcaga gactccaagg cccaaacgag ccaaagggc taagaaatct | 120 |
| tctctgcgtt ctgatgttaa accacagaat cccaccagtc ctgcctccac cagacgcagc | 180 |
| tctatctaca gaggagtcac tagacataga tggacaggga gatacgaagc tcatctatgg | 240 |
| gacaaaagct cgtggaattc gattcagaac aagaaaggca acaagtttat ctgggagca | 300 |
| tatgacagcg aggaagcagc agcacatacg tacgatctag ctgctctcaa gtactggggt | 360 |
| cccaacacca tcttgaactt tccggttgag acgtacacaa aggagctgga ggagatgcag | 420 |
| agatgtacaa aggaagagta tttggcttct ctccgccgcc agagcagtgg tttctctaga | 480 |
| ggcgtctcta aatatcgcgg cgtcgccagg catcaccata acggaagatg gaagctcgg | 540 |
| attggaaggg tgtttggaaa caagtacttg tacctcggca cctataatac gcaggaggaa | 600 |
| gctgcagctg catatgacat ggcggctata gagtacagag gtgcaaacgc agtgaccaac | 660 |
| ttcgacatta gtaactacat cgaccggtta agaaaaaaag gtgtcttccc gttcccgtg | 720 |
| agccaagcta atcatcaaga agctgttctt gctgaaacca acaagaagt ggaagctaaa | 780 |
| gaagagccta cagaagaagt gaagcagtgt gtcgaaaag aagaagctaa agaagagaag | 840 |
| actgagaaaa acaacaaca agaagtggag gaggcggtga tcacttgctg cattgattct | 900 |
| tcagagagca atgagctggc ttgggacttc tgtatgatgg attcagggtt tgctccgttt | 960 |
| ttgactgatt caaatctctc gagtgagaat cccattgagt atcctgagct tttcaatgag | 1020 |
| atgggttttg aggataacat tgacttcatg ttcgaggaag ggaagcaaga ctgcttgagc | 1080 |
| ttggagaatc ttgattgttg cgatggtgtt gttgtggtgg gaagagagag cccaacttca | 1140 |
| ttgtcgtctt ctccgttgtc ctgcttgtct actgactctg cttcatcaac aacaacaaca | 1200 |
| gcaacaacag taacctctgt ttcttgtaac tattctgtct ga | 1242 |

<210> SEQ ID NO 9
<211> LENGTH: 413
<212> TYPE: PRT
<213> ORGANISM: Brassica napus

<400> SEQUENCE: 9

```
Met Lys Arg Pro Leu Thr Thr Ser Pro Ser Ser Ser Ser Thr Ser
  1               5                  10                  15

Ser Ser Ala Cys Ile Leu Pro Thr Gln Ser Glu Thr Pro Arg Pro Lys
             20                  25                  30

Arg Ala Lys Arg Ala Lys Lys Ser Ser Leu Arg Ser Asp Val Lys Pro
         35                  40                  45

Gln Asn Pro Thr Ser Pro Ala Ser Thr Arg Arg Ser Ser Ile Tyr Arg
     50                  55                  60

Gly Val Thr Arg His Arg Trp Thr Gly Arg Tyr Glu Ala His Leu Trp
 65                  70                  75                  80

Asp Lys Ser Ser Trp Asn Ser Ile Gln Asn Lys Lys Gly Lys Gln Val
                 85                  90                  95

Tyr Leu Gly Ala Tyr Asp Ser Glu Glu Ala Ala Ala His Thr Tyr Asp
             100                 105                 110

Leu Ala Ala Leu Lys Tyr Trp Gly Pro Asn Thr Ile Leu Asn Phe Pro
         115                 120                 125

Val Glu Thr Tyr Thr Lys Glu Leu Glu Glu Met Gln Arg Cys Thr Lys
     130                 135                 140

Glu Glu Tyr Leu Ala Ser Leu Arg Arg Gln Ser Ser Gly Phe Ser Arg
145                 150                 155                 160

Gly Val Ser Lys Tyr Arg Gly Val Ala Arg His His His Asn Gly Arg
                 165                 170                 175

Trp Glu Ala Arg Ile Gly Arg Val Phe Gly Asn Lys Tyr Leu Tyr Leu
             180                 185                 190

Gly Thr Tyr Asn Thr Gln Glu Glu Ala Ala Ala Ala Tyr Asp Met Ala
         195                 200                 205

Ala Ile Glu Tyr Arg Gly Ala Asn Ala Val Thr Asn Phe Asp Ile Ser
     210                 215                 220

Asn Tyr Ile Asp Arg Leu Lys Lys Lys Gly Val Phe Pro Phe Pro Val
225                 230                 235                 240

Ser Gln Ala Asn His Gln Glu Ala Val Leu Ala Glu Thr Lys Gln Glu
                 245                 250                 255

Val Glu Ala Lys Glu Glu Pro Thr Glu Val Lys Gln Cys Val Glu
             260                 265                 270

Lys Glu Glu Ala Lys Glu Lys Thr Glu Lys Lys Gln Gln Gln Glu
         275                 280                 285

Val Glu Glu Ala Val Ile Thr Cys Cys Ile Asp Ser Ser Glu Ser Asn
     290                 295                 300

Glu Leu Ala Trp Asp Phe Cys Met Met Asp Ser Gly Phe Ala Pro Phe
305                 310                 315                 320

Leu Thr Asp Ser Asn Leu Ser Ser Glu Asn Pro Ile Glu Tyr Pro Glu
                 325                 330                 335

Leu Phe Asn Glu Met Gly Phe Glu Asp Asn Ile Asp Phe Met Phe Glu
             340                 345                 350

Glu Gly Lys Gln Asp Cys Leu Ser Leu Glu Asn Leu Asp Cys Cys Asp
         355                 360                 365

Gly Val Val Val Gly Arg Glu Ser Pro Thr Ser Leu Ser Ser Ser
     370                 375                 380

Pro Leu Ser Cys Leu Ser Thr Asp Ser Ala Ser Ser Thr Thr Thr Thr
385                 390                 395                 400

Ala Thr Thr Val Thr Ser Val Ser Cys Asn Tyr Ser Val
                 405                 410
```

```
<210> SEQ ID NO 10
<211> LENGTH: 1375
<212> TYPE: DNA
<213> ORGANISM: Brassica napus

<400> SEQUENCE: 10
taatgaagag accettaacc acttgtacat cttcttctac atcatcttct acttcttcat      60
cttgtatcct tcggaaccaa ccagagactc caaggcctaa acgagccaaa agggctaaga     120
aatcatcgcc cccttgtgat gtaaaaccac agaacccgac cagtcctgcc tctgccagac     180
gcagctctat ctacagagga gtcaccagac atagatggac tgggagattt gaggctcatc     240
tatgggataa aagctcttgg aattcgattc agaacaagaa aggcaaacaa gtttatttgg     300
gagcatatga cagcgaggaa gcagctgcac atacgtacga tctagctgct ctcaagtact     360
ggggtcccga caccatcttg aattttccgg ttgagacgta caaaaaggag ttggatgaaa     420
tgcagagagg cacaaaagaa gagtatttgg gttctctccg ccgccagagc agtggtttct     480
ccagaggcgt ctctaaatat cgcggcgtcg ccaggcatca cataacggaa agatgggagg     540
ctcggattgg aagagttttc ggaaacaagt acttatacct cggcacctat aatacgcagg     600
aggaagctgc agaagcatat gacatggctg cgattaata tagaggtgca aacgctgtta      660
ccaattttga cattagtaat tacatcgacc ggctaaagaa aaaaggcgtt ttcccgttcc     720
gtgtggacca agctaaccat caagaggctg ttcttgctga agccaaacaa gaagctaaga     780
aagaagtgaa agagcacgtg gaagaagaac atcaagaaga gaaaacagag cagcatcaag     840
aagtggaggc ggtcacttgc ggcatagatg cttcaggcat tatggagatg gaacgttctt     900
cagacagcaa tgagttggct tggaacttct gtatgatgga ttcagggttt gctccgttct     960
tgacagatca aaacctctcg aatgagaatc ccatagagta tcctgagctt ttcaacgaga    1020
tgatgggttt tgaggataac gacatagact tcatgtttga ggaagccaag aacgaatgct    1080
tgagcttgga gaatctggat tgttgtgatg tcgttgtggt gggaagagaa agcccagctt    1140
ctttatcgtc ttctccgttg tcttgctttt ctactgactc tgcttcatca acaacaacaa    1200
caacaaactc tgtttcttgt aactattctg tctgagggag agagctttgc attatagggt    1260
tgagttttct atttcttttg cttcttgatc ttgtccttgt tgagttccgc tagggttttt    1320 gttttttcgtt tcagggctta ctcgttggtt ctgaacaatc aatgtcttcg cctca         1375

<210> SEQ ID NO 11
<211> LENGTH: 1233
<212> TYPE: DNA
<213> ORGANISM: Brassica napus

<400> SEQUENCE: 11
atgaagagac ccttaaccac ttgtacatct tcttctacat catcttctac ttcttcatct      60 tgtatcctc ggaaccaacc agagactcca aggcctaaac gagccaaaag ggctaagaaa     120
tcatcgcccc cttgtgatgt aaaaccacag aacccgacca gtcctcctc tgccagacgc     180 agctctatct acagaggagt caccagacat agatggactg ggagatttga ggctcatcta     240
tgggataaaa gctcttggaa ttcgattcag aacaagaaag caaacaagt ttatttggga     300 gcatatgaca gcgaggaagc agctgcacat acgtacgatc tagctgctct caagtactgg     360
ggtcccgaca ccatcttgaa ttttccggtt gagacgtaca aaaaggagtt ggatgaaatg     420
cagagaggca caaaagaaga gtatttgggt tctctccgcc gccagagcag tggtttctcc     480
agaggcgtct ctaaatatcg cggcgtcgcc aggcatcacc ataacggaag atgggaggct     540
cggattggaa gagttttcgg aaacaagtac ttatacctcg gcacctataa tacgcaggag     600
```

```
gaagctgcag aagcatatga catggctgcg attgaatata gaggtgcaaa cgctgttacc    660
aattttgaca ttagtaatta catcgaccgg ctaaagaaaa aaggcgtttt cccgttccgt    720
gtggaccaag ctaaccatca agaggctgtt cttgctgaag ccaaacaaga agctaagaaa    780
gaagtgaaag agcacgtgga agaagaacat caagaagaga aaacagagca gcatcaagaa    840
gtggaggcgg tcacttgcgg catagatgct tcaggcatta tggagatgga acgttcttca    900
gacagcaatg agttggcttg gaacttctgt atgatggatt cagggtttgc tccgttcttg    960
acagatcaaa acctctcgaa tgagaatccc atagagtatc ctgagctttt caacgagatg   1020
atgggttttg aggataacga catagacttc atgtttgagg aagccaagaa cgaatgcttg   1080
agcttggaga atctggattg ttgtgatgtc gttgtggtgg aagagaaaag cccagcttct   1140
ttatcgtctt ctccgttgtc ttgctttttct actgactctg cttcatcaac aacaacaaca   1200
acaaactctg tttcttgtaa ctattctgtc tga                                1233
```

<210> SEQ ID NO 12
<211> LENGTH: 410
<212> TYPE: PRT
<213> ORGANISM: Brassica napus

<400> SEQUENCE: 12

```
Met Lys Arg Pro Leu Thr Thr Cys Thr Ser Ser Thr Ser Ser Ser
 1               5                  10                  15

Thr Ser Ser Ser Cys Ile Leu Arg Asn Gln Pro Glu Thr Pro Arg Pro
                20                  25                  30

Lys Arg Ala Lys Arg Ala Lys Lys Ser Ser Pro Pro Cys Asp Val Lys
            35                  40                  45

Pro Gln Asn Pro Thr Ser Pro Ala Ser Ala Arg Arg Ser Ser Ile Tyr
        50                  55                  60

Arg Gly Val Thr Arg His Arg Trp Thr Gly Arg Phe Glu Ala His Leu
 65                 70                  75                  80

Trp Asp Lys Ser Ser Trp Asn Ser Ile Gln Asn Lys Lys Gly Lys Gln
                85                  90                  95

Val Tyr Leu Gly Ala Tyr Asp Ser Glu Glu Ala Ala Ala His Thr Tyr
            100                 105                 110

Asp Leu Ala Ala Leu Lys Tyr Trp Gly Pro Asp Thr Ile Leu Asn Phe
        115                 120                 125

Pro Val Glu Thr Tyr Lys Lys Glu Leu Asp Glu Met Gln Arg Gly Thr
    130                 135                 140

Lys Glu Glu Tyr Leu Gly Ser Leu Arg Arg Gln Ser Ser Gly Phe Ser
145                 150                 155                 160

Arg Gly Val Ser Lys Tyr Arg Gly Val Ala Arg His His His Asn Gly
                165                 170                 175

Arg Trp Glu Ala Arg Ile Gly Arg Val Phe Gly Asn Lys Tyr Leu Tyr
            180                 185                 190

Leu Gly Thr Tyr Asn Thr Gln Glu Glu Ala Ala Glu Ala Tyr Asp Met
        195                 200                 205

Ala Ala Ile Glu Tyr Arg Gly Ala Asn Ala Val Thr Asn Phe Asp Ile
    210                 215                 220

Ser Asn Tyr Ile Asp Arg Leu Lys Lys Gly Val Phe Pro Phe Arg
225                 230                 235                 240

Val Asp Gln Ala Asn His Gln Glu Ala Val Leu Ala Glu Ala Lys Gln
                245                 250                 255

Glu Ala Lys Lys Glu Val Lys Glu His Val Glu Glu His Gln Glu
```

```
                260              265              270
Glu Lys Thr Glu Gln His Gln Glu Val Glu Ala Val Thr Cys Gly Ile
            275                  280              285
Asp Ala Ser Gly Ile Met Glu Met Glu Arg Ser Ser Asp Ser Asn Glu
            290                  295                  300
Leu Ala Trp Asn Phe Cys Met Met Asp Ser Gly Phe Ala Pro Phe Leu
305                  310                  315                  320
Thr Asp Gln Asn Leu Ser Asn Glu Asn Pro Ile Glu Tyr Pro Glu Leu
                325                  330                  335
Phe Asn Glu Met Met Gly Phe Gly Asp Asn Asp Ile Asp Phe Met Phe
                340                  345                  350
Glu Glu Ala Lys Asn Glu Cys Leu Ser Leu Glu Asn Leu Asp Cys Cys
            355                  360                  365
Asp Val Val Val Gly Arg Glu Ser Pro Ala Ser Leu Ser Ser Ser
        370                  375                  380
Pro Leu Ser Cys Phe Ser Thr Asp Ser Ala Ser Ser Thr Thr Thr Thr
385                  390                  395                  400
Thr Asn Ser Val Ser Cys Asn Tyr Ser Val
                405                  410

<210> SEQ ID NO 13
<211> LENGTH: 1392
<212> TYPE: DNA
<213> ORGANISM: Brassica napus

<400> SEQUENCE: 13
taatgaagag acccttaacc acttgtacat cttcttctac atcatcctct acttcttcat      60
cttgtatcct tccgaaccaa ccagagactc caaggcctaa cgagccaaa agggctaaga     120 aatcatctcc cccttgtgat gtaaaaccac agaacccgac cagtcctgcc tctgccagac     180
gcagctctat ctacagagga gtcaccgaca atagatggac tgggagattt gaggctcatc     240
tatgggataa aagctcttgg aattcgattc agaacaagaa aggcaaacaa gtttatctgg     300
gagcatatga cagcgaggaa gcagctgcac atacgtacga tctagctgct ctcaagtact     360
ggggtcccga caccatcttg aattttccgg ttgagacgta cacaaaggag ttggatgaaa     420
tgcagagagg cacaaaagaa gagtatttgg cttctctccg ccgccagagc agtggtttct     480
ccagaggcgt ctctaaatat cgcggcgtcg ccaggcatca ccataacgga agatgggagg     540
ctcggattgg aagagttttc ggaaacaagt acttatacct cggcacctat aatacgcagg     600
aggaagctgc tgaagcttat gatatggctg cgattgaata tagaggtgca aacgctgtta     660
ccaatttcga cattagtaat tacatcgacc gtttaaagaa aaaaggcgtt ttcccgttcc     720
gtgtggagca agccactcat caagaggctg ttcttgctga agccaaacaa gaagccaagg     780
aagaagtgaa agagcacgtg gaagaagaac atcaagaagc gagggaagag acaacgagagc     840 agaaacaaga agtggaggcg gtcacttgcg gcgtagatgc ttcaggcatt atggagatgg     900
aacgttcttc agacagcaat gagttggctt ggaacttctg tatgatggat tcagggtttg     960
ctccgttctt gacagatcaa aacctctcga atgagaatcc catagagtat cctgaacttt    1020
tcaacgagat gatgggtttt gaggataacg acatagactt catgttcgag gaagccaaga    1080
acgaatgctt gagcttggag aatctggatt gttgtgatgc cgttgtggtg ggaagagaaa    1140
gcccaacttc tttgtcgtct ctccgttgt cttgcttttc tactgactct gcttcatcaa    1200
caacaataac aacaacaaca acaacctctg tttcttgtaa ctattctgtc tgagggagag    1260
agctttgcat tataggggttg agttttctat ttcttttgct tcttgatctt gtccttgttg    1320
```

```
agttccgcta gggttttttgt ttttcgtttc agggcttact cgttggttct gaacaatcaa    1380
tgtcttcgcc tc                                                         1392

<210> SEQ ID NO 14
<211> LENGTH: 1251
<212> TYPE: DNA
<213> ORGANISM: Brassica napus

<400> SEQUENCE: 14
atgaagagac ccttaaccac ttgtacatct tcttctacat catcctctac ttcttcatct      60
tgtatccttc cgaaccaacc agagactcca aggcctaaac gagccaaaag ggctaagaaa     120
tcatctcccc cttgtgatgt aaaaccacag aacccgacca gtcctgcctc tgccagacgc     180
agctctatct acagaggagt caccagacat agatggactg ggagatttga ggctcatcta     240
tgggataaaa gctcttggaa ttcgattcag aacaagaaag gcaaacaagt ttatctggga     300
gcatatgaca gcgaggaagc agctgcacat acgtacgatc tagctgctct caagtactgg     360
ggtcccgaca ccatcttgaa ttttccggtt gagacgtaca caaggagtt ggatgaaatg      420 cagagaggca caaagaaga gtatttggct ctctccgcc gccagagcag tggtttctcc       480
agaggcgtct ctaaatatcg cggcgtcgcc aggcatcacc ataacggaag atgggaggct     540
cggattggaa gagttttcgg aaacaagtac ttatacctcg gcacctataa tacgcaggag     600
gaagctgctg aagcttatga tatggctgcg attgaatata gaggtgcaaa cgctgttacc     660
aatttcgaca ttagtaatta catcgaccgt ttaaagaaaa aaggcgtttt cccgttccgt     720
gtggagcaag ccactcatca gaggctgtt cttgctgaag ccaaacaaga agccaaggaa      780
gaagtgaaag agcacgtgga agaagaacat caagaagcga gggaagagac aacagagcag     840
aaacaagaag tggaggcggt cacttgcggc gtagatgctt caggcattat ggagatggaa     900
cgttcttcag acagcaatga gttggcttgg aacttctgta tgatggattc agggtttgct     960
ccgttcttga cagatcaaaa cctctcgaat gagaatccca tagagtatcc tgaacttttc    1020
aacgagatga tgggttttga ggataacgac atagacttca tgttcgagga agccaagaac    1080
gaatgcttga gcttggagaa tctggattgt tgtgatgtcg ttgtggtggg aagagaaagc    1140
caacttcttt gtcgtcttc tccgttgtct gcttttcta ctgactctgc ttcatcaaca     1200
acaataacaa caacaacaac aacctctgtt tcttgtaact attctgtctg a            1251

<210> SEQ ID NO 15
<211> LENGTH: 416
<212> TYPE: PRT
<213> ORGANISM: Brassica napus

<400> SEQUENCE: 15

Met Lys Arg Pro Leu Thr Thr Cys Thr Ser Ser Thr Ser Ser
  1               5                  10                  15

Thr Ser Ser Cys Ile Leu Pro Asn Gln Pro Glu Thr Pro Arg Pro
              20                  25                  30

Lys Arg Ala Lys Arg Ala Lys Lys Ser Ser Pro Cys Asp Val Lys
          35                  40                  45

Pro Gln Asn Pro Thr Ser Pro Ala Ser Ala Arg Arg Ser Ser Ile Tyr
      50                  55                  60

Arg Gly Val Thr Arg His Arg Trp Thr Gly Arg Phe Glu Ala His Leu
 65                  70                  75                  80

Trp Asp Lys Ser Ser Trp Asn Ser Ile Gln Asn Lys Lys Gly Lys Gln
                 85                  90                  95
```

Val Tyr Leu Gly Ala Tyr Asp Ser Glu Glu Ala Ala His Thr Tyr
            100                 105                 110

Asp Leu Ala Ala Leu Lys Tyr Trp Gly Pro Asp Thr Ile Leu Asn Phe
            115                 120                 125

Pro Val Glu Thr Tyr Thr Lys Glu Leu Asp Glu Met Gln Arg Gly Thr
130                 135                 140

Lys Glu Glu Tyr Leu Ala Ser Leu Arg Arg Gln Ser Ser Gly Phe Ser
145                 150                 155                 160

Arg Gly Val Ser Lys Tyr Arg Gly Val Ala Arg His His Asn Gly
            165                 170                 175

Arg Trp Glu Ala Arg Ile Gly Arg Val Phe Gly Asn Lys Tyr Leu Tyr
            180                 185                 190

Leu Gly Thr Tyr Asn Thr Gln Glu Glu Ala Ala Glu Ala Tyr Asp Met
            195                 200                 205

Ala Ala Ile Glu Tyr Arg Gly Ala Asn Ala Val Thr Asn Phe Asp Ile
            210                 215                 220

Ser Asn Tyr Ile Asp Arg Leu Lys Lys Lys Gly Val Phe Pro Phe Arg
225                 230                 235                 240

Val Glu Gln Ala Thr His Gln Glu Ala Val Leu Ala Glu Ala Lys Gln
            245                 250                 255

Glu Ala Lys Glu Glu Val Lys Glu His Val Glu Glu His Gln Glu
            260                 265                 270

Ala Arg Glu Glu Thr Thr Glu Gln Lys Gln Glu Val Glu Ala Val Thr
            275                 280                 285

Cys Gly Val Asp Ala Ser Gly Ile Met Glu Met Glu Arg Ser Ser Asp
            290                 295                 300

Ser Asn Glu Leu Ala Trp Asn Phe Cys Met Met Asp Ser Gly Phe Ala
305                 310                 315                 320

Pro Phe Leu Thr Asp Gln Asn Leu Ser Asn Glu Asn Pro Ile Glu Tyr
            325                 330                 335

Pro Glu Leu Phe Asn Glu Met Met Gly Phe Glu Asp Asn Asp Ile Asp
            340                 345                 350

Phe Met Phe Glu Glu Ala Lys Asn Glu Cys Leu Ser Leu Glu Asn Leu
            355                 360                 365

Asp Cys Cys Asp Val Val Val Gly Arg Glu Ser Pro Thr Ser Leu
            370                 375                 380

Ser Ser Ser Pro Leu Ser Cys Phe Ser Thr Asp Ser Ala Ser Ser Thr
385                 390                 395                 400

Thr Ile Thr Thr Thr Thr Thr Ser Val Ser Cys Asn Tyr Ser Val
            405                 410                 415

<210> SEQ ID NO 16
<211> LENGTH: 1457
<212> TYPE: DNA
<213> ORGANISM: Brassica napus

<400> SEQUENCE: 16
gatttcgtat tcccccaaac acacaaaatc tcattctctt ttttctcat agttttttt        60 aatgaagaga cccttaacca cttctccttc tacctcctct tctacttctt cttcggcttg     120
tatacttccg actcaaccag agactccaag gcccaaacga gccaaagggg ctaagaaatc     180
ttctattcct actgatgtta aaccacagaa tcccaccagt cctgcctcca ccagacgcag     240
ctctatctac agaggagtca ctagacatag atggacaggg agatacgagg ctcatctatg     300
ggacaaaagc tcgtggaatt cgattcagaa caagaaaggc aaacaagttt atctgggagc     360

```
atatgacagc gaggaagcag cagcgcatac gtacgatcta gctgctctca agtactgggg    420
tcccgacacc atcttgaact tccggctga gacgtacaca aaggagttgg aggagatgca    480
gagatgtaca aaggaagagt atttggcttc tctccgccgc cagagcagtg gtttctctag    540
aggcgtctct aaatatcgcg gcgtcgccag gcatcaccat aacggaagat gggaagctag    600
gattggaagg gtgtttggaa caagtactt gtacctcggc acttataata cgcaggagga    660
agctgcagct gcatatgaca tggcggctat agagtacaga ggcgcaaacg cagtgaccaa    720
cttcgacatt agtaactaca tcgaccggtt aaagaaaaaa ggtgtcttcc cattccctgt    780
gagccaagcc aatcatcaag aagctgttct tgctgaagcc aaacaagaag tggaagctaa    840
agaagagcct acagaagaag tgaagcagtg tgtcgaaaaa aagaaccgc aagaagctaa    900
agaagagaag actgagaaaa aacaacaaca acaagaagtg gaggaggcgg tggtcacttg    960
ctgcattgat tcttcggaga gcaatgagct ggcttgggac ttctgtatga tggattcagg   1020
gtttgctccg ttttttgacgg attcaaatct ctcgagtgag aatcccattg agtatcctga   1080
gcttttcaat gagatggggt ttgaggataa cattgacttc atgttcgagg aagggaagca   1140
agactgcttg agcttggaga atctggattg ttgcgatggt gttgttgtgg tgggaagaga   1200
gagcccaact tcattgtcgt cttcaccgtt gtcttgcttg tctactgact ctgcttcatc   1260
aacaacaaca acaacaataa cctctgtttc ttgtaactat tctgtctgag ggggagagc   1320
tttgcatttc taggttgaat tttctatttc ttttgcttct tttttttttg ttgagttctg   1380
ctagggtttg tattctgttt cagggcttac tcattggttc tgacagtcaa tgtttagctc   1440
tcttttccgc tcgtcta                                                  1457

<210> SEQ ID NO 17
<211> LENGTH: 1248
<212> TYPE: DNA
<213> ORGANISM: Brassica napus

<400> SEQUENCE: 17
atgaagagac ccttaaccac ttctccttct acctcctctt ctacttcttc ttcggcttgt     60
atacttccga ctcaaccaga gactccaagg cccaaacgag ccaaaagggc taagaaatct    120
tctattccta ctgatgttaa accacagaat cccaccagtc ctgcctccac cagacgcagc    180
tctatctaca gaggagtcac tagacataga tggacaggga gatacgaggc tcatctatgg    240
gacaaaagct cgtggaattc gattcagaac aagaaaggca acaagtttta tctgggagca    300
tatgacagcg aggaagcagc agcgcatacg tacgatctag ctgctctcaa gtactggggt    360
cccgacacca tcttgaactt ccggctgag acgtacacaa aggagttgga ggagatgcag    420
agatgtacaa aggaagagta tttggcttct ctccgccgcc agagcagtgg tttctctaga    480
ggcgtctcta aatatcgcgg cgtcgccagg catcaccata acggaagatg ggaagctagg    540
attggaaggg tgtttggaaa caagtacttg tacctcggca cttataatac gcaggaggaa    600
gctgcagctg catatgacat ggcggctata gagtacagag gcgcaaacgc agtgaccaac    660
ttcgacatta gtaactacat cgaccggtta aagaaaaaag gtgtcttccc attccctgtg    720
agccaagcca atcatcaaga agctgttctt gctgaagcca acaagaagt ggaagctaaa    780
gaagagccta cagaagaagt gaagcagtgt gtcgaaaaag aagaaccgca agaagctaaa    840
gaagagaaga ctgagaaaaa acaacaacaa caagaagtgg aggaggcggt ggtcacttgc    900
tgcattgatt cttcggagag caatgagctg gcttgggact tctgtatgat ggattcaggg    960
tttgctccgt tttgacgga ttcaaatctc tcgagtgaga atcccattga gtatcctgag   1020
```

-continued

```
cttttcaatg agatggggtt tgaggataac attgacttca tgttcgagga agggaagcaa    1080
gactgcttga gcttggagaa tctggattgt tgcgatggtg ttgttgtggt gggaagagag    1140
agcccaactt cattgtcgtc ttcaccgttg tcttgcttgt ctactgactc tgcttcatca    1200
acaacaacaa caacaataac ctctgtttct tgtaactatt ctgtctga                 1248
```

<210> SEQ ID NO 18
<211> LENGTH: 415
<212> TYPE: PRT
<213> ORGANISM: Brassica napus

<400> SEQUENCE: 18

```
Met Lys Arg Pro Leu Thr Thr Ser Pro Ser Thr Ser Ser Thr Ser
 1               5                  10                  15

Ser Ser Ala Cys Ile Leu Pro Thr Gln Pro Glu Thr Pro Arg Pro Lys
             20                  25                  30

Arg Ala Lys Arg Ala Lys Lys Ser Ser Ile Pro Thr Asp Val Lys Pro
         35                  40                  45

Gln Asn Pro Thr Ser Pro Ala Ser Thr Arg Arg Ser Ser Ile Tyr Arg
     50                  55                  60

Gly Val Thr Arg His Arg Trp Thr Gly Arg Tyr Glu Ala His Leu Trp
 65                  70                  75                  80

Asp Lys Ser Ser Trp Asn Ser Ile Gln Asn Lys Gly Lys Gln Val
                 85                  90                  95

Tyr Leu Gly Ala Tyr Asp Ser Glu Glu Ala Ala Ala His Thr Tyr Asp
                100                 105                 110

Leu Ala Ala Leu Lys Tyr Trp Gly Pro Asp Thr Ile Leu Asn Phe Pro
            115                 120                 125

Ala Glu Thr Tyr Thr Lys Glu Leu Glu Glu Met Gln Arg Cys Thr Lys
        130                 135                 140

Glu Glu Tyr Leu Ala Ser Leu Arg Arg Gln Ser Ser Gly Phe Ser Arg
145                 150                 155                 160

Gly Val Ser Lys Tyr Arg Gly Val Ala Arg His His His Asn Gly Arg
                165                 170                 175

Trp Glu Ala Arg Ile Gly Arg Val Phe Gly Asn Lys Tyr Leu Tyr Leu
            180                 185                 190

Gly Thr Tyr Asn Thr Gln Glu Glu Ala Ala Ala Ala Tyr Asp Met Ala
        195                 200                 205

Ala Ile Glu Tyr Arg Gly Ala Asn Ala Val Thr Asn Phe Asp Ile Ser
    210                 215                 220

Asn Tyr Ile Asp Arg Leu Lys Lys Lys Gly Val Phe Pro Phe Pro Val
225                 230                 235                 240

Ser Gln Ala Asn His Gln Glu Ala Val Leu Ala Glu Ala Lys Gln Glu
                245                 250                 255

Val Glu Ala Lys Glu Glu Pro Thr Glu Glu Val Lys Gln Cys Val Glu
            260                 265                 270

Lys Glu Glu Pro Gln Glu Ala Lys Glu Glu Lys Thr Glu Lys Lys Gln
        275                 280                 285

Gln Gln Gln Glu Val Glu Glu Ala Val Val Thr Cys Cys Ile Asp Ser
    290                 295                 300

Ser Glu Ser Asn Glu Leu Ala Trp Asp Phe Cys Met Met Asp Ser Gly
305                 310                 315                 320

Phe Ala Pro Phe Leu Thr Asp Ser Asn Leu Ser Ser Glu Asn Pro Ile
                325                 330                 335
```

-continued

Glu Tyr Pro Glu Leu Phe Asn Glu Met Gly Phe Glu Asp Asn Ile Asp
              340                 345                 350

Phe Met Phe Glu Glu Gly Lys Gln Asp Cys Leu Ser Leu Glu Asn Leu
          355                 360                 365

Asp Cys Cys Asp Gly Val Val Val Gly Arg Glu Ser Pro Thr Ser
370                 375                 380

Leu Ser Ser Ser Pro Leu Ser Cys Leu Ser Thr Asp Ser Ala Ser Ser
385                 390                 395                 400

Thr Thr Thr Thr Thr Ile Thr Ser Val Ser Cys Asn Tyr Ser Val
                  405                 410                 415

<210> SEQ ID NO 19
<211> LENGTH: 1389
<212> TYPE: DNA
<213> ORGANISM: Brassica napus
<220> FEATURE:
<221> NAME/KEY: modified_base
<222> LOCATION: (1318)
<223> OTHER INFORMATION: a, c, g, t, unknown or other
<220> FEATURE:
<221> NAME/KEY: modified_base
<222> LOCATION: (1342)
<223> OTHER INFORMATION: a, c, g, t, unknown or other
<220> FEATURE:
<221> NAME/KEY: modified_base
<222> LOCATION: (1346)
<223> OTHER INFORMATION: a, c, g, t, unknown or other
<220> FEATURE:
<221> NAME/KEY: modified_base
<222> LOCATION: (1354)
<223> OTHER INFORMATION: a, c, g, t, unknown or other
<220> FEATURE:
<221> NAME/KEY: modified_base
<222> LOCATION: (1374)
<223> OTHER INFORMATION: a, c, g, t, unknown or other
<220> FEATURE:
<221> NAME/KEY: modified_base
<222> LOCATION: (1386)
<223> OTHER INFORMATION: a, c, g, t, unknown or other

<400> SEQUENCE: 19
agagtatttg ggacacgtgg tggaatcttc cggtggtccg gagcttggtt ttcacggtgg      60
agctaacaac ggaggagctt tgtcacttgg tgttaacgtt aacaactcta atcacaggac     120
tagtgatgat catactcaga tcactgagta tcattaccga ggaaataaca atggtgaaag     180
aaccaacaac gagaagacgg tttctgagaa ggagaagcct gttgtggctg tggagacatc     240
agattgttct aacaagaaga tcgctgatac gtttggacaa aggacttcca tctacagagg     300
agttacaaga catagatgga cgggaagata tgaagctcat ctatgggata atagctgtag     360
gcgagaaggt caagccagga aaggacgtca agtatacttg ggtggatatg acaaagaaga     420
caaggcagct cgagcttatg attatagcag ctcttaagta ctggaatgct actgctacca     480
ccaatttccc tattcaaaac tactcaaaag aactagagga aatgaagcac atgaccaaac     540
aagagttcat tgcttcccctt aggaggaaga gtagcggatt ctctagagga gcctcaatat     600
acagaggtgt gacaaggcat catcaacaag gacgttggca agcaaggata ggccgtgtag     660
ccgggaacaa agatctttac ctaggaacat ttgcaacgga agaggaagca gccgaggcat     720
acgacatagc agcgatcaaa ttcagggaa taaacgctgt aacaaacttt gagatgaacc     780
gttacgacgt tgaggccatc atgaagagtg cacttcccat tggtggtgca gcaaaacgtc     840
ttaagctctc tttagaagct gcagagcaga accaatcct cggtcatcaa catcaactcc     900
accacttcca gcaacaacag cagcaacaga ttcagtcctc tccgaaccac agtagcatta     960
acttcgctca atctcagatg attcctgtgg gatccctttt gaagctgctg ctctctacca    1020

```
tcatcaacag caacaacagc agcagcagca acagaacttc ttccagcatt ttccggcgaa   1080
tgttcgagct actgactcga ccggttctaa taataactcc aacgttcaag gttcaatggg   1140
acttatggtg ccgaatcagg ctgagttctt cctctggcct aaccagtctt actagaatca   1200
atcatgttat gttttttgtt tttttttttt tgttttagtt tttaatggtt tttaagggat   1260
aacaacttct ttctaatgtt caacttcttg attctagcta accccataag ctgactanaa   1320
ggatatgaaa atctcacttg tnccgngtta ctcngtttcc atttaatgaa atgngtttct   1380 gtttangta                                                           1389
```

<210> SEQ ID NO 20  
<211> LENGTH: 1113  
<212> TYPE: DNA  
<213> ORGANISM: Brassica napus

<400> SEQUENCE: 20

```
atgatcatac tcagatcact gagtatcatt accgaggaaa taacaatggt gaaagaacca     60
acaacgagaa gacggtttct gagaaggaga agcctgttgt ggctgtggag acatcagatt    120
gttctaacaa gaagatcgct gatacgtttg gacaaaggac ttccatctac agaggagtta    180
caagacatag atggacggga agatatgaag ctcatctatg ggataatagc tgtaggcgag    240
aaggtcaagc caggaaagga cgtcaagtat acttgggtgg atatgacaaa gaagacaagg    300
cagctcgagc ttatgattat agcagctctt aagtactgga atgctactgc taccaccaat    360
ttccctatta caaactactc aaaagaacta gaggaaatga agcacatgac aaacaagag    420 ttcattgctt cccttaggag gaagagtagc ggattctcta gaggagcctc aatatacaga    480
ggtgtgacaa gcatcatca acaaggacgt tggcaagcaa ggataggccg tgtagccggg    540
aacaaagatc tttacctagg aacatttgca acggaagagg aagcagccga gcatacgac    600 atagcagcga tcaaattcag gggaataaac gctgtaacaa actttgagat gaaccgttac    660
gacgttgagg ccatcatgaa gagtgcactt cccattggtg gtgcagcaaa acgtcttaag    720
ctctctttag aagctgcaga gcagaaacca atcctcggtc atcaacatca actccaccac    780
ttccagcaac aacagcagca acagattcag tcctctccga accacagtag cattaacttc    840
gctcaatctc agatgattcc tgtgggatcc cttttgaagc tgctgctctc taccatcatc    900
aacagcaaca acagcagcag cagcaacaga acttcttcca gcattttccg gcgaatgttc    960
gagctactga ctcgaccggt tctaataata actccaacgt tcaaggttca atgggactta   1020
tggtgccgaa tcaggctgag ttcttcctct ggcctaacca gtcttactag aatcaatcat   1080
gttatgtttt tgttttttt tttttgttt tag                                  1113
```

<210> SEQ ID NO 21  
<211> LENGTH: 370  
<212> TYPE: PRT  
<213> ORGANISM: Brassica napus

<400> SEQUENCE: 21

```
Met Ile Ile Leu Arg Ser Leu Ser Ile Ile Thr Glu Glu Ile Thr Met
  1               5                  10                  15

Val Lys Glu Pro Thr Thr Arg Arg Arg Phe Leu Arg Arg Arg Ser Leu
                 20                  25                  30

Leu Trp Leu Trp Arg His Gln Ile Val Leu Thr Arg Arg Ser Leu Ile
             35                  40                  45

Arg Leu Asp Lys Gly Leu Pro Ser Thr Glu Glu Leu Gln Asp Ile Asp
         50                  55                  60
```

Gly Arg Glu Asp Met Lys Leu Ile Tyr Gly Ile Ile Ala Val Gly Glu
65                  70                  75                  80

Lys Val Lys Pro Gly Lys Asp Val Lys Tyr Thr Trp Val Asp Met Thr
            85                  90                  95

Lys Lys Thr Arg Gln Leu Glu Leu Met Ile Ile Ala Ala Leu Lys Tyr
        100                 105                 110

Trp Asn Ala Thr Ala Thr Thr Asn Phe Pro Ile Thr Asn Tyr Ser Lys
    115                 120                 125

Glu Leu Glu Glu Met Lys His Met Thr Lys Gln Glu Phe Ile Ala Ser
130                 135                 140

Leu Arg Arg Lys Ser Ser Gly Phe Ser Arg Gly Ala Ser Ile Tyr Arg
145                 150                 155                 160

Gly Val Thr Arg His His Gln Gln Gly Arg Trp Gln Ala Arg Ile Gly
                165                 170                 175

Arg Val Ala Gly Asn Lys Asp Leu Tyr Leu Gly Thr Phe Ala Thr Glu
            180                 185                 190

Glu Glu Ala Ala Glu Ala Tyr Asp Ile Ala Ala Ile Lys Phe Arg Gly
        195                 200                 205

Ile Asn Ala Val Thr Asn Phe Glu Met Asn Arg Tyr Asp Val Glu Ala
210                 215                 220

Ile Met Lys Ser Ala Leu Pro Ile Gly Gly Ala Ala Lys Arg Leu Lys
225                 230                 235                 240

Leu Ser Leu Glu Ala Ala Glu Gln Lys Pro Ile Leu Gly His Gln His
                245                 250                 255

Gln Leu His His Phe Gln Gln Gln Gln Gln Ile Gln Ser Ser
            260                 265                 270

Pro Asn His Ser Ser Ile Asn Phe Ala Gln Ser Gln Met Ile Pro Val
            275                 280                 285

Gly Ser Leu Leu Lys Leu Leu Leu Ser Thr Ile Ile Asn Ser Asn Asn
        290                 295                 300

Ser Ser Ser Ser Asn Arg Thr Ser Ser Ser Ile Phe Arg Arg Met Phe
305                 310                 315                 320

Glu Leu Leu Thr Arg Pro Val Leu Ile Ile Thr Pro Thr Phe Lys Val
                325                 330                 335

Gln Trp Asp Leu Trp Cys Arg Ile Arg Leu Ser Ser Ser Gly Leu
            340                 345                 350

Thr Ser Leu Thr Arg Ile Asn His Val Met Phe Phe Val Phe Phe Phe
        355                 360                 365

Leu Phe
370

<210> SEQ ID NO 22
<211> LENGTH: 1892
<212> TYPE: DNA
<213> ORGANISM: Glycine max

<400> SEQUENCE: 22
aagcagtggt aacaacgcag agtacgcggg attcaagtac ttcttctttg taaccaaact     60
aaaacctctt gatttattgt ttcatttaat caaatagtag taataatatc accaccgcac    120
cgacatggag tagaagtagc tcttcattca aagagtaacg cctctccaga gactagtact    180
tcattttgca ccattgatat ctcaaatggc tcgtgcttcg actaactggc tatcgttctc    240
tctctccccc atgaaaatgc tccgaacccc cgaacctcag ttcgttcaat acgacgccgc    300
ttccgacact tcctcgcatc actactacct cgacaacttg tacaccaacg ggtgggggaa    360

```
cgggagcctc aagtttgagc agaatctgaa ccacagcgac gtgagtttcg ttgaatcgtc      420
gtcgcagagc gtcagccacg cgccgccgaa gctggaggat tttctcggcg actcctccgc      480
tgttatgcgt tactccgaca gccagacgga gacgcaggac tcgtcgctga cgcacatcta      540
cgaccaccac caccaccacc accaccacca ccaccacggt tcttctgcgt acttcggcgg      600
tgaccaccag gatctcaagg ccattactgg attccaagct ttttcgacta actctggctc      660
cgaggttgat gattctgcat cgatcggaaa ggcgcagggc agcgagttcg ggactcactc      720
tattgagtcc tccgtcaacg agttcgccgc gttctccggt ggcaccaaca ccggtggaac      780
cttgtcgctc gccgtcgcgc agagctccga aaggccgtc gctgctgcgg cggagtccga      840
tcgctcgaag aaggttgtgg ataccttcgg ccagcggact tctatataca gaggtgtcac      900
taggcaccga tggacaggaa gatatgaagc gcatctatgg gacaatagtt gcagaaggga      960
gggtcaagct agaaaagggc gtcaagttta tttgggtgga tatgataagg aagaaaaggc     1020
cgctagatct tatgatttgg cagctctgaa gtactgggg cccactgcta ccaccaactt     1080
ccctgtttcc aattattcaa aggaagtgga ggagatgaaa catgtaacaa gcaggaatt     1140 tatcgcatca ttgcgaagga aaagtagtgg tttctccagg ggagcttcca tatacagagg     1200
tgttacaagg catcatcaac agggtaggtg gcaagcaaga attggccgtg tagctggaaa     1260
caaagatctt tacttgggaa cattcgcaac cgaggaggaa gcagcagagg catatgatat     1320
tgcagccatt aagttcagag gtgcaaacgc ggtaaccaac tttgagatga atagatatga     1380
tgtggaagct ataatgaaga gttctcttcc agtgggtggg gcagcaaagc gcttgaagct     1440
ttcccttgaa tcagagcaga agctcttcc tgtgagcagc agcagcagca gcaatcaaca     1500
gcagaatcca cagtgtggaa acgtgagtgc cagcatcaat ttctcatcca ttcatcagcc     1560
aattgcttct atcccttgtg gaattccctt tgattcaaca acagcatatt atcatcacaa     1620 cctttttccaa cattttcacc ctaccaacgc tggcacagca gcgtctgctg ttacttctgc     1680
caatgcaaat gcactaactg cactgccacc aacagcagca gctgagttct ttatttggcc     1740
tcatcagtct tattgaaaaa agaaaaagaa aaaaagagg aggttttga gttggctagt     1800 cttggttaca gtaggaagct ggatatgtaa ctaactgctt aagaaatgag aaatatttcg     1860
tgcatcataa ttttgcacaa gaaaaaaaaa ga                                  1892
```

<210> SEQ ID NO 23
<211> LENGTH: 1551
<212> TYPE: DNA
<213> ORGANISM: Glycine max

<400> SEQUENCE: 23

```
atggctcgtg cttcgactaa ctggctatcg ttctctctct cccccatgga aatgctccga       60
acccccgaac ctcagttcgt tcaatacgac gccgcttccg acacttcctc gcatcactac      120
tacctcgaca acttgtacac caacgggtgg gggaacggga gcctcaagtt tgagcagaat      180
ctgaaccaca gcgacgtgag tttcgttgaa tcgtcgtcgc agagcgtcag ccacgcgccg      240
ccgaagctgg aggattttct cggcgactcc tccgctgtta tgcgttactc cgacagccag      300
acggagacgc aggactcgtc gctgacgcac atctacgacc accaccacca ccaccaccac      360
caccaccacc acggttcttc tgcgtacttc ggcggtgacc accaggatct caaggccatt      420
actggattcc aagctttttc gactaactct ggctccgagg ttgatgattc tgcatcgatc      480
ggaaaggcgc agggcagcga gttcgggact cactctattg agtcctccgt caacgagttc      540
gccgcgttct ccggtggcac caacaccggt ggaaccttgt cgctcgccgt cgcgcagagc      600
```

```
tccgagaagg ccgtcgctgc tgcggcggag tccgatcgct cgaagaaggt tgtggatacc      660
ttcggccagc ggacttctat atacagaggt gtcactaggc accgatggac aggaagatat      720
gaagcgcatc tatgggacaa tagttgcaga agggagggtc aagctagaaa agggcgtcaa      780
gtttatttgg gtggatatga taaggaagaa aaggccgcta gatcttatga tttggcagct      840
ctgaagtact ggggtcccac tgctaccacc aacttccctg tttccaatta ttcaaaggaa      900
gtggaggaga tgaaacatgt aacaaagcag gaatttatcg catcattgcg aaggaaaagt      960
agtggtttct ccaggggagc ttccatatac agaggtgtta caaggcatca tcaacagggt     1020
aggtggcaag caagaattgg ccgtgtagct ggaaacaaag atctttactt gggaacattc     1080
gcaaccgagg aggaagcagc agaggcatat gatattgcag ccattaagtt cagaggtgca     1140
aacgcggtaa ccaactttga gatgaataga tatgatgtgg aagctataat gaagagttct     1200
cttccagtgg gtggggcagc aaagcgcttg aagctttccc ttgaatcaga gcagaaagct     1260
cttcctgtga gcagcagcag cagcagcaat caacagcaga atccacagtg tggaaacgtg     1320
agtgccagca tcaatttctc atccattcat cagccaattg cttctatccc ttgtggaatt     1380
ccctttgatt caacaacagc atattatcat cacaaccttt ccaacatttt tcaccctacc     1440
aacgctggca cagcagcgtc tgctgttact tctgccaatg caaatgcact aactgcactg     1500
ccaccaacag cagcagctga gttctttatt tggcctcatc agtcttattg a              1551
```

<210> SEQ ID NO 24
<211> LENGTH: 516
<212> TYPE: PRT
<213> ORGANISM: Glycine max

<400> SEQUENCE: 24

```
Met Ala Arg Ala Ser Thr Asn Trp Leu Ser Phe Ser Leu Ser Pro Met
  1               5                  10                  15

Glu Met Leu Arg Thr Pro Glu Pro Gln Phe Val Gln Tyr Asp Ala Ala
                 20                  25                  30

Ser Asp Thr Ser Ser His His Tyr Tyr Leu Asp Asn Leu Tyr Thr Asn
             35                  40                  45

Gly Trp Gly Asn Gly Ser Leu Lys Phe Glu Gln Asn Leu Asn His Ser
         50                  55                  60

Asp Val Ser Phe Val Glu Ser Ser Gln Ser Val Ser His Ala Pro
 65                  70                  75                  80

Pro Lys Leu Glu Asp Phe Leu Gly Asp Ser Ser Ala Val Met Arg Tyr
                 85                  90                  95

Ser Asp Ser Gln Thr Glu Thr Gln Asp Ser Ser Leu Thr His Ile Tyr
            100                 105                 110

Asp His His His His His His His His His Gly Ser Ser Ala
        115                 120                 125

Tyr Phe Gly Gly Asp His Gln Asp Leu Lys Ala Ile Thr Gly Phe Gln
    130                 135                 140

Ala Phe Ser Thr Asn Ser Gly Ser Glu Val Asp Asp Ser Ala Ser Ile
145                 150                 155                 160

Gly Lys Ala Gln Gly Ser Glu Phe Gly Thr His Ser Ile Glu Ser Ser
                165                 170                 175

Val Asn Glu Phe Ala Ala Phe Ser Gly Gly Thr Asn Thr Gly Gly Thr
            180                 185                 190

Leu Ser Leu Ala Val Ala Gln Ser Ser Glu Lys Ala Val Ala Ala Ala
        195                 200                 205
```

```
Ala Glu Ser Asp Arg Ser Lys Lys Val Val Asp Thr Phe Gly Gln Arg
        210                 215                 220
Thr Ser Ile Tyr Arg Gly Val Thr Arg His Arg Trp Thr Gly Arg Tyr
225                 230                 235                 240
Glu Ala His Leu Trp Asp Asn Ser Cys Arg Arg Glu Gly Gln Ala Arg
                245                 250                 255
Lys Gly Arg Gln Val Tyr Leu Gly Gly Tyr Asp Lys Glu Glu Lys Ala
            260                 265                 270
Ala Arg Ser Tyr Asp Leu Ala Ala Leu Lys Tyr Trp Gly Pro Thr Ala
        275                 280                 285
Thr Thr Asn Phe Pro Val Ser Asn Tyr Ser Lys Glu Val Glu Glu Met
290                 295                 300
Lys His Val Thr Lys Gln Glu Phe Ile Ala Ser Leu Arg Arg Lys Ser
305                 310                 315                 320
Ser Gly Phe Ser Arg Gly Ala Ser Ile Tyr Arg Gly Val Thr Arg His
                325                 330                 335
His Gln Gln Gly Arg Trp Gln Ala Arg Ile Gly Arg Val Ala Gly Asn
            340                 345                 350
Lys Asp Leu Tyr Leu Gly Thr Phe Ala Thr Glu Glu Ala Ala Glu
        355                 360                 365
Ala Tyr Asp Ile Ala Ala Ile Lys Phe Arg Gly Ala Asn Ala Val Thr
    370                 375                 380
Asn Phe Glu Met Asn Arg Tyr Asp Val Glu Ala Ile Met Lys Ser Ser
385                 390                 395                 400
Leu Pro Val Gly Gly Ala Ala Lys Arg Leu Lys Leu Ser Leu Glu Ser
                405                 410                 415
Glu Gln Lys Ala Leu Pro Val Ser Ser Ser Ser Ser Asn Gln Gln
            420                 425                 430
Gln Asn Pro Gln Cys Gly Asn Val Ser Ala Ser Ile Asn Phe Ser Ser
        435                 440                 445
Ile His Gln Pro Ile Ala Ser Ile Pro Cys Gly Ile Pro Phe Asp Ser
450                 455                 460
Thr Thr Ala Tyr Tyr His His Asn Leu Phe Gln His Phe His Pro Thr
465                 470                 475                 480
Asn Ala Gly Thr Ala Ala Ser Ala Val Thr Ser Ala Asn Ala Asn Ala
                485                 490                 495
Leu Thr Ala Leu Pro Pro Thr Ala Ala Ala Glu Phe Phe Ile Trp Pro
            500                 505                 510
His Gln Ser Tyr
        515

<210> SEQ ID NO 25
<211> LENGTH: 2088
<212> TYPE: DNA
<213> ORGANISM: Glycine max

<400> SEQUENCE: 25
gatagattgc agtttccaaa gaacccaact caacttcaaa accccataat aatctctctt      60
tgacattcat aaaaaacaca caccatggac tcttgttcat caccgccaaa caacaactcc     120
ctcgctttct ctcttttccaa tcactttccc aaccctcct cctctcccct ctcccttttc     180
cactccttca cctatccatc tctctctctc acaggaagcc acacggcgga tgcacctcct     240
gagcccatcg ccggcggagg agcgaccaac ctctccatat tcaccggcgc ccccaagttc     300
gaggactttc tgggcggttc ctccgcaaca gccaccgcca ccacgtgtgc accgccacag     360
```

```
cttccgcagt tctccaccga caacaacaac cacctgtacg attcggagct gaagacaaca      420
atagccgcgt gcttccctcg cgcctttgcc gccgaaccaa ccaccgaacc tcagaaaccc      480
tctccaaaga aaccgtcga caccttcggc caacgcacct ccatctaccg cggcgtcacc      540
cgacatagat ggacgggaag atacgaagct catctatggg acaatagttg tagaagagaa      600
ggccaaagca ggaaaggaag acaagtttac ctgggtggtt atgacaagga agataaggca      660
gccagggctt acgatctcgc agctctcaag tactggggtc caactaccac caccaacttt      720
cccatttcca actatgagaa ggaactggag gagatgaaga acatgaccag gcaagagttt      780
gttgcttctc tacgaaggaa gagcagtggt ttctctaggg gggcctctat atacagagga      840
gtgacgagac accaccagca tggccgatgg caggcgagaa taggcagagt tgccggaaac      900
aaagacctct accttggaac tttcagcacc caagaagaag ctgctgaggc ctatgacatt      960
gctgctatca aattcagggg attaaatgca gtcacaaact ttgacatgag tcgctacgat     1020
gtaaagagca ttgcaaatag cactcttcca attggaggtt tatctggcaa gaacaagaac     1080
tccacagatt ctgcatctga gcaagagc cacgaggcaa gccgatccga cgaacgagat      1140
ccatcagcgg cttcatccgt gacctttgca tcacagcaac agccttcgag ctccacctta     1200
agctttgcca tacccattaa gcaagaccct tcagattact ggtccatcct ggggtaccat     1260
aattctcccc ttgacaacac tggcatcagg aacactacta gtgttactgc aacttctttt     1320
ccatcctcca acaatggcac tactagtagt ttgacaccct tccacatgga attctcaaat     1380
gcccccacaa gtaccggcag tgataacgat gccgcgtttt tcagtggagg aggcatcttt     1440
gttcagcaac aaagtggtca tggtaatggt catggaagtg gaagcagtgg ttcctcctct     1500
tcttctttaa gctgttcaat cccattcgcc acgcccatct tttctctaaa tagcaatact     1560
agttatgaga acagtgctgg ttatggaaac tggattggac ctaccctgca cacattccaa     1620
tcccatgcaa aaccaagtct ctttcaaacg ccaatatttg gaatggaatg agctcatgca     1680
cgaggtggga tgagaatctg tgcatataat gatgaaaggg gaagggcaat agtggtgatg     1740
gtgttttagc atgcaaaaga agcaaggacg aactagtacc tttagctgat gcagtatttg     1800
aatgagttgg actgacagtc ataatttcat gagaagcgta gctataccta gcagcagctg     1860
acactgtact aactcaaagt tccttttgtta tgttttggat gaattttctt tttttttctttt     1920 ttcgcccсcсt tttagctttt ttgtccctgt taatatactg acatcatttc aaatgagtat     1980
aatgggaaga aaaagaaaa tccttttgta atcccctttc atctcatttt tgttagtatt     2040
aaaaacttgc tatatctatg cgaaaggcat tcaatgccta tatataga                 2088
```

<210> SEQ ID NO 26
<211> LENGTH: 1587
<212> TYPE: DNA
<213> ORGANISM: Glycine max

<400> SEQUENCE: 26

```
atggactctt gttcatcacc gccaaacaac aactccctcg ctttctctct ttccaatcac       60
tttcccaacc cttcctcctc tcccctctcc cttttccact ccttcaccta tccatctctc      120
tctctcacag gaagccacac ggcggatgca cctcctgagc ccatcgccgg cggaggagcg      180
accaacctct ccatattcac cggcgccccc aagttcgagg actttctggg cggttcctcc      240
gcaacagcca ccgccaccac gtgtgcaccg ccacagcttc gcagttctc caccgacaac      300 aacaaccacc tgtacgattc ggagctgaag acaacaatag ccgcgtgctt ccctcgcgcc      360
tttgccgccg aaccaaccac cgaacctcag aaaccctctc caagaaaaac cgtcgacacc      420
```

-continued

```
ttcggccaac gcacctccat ctaccgcggc gtcacccgac atagatggac gggaagatac    480
gaagctcatc tatgggacaa tagttgtaga agagaaggcc aaagcaggaa aggaagacaa    540
gtttacctgg gtggttatga caaggaagat aaggcagcca gggcttacga tctcgcagct    600
ctcaagtact ggggtccaac taccaccacc aactttccca tttccaacta tgagaaggaa    660
ctggaggaga tgaagaacat gaccaggcaa gagtttgttg cttctctacg aaggaagagc    720
agtggtttct ctaggggggc ctctatatac agaggagtga cgagacacca ccagcatggc    780
cgatggcagg cgagaatagg cagagttgcc ggaaacaaag acctctacct tggaactttc    840
agcacccaag aagaagctgc tgaggcctat gacattgctg ctatcaaatt caggggatta    900
aatgcagtca caaactttga catgagtcgc tacgatgtaa agagcattgc aaatagcact    960
cttccaattg gaggtttatc tggcaagaac aagaactcca cagattctgc atctgagagc   1020
aagagccacg aggcaagccg atccgacgaa cgagatccat cagcggcttc atccgtgacc   1080
tttgcatcac agcaacagcc ttcgagctcc accttaagct tgccataccc cattaagcaa   1140
gacccttcag attactggtc catcctgggg taccataatt ctccccttga caacactggc   1200
atcaggaaca ctactagtgt tactgcaact tcttttccat cctccaacaa tggcactact   1260
agtagtttga caccccttcca catggaattc tcaaatgccc ccacaagtac cggcagtgat   1320
aacgatgccg cgttttttcag tggaggaggc atctttgttc agcaacaaag tggtcatggt   1380
aatggtcatg gaagtggaag cagtggttcc tcctcttctt ctttaagctg ttcaatccca   1440
ttcgccacgc ccatcttttc tctaaatagc aatactagtt atgagaacag tgctggttat   1500
ggaaactgga ttggacctac cctgcacaca ttccaatccc atgcaaaacc aagtctcttt   1560
caaacgccaa tatttggaat ggaatga                                        1587
```

<210> SEQ ID NO 27
<211> LENGTH: 528
<212> TYPE: PRT
<213> ORGANISM: Glycine max

<400> SEQUENCE: 27

```
Met Asp Ser Cys Ser Ser Pro Asn Asn Ser Leu Ala Phe Ser
  1               5                  10                  15

Leu Ser Asn His Phe Pro Asn Pro Ser Ser Pro Leu Ser Leu Phe
                 20                  25                  30

His Ser Phe Thr Tyr Pro Ser Leu Ser Leu Thr Gly Ser His Thr Ala
             35                  40                  45

Asp Ala Pro Pro Glu Pro Ile Ala Gly Gly Ala Thr Asn Leu Ser
         50                  55                  60

Ile Phe Thr Gly Ala Pro Lys Phe Glu Asp Phe Leu Gly Gly Ser Ser
 65                  70                  75                  80

Ala Thr Ala Thr Ala Thr Thr Cys Ala Pro Pro Gln Leu Pro Gln Phe
                 85                  90                  95

Ser Thr Asp Asn Asn Asn His Leu Tyr Asp Ser Glu Leu Lys Thr Thr
            100                 105                 110

Ile Ala Ala Cys Phe Pro Arg Ala Phe Ala Ala Glu Pro Thr Thr Glu
            115                 120                 125

Pro Gln Lys Pro Ser Pro Lys Lys Thr Val Asp Thr Phe Gly Gln Arg
        130                 135                 140

Thr Ser Ile Tyr Arg Gly Val Thr Arg His Arg Trp Thr Gly Arg Tyr
145                 150                 155                 160

Glu Ala His Leu Trp Asp Asn Ser Cys Arg Arg Glu Gly Gln Ser Arg
                165                 170                 175
```

| Lys | Gly | Arg | Gln | Val | Tyr | Leu | Gly | Gly | Tyr | Asp | Lys | Glu | Asp | Lys | Ala |
| | | | 180 | | | | | 185 | | | | | 190 | | |

| Ala | Arg | Ala | Tyr | Asp | Leu | Ala | Ala | Leu | Lys | Tyr | Trp | Gly | Pro | Thr | Thr |
| | | 195 | | | | | 200 | | | | | 205 | | | |

| Thr | Thr | Asn | Phe | Pro | Ile | Ser | Asn | Tyr | Glu | Lys | Glu | Leu | Glu | Glu | Met |
| 210 | | | | | | 215 | | | | | 220 | | | | |

| Lys | Asn | Met | Thr | Arg | Gln | Glu | Phe | Val | Ala | Ser | Leu | Arg | Arg | Lys | Ser |
| 225 | | | | | 230 | | | | | 235 | | | | | 240 |

| Ser | Gly | Phe | Ser | Arg | Gly | Ala | Ser | Ile | Tyr | Arg | Gly | Val | Thr | Arg | His |
| | | | | 245 | | | | | 250 | | | | | 255 | |

| His | Gln | His | Gly | Arg | Trp | Gln | Ala | Arg | Ile | Gly | Arg | Val | Ala | Gly | Asn |
| | | | 260 | | | | | 265 | | | | | 270 | | |

| Lys | Asp | Leu | Tyr | Leu | Gly | Thr | Phe | Ser | Thr | Gln | Glu | Glu | Ala | Ala | Glu |
| | | 275 | | | | | 280 | | | | | 285 | | | |

| Ala | Tyr | Asp | Ile | Ala | Ala | Ile | Lys | Phe | Arg | Gly | Leu | Asn | Ala | Val | Thr |
| 290 | | | | | | 295 | | | | | 300 | | | | |

| Asn | Phe | Asp | Met | Ser | Arg | Tyr | Asp | Val | Lys | Ser | Ile | Ala | Asn | Ser | Thr |
| 305 | | | | | 310 | | | | | 315 | | | | | 320 |

| Leu | Pro | Ile | Gly | Gly | Leu | Ser | Gly | Lys | Asn | Lys | Asn | Ser | Thr | Asp | Ser |
| | | | | 325 | | | | | 330 | | | | | 335 | |

| Ala | Ser | Glu | Ser | Lys | Ser | His | Glu | Ala | Ser | Arg | Ser | Asp | Glu | Arg | Asp |
| | | | 340 | | | | | 345 | | | | | 350 | | |

| Pro | Ser | Ala | Ala | Ser | Ser | Val | Thr | Phe | Ala | Ser | Gln | Gln | Gln | Pro | Ser |
| | | 355 | | | | | 360 | | | | | 365 | | | |

| Ser | Ser | Thr | Leu | Ser | Phe | Ala | Ile | Pro | Ile | Lys | Gln | Asp | Pro | Ser | Asp |
| 370 | | | | | | 375 | | | | | 380 | | | | |

| Tyr | Trp | Ser | Ile | Leu | Gly | Tyr | His | Asn | Ser | Pro | Leu | Asp | Asn | Thr | Gly |
| 385 | | | | | 390 | | | | | 395 | | | | | 400 |

| Ile | Arg | Asn | Thr | Thr | Ser | Val | Thr | Ala | Thr | Ser | Phe | Pro | Ser | Ser | Asn |
| | | | | 405 | | | | | 410 | | | | | 415 | |

| Asn | Gly | Thr | Thr | Ser | Ser | Leu | Thr | Pro | Phe | His | Met | Glu | Phe | Ser | Asn |
| | | | 420 | | | | | 425 | | | | | 430 | | |

| Ala | Pro | Thr | Ser | Thr | Gly | Ser | Asp | Asn | Asp | Ala | Ala | Phe | Phe | Ser | Gly |
| | | 435 | | | | | 440 | | | | | 445 | | | |

| Gly | Gly | Ile | Phe | Val | Gln | Gln | Gln | Ser | Gly | His | Gly | Asn | Gly | His | Gly |
| 450 | | | | | | 455 | | | | | 460 | | | | |

| Ser | Gly | Ser | Ser | Gly | Ser | Ser | Ser | Ser | Leu | Ser | Cys | Ser | Ile | Pro |
| 465 | | | | | 470 | | | | | 475 | | | | | 480 |

| Phe | Ala | Thr | Pro | Ile | Phe | Ser | Leu | Asn | Ser | Asn | Thr | Ser | Tyr | Glu | Asn |
| | | | | 485 | | | | | 490 | | | | | 495 | |

| Ser | Ala | Gly | Tyr | Gly | Asn | Trp | Ile | Gly | Pro | Thr | Leu | His | Thr | Phe | Gln |
| | | | 500 | | | | | 505 | | | | | 510 | | |

| Ser | His | Ala | Lys | Pro | Ser | Leu | Phe | Gln | Thr | Pro | Ile | Phe | Gly | Met | Glu |
| | | 515 | | | | | 520 | | | | | 525 | | | |

<210> SEQ ID NO 28
<211> LENGTH: 1683
<212> TYPE: DNA
<213> ORGANISM: Glycine max

<400> SEQUENCE: 28

```
cctcttgatt tattgtttca tttaatcaaa tagtagtaat aatatcacca ccgcgccgac    60
atggagtaga agtagctctt cattcaaaga gtaacgcctc tccagagact agtacttcat   120
tttgcaccat tgatatctca aatggctcgt gcttcgacta actggctatc gttctctctc   180
```

```
tcccccatgg aaatgctccg aaccccgaa cctcagttcg ttcaatacga cgccgcttcc    240
gacacttcct cgcatcacta ctacctcgac aacttgtaca ccaacgggtg ggggaacggg    300
agcctcaagt ttgagcagaa tctgaaccac agcgacgtga gtttcgttga atcgtcgtcg    360
cagagcgtca gccacgcgcc gccgaagctg gaggattttc tcggcgactc ctccgctgtt    420
atgcgttact ccgacagcca gacggagacg caggactcgt cgctgacgca catctacgac    480
caccaccacc accaccacca ccaccaccac cacggttctt ctgcgtactt cggcggtgac    540
caccaggatc tcaaggccat tactggattc aagcttttt cgactaactc tggctccgag    600
gttgatgatt ctgcatcgat cggaaaggcg cagggcagcg agttcgggac tcactctatt    660
gagtcctccg tcaacgagtt cgccgcgttc tccggtggca ccaacaccgg tggaaccttg    720
tcgctcgccg tcgcgcagag ctccgagaag gccgtcgctg ctgcggcgga gtccgatcgc    780
tcgaagaagg ttgtggatac cttcggccag cggacttcta tatacagagg tgtcactagg    840
caccgatgga caggaagata tgaagcgcat ctatgggaca atagttgcag aagggagggt    900
caagccagaa aagggcgtca agtttatttg ggtggatatg ataaggaaga aaaggccgcg    960
agagcttatg atttggcagc tctaaagtac tggggtccca ctgctaccac caacttccct   1020
gtttccaatt attcgaagga agtggaggag atgaaacatg taacaaagca agaatttatt   1080
gcatcattgc ggaggaaaag tagtggtttc tccaggggag cttccatata cagaggtgtt   1140
acaaggcatc atcaacaggg taggtggcaa gcaagaattg ccgtgtagc tggaaacaaa   1200 gatttatact tgggaacatt cgcaaccgag gaggaagcag cagaggcata tgatattgca   1260
gccataaagt tcagaggtgc aaacgcggta accaactttg agatgaatag atatgatgtg   1320
gaagctataa tgaagagttc tcttccagtg ggtggggcaa caaacgctt gaggctttcc   1380 cttgaatcag agcagaaagc tcctcctgtg aacagcagca gtcagcagca gaatccacag   1440
tgtggtaacg tgagtggtag catcaatttc tcagccattc atcagccaat tgcttcaatc   1500
ccttgtggaa ttccgtttga ttcaacaaca gcatattatc ctcacaacct tttccaacat   1560
tttcacccta ccaacgctgg tgcagcagcg tctgctgtta cttctgccaa tgcaaccgca   1620
ctaactgcac tgccagcatc agcagcaact gagttcttta tttggcctca tcagtcttat   1680
tga                                                                 1683
```

<210> SEQ ID NO 29
<211> LENGTH: 1542
<212> TYPE: DNA
<213> ORGANISM: Glycine max

<400> SEQUENCE: 29

```
atggctcgtg cttcgactaa ctggctatcg ttctctctct cccccatgga aatgctccga     60 accccgaac ctcagttcgt tcaatacgac gccgcttccg acacttcctc gcatcactac    120
tacctcgaca acttgtacac caacgggtgg gggaacggga gcctcaagtt tgagcagaat    180
ctgaaccaca gcgacgtgag tttcgttgaa tcgtcgtcgc agagcgtcag ccacgcgccg    240
ccgaagctgg aggattttct cggcgactcc tccgctgtta tgcgttactc cgacagccag    300
acggagacgc aggactcgtc gctgacgcac atctacgacc accaccacca ccaccaccac    360
caccaccacc acggttcttc tgcgtacttc ggcggtgacc accaggatct caaggccatt    420
actggattcc aagcttttc gactaactct ggctccgagg ttgatgattc tgcatcgatc    480
ggaaaggcgc agggcagcga gttcgggact cactctattg agtcctccgt caacgagttc    540
gccgcgttct ccggtggcac caacaccggt ggaaccttgt cgctcgccgt cgcgcagagc    600
```

```
tccgagaagg ccgtcgctgc tgcggcggag tccgatcgct cgaagaaggt tgtggatacc      660
ttcggccagc ggacttctat atacagaggt gtcactaggc accgatggac aggaagatat      720
gaagcgcatc tatgggacaa tagttgcaga agggagggtc aagccagaaa agggcgtcaa      780
gtttatttgg gtggatatga taaggaagaa aaggccgcga gagcttatga tttggcagct      840
ctaaagtact ggggtcccac tgctaccacc aacttccctg tttccaatta ttcgaaggaa      900
gtggaggaga tgaaacatgt aacaaagcaa gaatttattg catcattgcg gaggaaaagt      960
agtggtttct ccaggggagc ttccatatac agaggtgtta caaggcatca tcaacagggt     1020
aggtggcaag caagaattgg ccgtgtagct ggaaacaaag atttatactt gggaacattc     1080
gcaaccgagg aggaagcagc agaggcatat gatattgcag ccataaagtt cagaggtgca     1140
aacgcggtaa ccaactttga gatgaataga tatgatgtgg aagctataat gaagagttct     1200
cttccagtgg gtggggcagc aaaacgcttg aggctttccc ttgaatcaga gcagaaagct     1260
cctcctgtga acagcagcag tcagcagcag aatccacagt gtggtaacgt gagtggtagc     1320
atcaatttct cagccattca tcagccaatt gcttcaatcc cttgtggaat tccgtttgat     1380
tcaacaacag catattatcc tcacaacctt ttccaacatt ttcaccctac caacgctggt     1440
gcagcagcgt ctgctgttac ttctgccaat gcaaccgcac taactgcact gccagcatca     1500
gcagcaactg agttctttat ttggcctcat cagtcttatt ga                        1542
```

<210> SEQ ID NO 30
<211> LENGTH: 513
<212> TYPE: PRT
<213> ORGANISM: Glycine max

<400> SEQUENCE: 30

```
Met Ala Arg Ala Ser Thr Asn Trp Leu Ser Phe Ser Leu Ser Pro Met
 1               5                   10                  15

Glu Met Leu Arg Thr Pro Glu Pro Gln Phe Val Gln Tyr Asp Ala Ala
            20                  25                  30

Ser Asp Thr Ser Ser His His Tyr Tyr Leu Asp Asn Leu Tyr Thr Asn
        35                  40                  45

Gly Trp Gly Asn Gly Ser Leu Lys Phe Glu Gln Asn Leu Asn His Ser
    50                  55                  60

Asp Val Ser Phe Val Glu Ser Ser Gln Ser Val Ser His Ala Pro
 65                  70                  75                  80

Pro Lys Leu Glu Asp Phe Leu Gly Asp Ser Ser Ala Val Met Arg Tyr
                85                  90                  95

Ser Asp Ser Gln Thr Glu Thr Gln Asp Ser Ser Leu Thr His Ile Tyr
            100                 105                 110

Asp His His His His His His His His Gly Ser Ser Ala
        115                 120                 125

Tyr Phe Gly Gly Asp His Gln Asp Leu Lys Ala Ile Thr Gly Phe Gln
    130                 135                 140

Ala Phe Ser Thr Asn Ser Gly Ser Glu Val Asp Asp Ser Ala Ser Ile
145                 150                 155                 160

Gly Lys Ala Gln Gly Ser Glu Phe Gly Thr His Ser Ile Glu Ser Ser
                165                 170                 175

Val Asn Glu Phe Ala Ala Phe Ser Gly Gly Thr Asn Thr Gly Gly Thr
            180                 185                 190

Leu Ser Leu Ala Val Ala Gln Ser Ser Glu Lys Ala Val Ala Ala Ala
        195                 200                 205
```

Ala Glu Ser Asp Arg Ser Lys Lys Val Val Asp Thr Phe Gly Gln Arg
210                 215                 220

Thr Ser Ile Tyr Arg Gly Val Thr Arg His Arg Trp Thr Gly Arg Tyr
225                 230                 235                 240

Glu Ala His Leu Trp Asp Asn Ser Cys Arg Arg Glu Gly Gln Ala Arg
            245                 250                 255

Lys Gly Arg Gln Val Tyr Leu Gly Gly Tyr Asp Lys Glu Glu Lys Ala
        260                 265                 270

Ala Arg Ala Tyr Asp Leu Ala Ala Leu Lys Tyr Trp Gly Pro Thr Ala
    275                 280                 285

Thr Thr Asn Phe Pro Val Ser Asn Tyr Ser Lys Glu Val Glu Glu Met
290                 295                 300

Lys His Val Thr Lys Gln Glu Phe Ile Ala Ser Leu Arg Arg Lys Ser
305                 310                 315                 320

Ser Gly Phe Ser Arg Gly Ala Ser Ile Tyr Arg Gly Val Thr Arg His
            325                 330                 335

His Gln Gln Gly Arg Trp Gln Ala Arg Ile Gly Arg Val Ala Gly Asn
        340                 345                 350

Lys Asp Leu Tyr Leu Gly Thr Phe Ala Thr Glu Glu Ala Ala Glu
    355                 360                 365

Ala Tyr Asp Ile Ala Ala Ile Lys Phe Arg Gly Ala Asn Ala Val Thr
370                 375                 380

Asn Phe Glu Met Asn Arg Tyr Asp Val Glu Ala Ile Met Lys Ser Ser
385                 390                 395                 400

Leu Pro Val Gly Gly Ala Ala Lys Arg Leu Arg Leu Ser Leu Glu Ser
            405                 410                 415

Glu Gln Lys Ala Pro Pro Val Asn Ser Ser Gln Gln Asn Pro
        420                 425                 430

Gln Cys Gly Asn Val Ser Gly Ser Ile Asn Phe Ser Ala Ile His Gln
            435                 440                 445

Pro Ile Ala Ser Ile Pro Cys Gly Ile Pro Phe Asp Ser Thr Thr Ala
    450                 455                 460

Tyr Tyr Pro His Asn Leu Phe Gln His Phe His Pro Thr Asn Ala Gly
465                 470                 475                 480

Ala Ala Ala Ser Ala Val Thr Ser Ala Asn Ala Thr Ala Leu Thr Ala
            485                 490                 495

Leu Pro Ala Ser Ala Ala Thr Glu Phe Phe Ile Trp Pro His Gln Ser
        500                 505                 510
Tyr

<210> SEQ ID NO 31
<211> LENGTH: 2388
<212> TYPE: DNA
<213> ORGANISM: Glycine max

<400> SEQUENCE: 31

```
ccttgctgta gctaaacaac aaaaaccaag tcttcattgg taacaagaag attattattt    60
ttatatgatt tgtttattta tcacccaatg attgactttg cctagctgca gctgctacga   120
gagaagatac tgctggtggt ggtgctagca atagcaagtt taaagttcaa acctttttca   180
agtaatttat aagttgagaa agaaaagaaa aaaccaagaa aaaagaagc aaagatgaag   240
tccatgaatg atagtaacac cgttgatgat gggaacaatc ataataactg gttgggattc   300
tctctctcac cccacatgaa aatggatgtt gttacttctt ctactaccac tggtcctcat   360
catccccacc aacaccatca tcatcatcac tactatcatc accctcacga ggcttctgct   420
```

| | |
|---|---|
| gcagcttgca acaacaacaa caacactgtt cccactaact tctatatgtc accctcgcac | 480 |
| ctcaacacct ctggaatatg ttatggtgtt ggagaaaaca gtgcctttca cactcctttg | 540 |
| gccatgatgc ctctcaagtc agatgggtca ctttgcatta tggaggctct aacaagatca | 600 |
| caaacccaaa tgatggtgcc aacttcatct ccaaaacttg aggacttcct aggtggtgca | 660 |
| actatggggg ctcaagacta tggaacccat gagagagaag caatggctct aagcctagac | 720 |
| agtatctact acagcaacca gaatgctgaa cctgaaacca cagggacca ttcatcttct | 780 |
| cttgaccttc tttctgacca tttcaggcac caaacccatc atcacccata ttactcagga | 840 |
| cttgggattt accaagtgga ggaagaagaa accaaggaac aaccacacgt tgcagtttgc | 900 |
| agctcccaaa tgcctcaagt ggttgaaggc agcattgctt gcttcaaaaa ctgggtgcca | 960 |
| acaagggaat actcttcttc ttccactcag cagaatctgg agcagcatca agtgaatagt | 1020 |
| agtagcagtg gtggccttgg agaggataat aatgtagctt atgggaatgt tggtgttggt | 1080 |
| agtagtgttg gttgtggtga gttacagtct ttgagtttgt ctatgagtcc tggttctcaa | 1140 |
| tcaagctgtg tcactgttcc aactcagatc tcatcttctg gaactgactc agttgctgtg | 1200 |
| gatgccaaaa agagaggctc ttctaagctt ggacagaagc aacctgtgca taggaaatcc | 1260 |
| atcgacacat ttggtcaaag aacttctcag tatagaggtg tcacaaggca tagatggact | 1320 |
| ggtagatatg aagcacattt gtgggataac agttgcaaga aggaagggca aacaaggaaa | 1380 |
| ggacgacaag tgtatttggg tggttatgat atggaagaga aagctgcaag ggcttatgat | 1440 |
| cttgcggctc tcaagtattg gggaccttca acacacataa acttcccgct agaaaattac | 1500 |
| caaactcaac ttgaagaaat gaagaatatg agtaggcagg aatacgtggc ccacttgaga | 1560 |
| agaaagagta gtgggttttc aaggggtgcc tcaatgtaca gaggagtgac aaggcaccac | 1620 |
| caacatggca ggtggcaagc aaggataggc agagttgcag gaaataagga cctttatctt | 1680 |
| gggacattca gcactcaaga ggaagcagct gaagcatatg atgtagctgc aatcaaattt | 1740 |
| cgtggggtga atgctgtcac caactttgac atatcaagat acgacgttga gagaataatg | 1800 |
| gccagcaaca cccttctagc tggagagcta gctagaagaa acaagaacag tgagccaaga | 1860 |
| accgaggcca tagagtacaa tgttgtgtca agccaacaag tcataagcaa cagggaagaa | 1920 |
| gttcacgaga ctgtgaacaa caacaacaat aataatagtg aaaatggttc atcatcagat | 1980 |
| tggaagatga gtttgtatca tcatcagcaa cagtcaaaca actgtgacca gaaaaccatc | 2040 |
| aagtgtgaaa attataatag aggtggtgct gctttctctg tgtccctaca agatctcatt | 2100 |
| gggattgact cagtaggatc tagccaaggc atgatggatg agtctactaa gatagggact | 2160 |
| cattttccaa acccttcctc gctggtcacc agtttaagca gctcaaggga aggtagccct | 2220 |
| gataaaatgg gccccacttt gctcattcca aagcctccaa tggggtcaaa gattgttact | 2280 |
| agccctactg ttgccaatgg tgtcactgtt ggctcttggt ttccctctca aatgaggcca | 2340 |
| gtctcaatgt ctcacttgcc agtttttgct gcttggagtg atgcctag | 2388 |

<210> SEQ ID NO 32
<211> LENGTH: 2154
<212> TYPE: DNA
<213> ORGANISM: Glycine max

<400> SEQUENCE: 32

| | |
|---|---|
| atgaagtcca tgaatgatag taacaccgtt gatgatggga acaatcataa taactggttg | 60 |
| ggattctctc tctcacccca catgaaaatg gatgttgtta cttcttctac taccactggt | 120 |
| cctcatcatc cccaccaaca ccatcatcat catcactact atcatcaccc tcacgaggct | 180 |

```
tctgctgcag cttgcaacaa caacaacaac actgttccca ctaacttcta tatgtcaccc      240
tcgcacctca acacctctgg aatatgttat ggtgttggag aaaacagtgc ctttcacact      300
cctttggcca tgatgcctct caagtcagat gggtcacttt gcattatgga ggctctaaca      360
agatcacaaa cccaaatgat ggtgccaact tcatctccaa aacttgagga cttcctaggt      420
ggtgcaacta tggggctca agactatgga acccatgaga gagaagcaat ggctctaagc      480
ctagacagta tctactacag caaccagaat gctgaacctg aaaccaacag ggaccattca      540
tcttctcttg accttctttc tgaccatttc aggcaccaaa cccatcatca cccatattac      600
tcaggacttg ggatttacca agtggaggaa gaagaaacca aggaacaacc acacgttgca      660
gtttgcagct cccaaatgcc tcaagtggtt gaaggcagca ttgcttgctt caaaaactgg      720
gtgccaacaa gggaatactc ttcttcttcc actcagcaga atctggagca gcatcaagtg      780
aatagtagta gcagtggtgg ccttggagag gataataatg tagcttatgg gaatgttggt      840
gttggtagta gtgttggttg tggtgagtta cagtctttga gtttgtctat gagtcctggt      900
tctcaatcaa gctgtgtcac tgttccaact cagatctcat cttctggaac tgactcagtt      960
gctgtggatg ccaaaagag aggctcttct aagcttggac agaagcaacc tgtgcatagg     1020
aaatccatcg acacatttgg tcaaagaact ctcagtata gaggtgtcac aaggcataga     1080
tggactggta gatatgaagc acatttgtgg gataacagtt gcaagaagga agggcaaaca     1140
aggaaaggac gacaagtgta tttgggtggt tatgatatgg aagagaaagc tgcaagggct     1200
tatgatcttg cggctctcaa gtattgggga ccttcaacac acataaactt cccgctagaa     1260
aattaccaaa ctcaacttga agaaatgaag aatatgagta ggcaggaata cgtggcccac     1320
ttgagaagaa agagtagtgg gttttcaagg ggtgcctcaa tgtacagagg agtgacaagg     1380
caccaccaac atggcaggtg gcaagcaagg ataggcagag ttgcaggaaa taaggacctt     1440
tatcttggga cattcagcac tcaagaggaa gcagctgaag catatgatgt agctgcaatc     1500
aaatttcgtg gggtgaatgc tgtcaccaac tttgacatat caagatacga cgttgagaga     1560
ataatggcca gcaacaccct tctagctgga gagctagcta aagaaaacaa gaacagtgag     1620
ccaagaaccg aggccataga gtacaatgtt gtgtcaagcc aacaagtcat aagcaacagg     1680
gaagaagttc acgagactgt gaacaacaac aacaataata atagtgaaaa tggttcatca     1740
tcagattgga agatgagttt gtatcatcat cagcaacagt caaacaactg tgaccagaaa     1800
accatcaagt gtgaaaatta taatagaggt ggtgctgctt tctctgtgtc cctacaagat     1860
ctcattggga ttgactcagt aggatctagc caaggcatga tggatgagtc tactaagata     1920
gggactcatt tttcaaaccc ttcctcgctg gtcaccagtt taagcagctc aagggaaggt     1980
agccctgata aaatgggccc cactttgctc attccaaagc tccaatggg gtcaaagatt     2040 gttactagcc ctactgttgc caatggtgtc actgttggct cttggtttcc ctctcaaatg     2100
aggccagtct caatgtctca cttgccagtt tttgctgctt ggagtgatgc ctag           2154
```

<210> SEQ ID NO 33
<211> LENGTH: 717
<212> TYPE: PRT
<213> ORGANISM: Glycine max

<400> SEQUENCE: 33

```
Met Lys Ser Met Asn Asp Ser Asn Thr Val Asp Asp Gly Asn Asn His
 1               5                  10                  15

Asn Asn Trp Leu Gly Phe Ser Leu Ser Pro His Met Lys Met Asp Val
            20                  25                  30
```

Val Thr Ser Ser Thr Thr Thr Gly Pro His His Pro His Gln His His
            35                  40                  45

His His His His Tyr Tyr His His Pro His Glu Ala Ser Ala Ala Ala
     50                  55                  60

Cys Asn Asn Asn Asn Thr Val Pro Thr Asn Phe Tyr Met Ser Pro
 65                  70                  75                  80

Ser His Leu Asn Thr Ser Gly Ile Cys Tyr Gly Val Gly Glu Asn Ser
                 85                  90                  95

Ala Phe His Thr Pro Leu Ala Met Met Pro Leu Lys Ser Asp Gly Ser
            100                 105                 110

Leu Cys Ile Met Glu Ala Leu Thr Arg Ser Gln Thr Gln Met Met Val
            115                 120                 125

Pro Thr Ser Ser Pro Lys Leu Glu Asp Phe Leu Gly Gly Ala Thr Met
            130                 135                 140

Gly Ala Gln Asp Tyr Gly Thr His Glu Arg Glu Ala Met Ala Leu Ser
145                 150                 155                 160

Leu Asp Ser Ile Tyr Tyr Ser Asn Gln Asn Ala Glu Pro Glu Thr Asn
                165                 170                 175

Arg Asp His Ser Ser Leu Asp Leu Ser Asp His Phe Arg His
            180                 185                 190

Gln Thr His His His Pro Tyr Tyr Ser Gly Leu Gly Ile Tyr Gln Val
            195                 200                 205

Glu Glu Glu Glu Thr Lys Glu Gln Pro His Val Ala Val Cys Ser Ser
    210                 215                 220

Gln Met Pro Gln Val Val Glu Gly Ser Ile Ala Cys Phe Lys Asn Trp
225                 230                 235                 240

Val Pro Thr Arg Glu Tyr Ser Ser Ser Thr Gln Gln Asn Leu Glu
                245                 250                 255

Gln His Gln Val Asn Ser Ser Ser Gly Gly Leu Gly Glu Asp Asn
            260                 265                 270

Asn Val Ala Tyr Gly Asn Val Gly Val Gly Ser Ser Val Gly Cys Gly
                275                 280                 285

Glu Leu Gln Ser Leu Ser Leu Ser Met Ser Pro Gly Ser Gln Ser Ser
    290                 295                 300

Cys Val Thr Val Pro Thr Gln Ile Ser Ser Ser Gly Thr Asp Ser Val
305                 310                 315                 320

Ala Val Asp Ala Lys Lys Arg Gly Ser Ser Lys Leu Gly Gln Lys Gln
                325                 330                 335

Pro Val His Arg Lys Ser Ile Asp Thr Phe Gly Gln Arg Thr Ser Gln
            340                 345                 350

Tyr Arg Gly Val Thr Arg His Arg Trp Thr Gly Arg Tyr Glu Ala His
            355                 360                 365

Leu Trp Asp Asn Ser Cys Lys Lys Glu Gly Gln Thr Arg Lys Gly Arg
370                 375                 380

Gln Val Tyr Leu Gly Gly Tyr Asp Met Glu Glu Lys Ala Ala Arg Ala
385                 390                 395                 400

Tyr Asp Leu Ala Ala Leu Lys Tyr Trp Gly Pro Ser Thr His Ile Asn
                405                 410                 415

Phe Pro Leu Glu Asn Tyr Gln Thr Gln Leu Glu Glu Met Lys Asn Met
            420                 425                 430

Ser Arg Gln Glu Tyr Val Ala His Leu Arg Arg Lys Ser Ser Gly Phe
            435                 440                 445

Ser Arg Gly Ala Ser Met Tyr Arg Gly Val Thr Arg His His Gln His

```
                450            455            460
Gly Arg Trp Gln Ala Arg Ile Gly Arg Val Ala Gly Asn Lys Asp Leu
465                 470                 475                 480

Tyr Leu Gly Thr Phe Ser Thr Gln Glu Glu Ala Ala Glu Ala Tyr Asp
                485                 490                 495

Val Ala Ala Ile Lys Phe Arg Gly Val Asn Ala Val Thr Asn Phe Asp
                500                 505                 510

Ile Ser Arg Tyr Asp Val Glu Arg Ile Met Ala Ser Asn Thr Leu Leu
                515                 520                 525

Ala Gly Glu Leu Ala Arg Arg Asn Lys Asn Ser Glu Pro Arg Thr Glu
530                 535                 540

Ala Ile Glu Tyr Asn Val Val Ser Ser Gln Gln Val Ile Ser Asn Arg
545                 550                 555                 560

Glu Glu Val His Glu Thr Val Asn Asn Asn Asn Asn Asn Asn Ser Glu
                565                 570                 575

Asn Gly Ser Ser Ser Asp Trp Lys Met Ser Leu Tyr His His Gln Gln
                580                 585                 590

Gln Ser Asn Asn Cys Asp Gln Lys Thr Ile Lys Cys Glu Asn Tyr Asn
                595                 600                 605

Arg Gly Gly Ala Ala Phe Ser Val Ser Leu Gln Asp Leu Ile Gly Ile
610                 615                 620

Asp Ser Val Gly Ser Gln Gly Met Met Asp Glu Ser Thr Lys Ile
625                 630                 635                 640

Gly Thr His Phe Ser Asn Pro Ser Ser Leu Val Thr Ser Leu Ser Ser
                645                 650                 655

Ser Arg Glu Gly Ser Pro Asp Lys Met Gly Pro Thr Leu Leu Ile Pro
                660                 665                 670

Lys Pro Pro Met Gly Ser Lys Ile Val Thr Ser Pro Thr Val Ala Asn
                675                 680                 685

Gly Val Thr Val Gly Ser Trp Phe Pro Ser Gln Met Arg Pro Val Ser
                690                 695                 700

Met Ser His Leu Pro Val Phe Ala Ala Trp Ser Asp Ala
705                 710                 715

<210> SEQ ID NO 34
<211> LENGTH: 2259
<212> TYPE: DNA
<213> ORGANISM: Glycine max

<400> SEQUENCE: 34
atgaagagta tggaaaatga tgacaatgct gaccttaata atcaaaacaa ttggttgggt    60
ttctcactct ctcctcaaat gcataatata ggagtttctt cacactcaca accttcctct   120
gctgctgaag tggttcctac aagctttttac caccacactg ctccacttag tagctatggt   180
ttctactatg gacttgaagc tgaaaatgtt ggattgtatt cagctttgcc aatcatgccc   240
ctcaaatctg atggctctct ctatggattg gaaactttaa gcaggtcaca agcacaagca   300
atggctacta cttcaacacc aaaactggag aacttcttag gtggggaagc catggggacc   360
cctcatcact acgaatgtag tgccacagaa acaatgcctc tgagcttaga cagtgttttt   420
tacatccaac cctcacgccg tgacccaaat aataaccaaa cctaccaaaa ccatgttcaa   480
cacattagca ccaaccaaca caacaacag caagagcttc aagcatatta ctctaccttg   540
agaaaccatg atatgatatt agaagggtca agcaaagcc aaacttctga acaacaacat   600
cttcatgttc aaaacatggg tggtgatgat gccgttcctg ttcctggcct caagagttgg   660
```

```
gaagtgagga acttccaagc tagccatgca catgagtcaa agatgattgt tcctcatgtg    720
gaggaaaatg ctggtgaatc agggtccatt ggatcaatgg cttatggtga cttgcaatcg    780
ttgagcttgt ccatgagtcc tagctctcag tctagcagtg tcacaagttc tcaccgtgct    840
tcacctgctg tcgttgattc tgttgccatg gatactaaga aaaggggggcc tgaaaaggtt    900
gaccagaagc aaattgttca taggaagtcc attgacacct ttggacaaag aacctcccag    960
tatagaggag taacaaggca taggtggact gggagatatg aagctcatct ttgggacaac   1020
agctgcaaga agaggggca agcaggaaa ggaagacaag tttatctagg gggttatgat    1080
atggaagaaa aagctgcgag agcttatgat ctagcggcac tcaagtattg ggaccctcc    1140
actcacataa actttccttt ggaaaattat caaaatgaac ttgaggaaat aagaacatg    1200
actagacaag agtatgttgc tcatttgaga agaaaaagca gcggattctc aagaggggct   1260
tccatgtaca gaggagtaac aagacaccac caacatggaa ggtggcaagc tcgaattggt   1320
agagtggctg gaaacaaaga tctatatctt ggaacctta gtacacaaga ggaagcagct   1380
gaagcctatg atattgctgc tataaaattc cgaggagcga atgctgtaac caactttgac   1440
atcacaagat atgatgtgga gaaaatcatg gcaagcagca acctccttag cagtgagcta   1500
gctaggcgca accgagagac ggacaatgaa actcagtgca ttgatcaaaa tcacaataag   1560
ccttctgcat atgaggacac tcaagaagct attctaatgc accagaagag ctgtgagagc   1620
gaaaatgatc agtggaagat ggttctctac caatcctctc agcaacttga gcagaatcca   1680
ccaacaattg agagtgacag aactaaccag tccttcgcag tggctttgga caacatgttt   1740
catcaggaag tagaggaatc aagtaaggcg aggacgcatg tgtcaaatcc ttcttcattg   1800
gccacaagtt tgagcagctc aagagaaggt agccctgata ggacaagctt gccaatgctc   1860
tctggaatgc cttcaactgc atcaaaacta ttggctacta atccaaataa cgtgaattct   1920
tgggaccctt cacccatttt gaggccagca cttactttgc tcaaatgcc agttttgca    1980
gcttggacag atgcatagtt catagctcaa tagtcctttt aattttttgt tctctcaagt   2040
gaaatttcaa tccttttta ttgtcttttt ttgcatgcat gaacaacaca agaggaaggg   2100
gttgtagcta gtcaaatgga gggtctaaat attatatcat cacatcactg tcagcaagtt   2160
taatttaaac tttcaaatca tccgacacgc agcggccgct ctagaggatc caagcttacg   2220
tacgcgtgca tgcgacgtca tagctcttct ataggcacc                          2259

<210> SEQ ID NO 35
<211> LENGTH: 1998
<212> TYPE: DNA
<213> ORGANISM: Glycine max

<400> SEQUENCE: 35
atgaagagta tggaaaatga tgacaatgct gaccttaata atcaaaacaa ttggttgggt     60
ttctcactct ctcctcaaat gcataatata ggagtttctt cacactcaca accttcctct    120
gctgctgaag tggttcctac aagcttttac caccacactg ctccacttag tagctatggt    180
ttctactatg gacttgaagc tgaaaatgtt ggattgtatt cagctttgcc aatcatgccc    240
ctcaaatctg atggctctct ctatggattg gaaactttaa gcaggtcaca agcacaagca    300
atggctacta cttcaacacc aaaactggag aacttcttag gtggggaagc catggggacc    360
cctcatcact acgaatgtag tgccacagaa acaatgcctc tgagcttaga cagtgttttt    420
tacatccaac cctcacgccg tgacccaaat aataaccaaa cctaccaaaa ccatgttcaa    480
cacattagca ccaaccaaca acaacaacag caagagcttc aagcatatta ctctaccttg    540
```

```
agaaaccatg atatgatatt agaagggtca aagcaaagcc aaacttctga caacaacaat      600
cttcatgttc aaaacatggg tggtgatgat gccgttcctg ttcctggcct caagagttgg      660
gaagtgagga acttccaagc tagccatgca catgagtcaa agatgattgt tcctcatgtg      720
gaggaaaatg ctggtgaatc agggtccatt ggatcaatgg cttatggtga cttgcaatcg      780
ttgagcttgt ccatgagtcc tagctctcag tctagcagtg tcacaagttc tcaccgtgct      840
tcacctgctg tcgttgattc tgttgccatg gatactaaga aaggggggcc tgaaaaggtt      900
gaccagaagc aaattgttca taggaagtcc attgacacct ttggacaaag aacctcccag      960
tatagaggag taacaaggca taggtggact gggagatatg aagctcatct ttgggacaac     1020
agctgcaaga agaggggca aagcaggaaa ggaagacaag tttatctagg gggttatgat     1080
atggaagaaa aagctgcgag agcttatgat ctagcggcac tcaagtattg ggaccctcc      1140
actcacataa actttccttt ggaaaattat caaaatgaac ttgaggaaat aagaacatg      1200
actagacaag agtatgttgc tcatttgaga agaaaaagca gcggattctc aagaggggct     1260
tccatgtaca gaggagtaac aagacaccac caacatggaa ggtggcaagc tcgaattggt     1320
agagtggctg gaaacaaaga tctatatctt ggaaccttta gtacacaaga ggaagcagct     1380
gaagcctatg atattgctgc tataaaattc cgaggagcga atgctgtaac caactttgac     1440
atcacaagat atgatgtgga gaaaatcatg gcaagcagca acctccttag cagtgagcta     1500
gctaggcgca accgagagac ggacaatgaa actcagtgca ttgatcaaaa tcacaataag     1560
ccttctgcat atgaggacac tcaagaagct attctaatgc accagaagag ctgtgagagc     1620
gaaaatgatc agtggaagat ggttctctac caatcctctc agcaacttga gcagaatcca     1680
ccaacaattg agagtgacag aactaaccag tccttcgcag tggctttgga caacatgttt     1740
catcaggaag tagaggaatc aagtaaggcg aggacgcatg tgtcaaatcc ttcttcattg     1800
gccacaagtt tgagcagctc aagagaaggt agccctgata ggacaagctt gccaatgctc     1860
tctggaatgc cttcaactgc atcaaaacta ttggctacta atccaaataa cgtgaattct     1920
tgggaccctt caccccattt gaggccagca cttactttgc ctcaaatgcc agttttttgca     1980
gcttggacag atgcatag                                                   1998
```

<210> SEQ ID NO 36
<211> LENGTH: 665
<212> TYPE: PRT
<213> ORGANISM: Glycine max

<400> SEQUENCE: 36

```
Met Lys Ser Met Glu Asn Asp Asp Asn Ala Asp Leu Asn Asn Gln Asn
  1               5                  10                  15

Asn Trp Leu Gly Phe Ser Leu Ser Pro Gln Met His Asn Ile Gly Val
             20                  25                  30

Ser Ser His Ser Gln Pro Ser Ser Ala Ala Glu Val Val Pro Thr Ser
         35                  40                  45

Phe Tyr His His Thr Ala Pro Leu Ser Ser Tyr Gly Phe Tyr Tyr Gly
     50                  55                  60

Leu Glu Ala Glu Asn Val Gly Leu Tyr Ser Ala Leu Pro Ile Met Pro
 65                  70                  75                  80

Leu Lys Ser Asp Gly Ser Leu Tyr Gly Leu Thr Leu Ser Arg Ser
                 85                  90                  95

Gln Ala Gln Ala Met Ala Thr Thr Ser Thr Pro Lys Leu Glu Asn Phe
            100                 105                 110

Leu Gly Gly Glu Ala Met Gly Thr Pro His His Tyr Glu Cys Ser Ala
```

```
                115                 120                 125
Thr Glu Thr Met Pro Leu Ser Leu Asp Ser Val Phe Tyr Ile Gln Pro
130                 135                 140

Ser Arg Arg Asp Pro Asn Asn Asn Gln Thr Tyr Gln Asn His Val Gln
145                 150                 155                 160

His Ile Ser Thr Asn Gln Gln Gln Gln Gln Glu Leu Gln Ala Tyr
            165                 170                 175

Tyr Ser Thr Leu Arg Asn His Asp Met Ile Leu Glu Gly Ser Lys Gln
            180                 185                 190

Ser Gln Thr Ser Asp Asn Asn Leu His Val Gln Asn Met Gly Gly
        195                 200                 205

Asp Asp Ala Val Pro Val Pro Gly Leu Lys Ser Trp Glu Val Arg Asn
210                 215                 220

Phe Gln Ala Ser His Ala His Glu Ser Lys Met Ile Val Pro His Val
225                 230                 235                 240

Glu Glu Asn Ala Gly Glu Ser Gly Ser Ile Gly Ser Met Ala Tyr Gly
                245                 250                 255

Asp Leu Gln Ser Leu Ser Leu Ser Met Ser Pro Ser Ser Gln Ser Ser
            260                 265                 270

Ser Val Thr Ser Ser His Arg Ala Ser Pro Ala Val Val Asp Ser Val
        275                 280                 285

Ala Met Asp Thr Lys Lys Arg Gly Pro Glu Lys Val Asp Gln Lys Gln
290                 295                 300

Ile Val His Arg Lys Ser Ile Asp Thr Phe Gly Gln Arg Thr Ser Gln
305                 310                 315                 320

Tyr Arg Gly Val Thr Arg His Arg Trp Thr Gly Arg Tyr Glu Ala His
                325                 330                 335

Leu Trp Asp Asn Ser Cys Lys Lys Glu Gly Gln Ser Arg Lys Gly Arg
            340                 345                 350

Gln Val Tyr Leu Gly Gly Tyr Asp Met Glu Glu Lys Ala Ala Arg Ala
        355                 360                 365

Tyr Asp Leu Ala Ala Leu Lys Tyr Trp Gly Pro Ser Thr His Ile Asn
370                 375                 380

Phe Pro Leu Glu Asn Tyr Gln Asn Glu Leu Glu Glu Met Lys Asn Met
385                 390                 395                 400

Thr Arg Gln Glu Tyr Val Ala His Leu Arg Arg Lys Ser Ser Gly Phe
                405                 410                 415

Ser Arg Gly Ala Ser Met Tyr Arg Gly Val Thr Arg His His Gln His
            420                 425                 430

Gly Arg Trp Gln Ala Arg Ile Gly Arg Val Ala Gly Asn Lys Asp Leu
        435                 440                 445

Tyr Leu Gly Thr Phe Ser Thr Gln Glu Glu Ala Ala Glu Ala Tyr Asp
450                 455                 460

Ile Ala Ala Ile Lys Phe Arg Gly Ala Asn Ala Val Thr Asn Phe Asp
465                 470                 475                 480

Ile Thr Arg Tyr Asp Val Glu Lys Ile Met Ala Ser Ser Asn Leu Leu
                485                 490                 495

Ser Ser Glu Leu Ala Arg Arg Asn Arg Glu Thr Asp Asn Glu Thr Gln
            500                 505                 510

Cys Ile Asp Gln Asn His Asn Lys Pro Ser Ala Tyr Glu Asp Thr Gln
        515                 520                 525

Glu Ala Ile Leu Met His Gln Lys Ser Cys Glu Ser Glu Asn Asp Gln
530                 535                 540
```

```
Trp Lys Met Val Leu Tyr Gln Ser Ser Gln Gln Leu Glu Gln Asn Pro
545                 550                 555                 560

Pro Thr Ile Glu Ser Asp Arg Thr Asn Gln Ser Phe Ala Val Ala Leu
                565                 570                 575

Asp Asn Met Phe His Gln Glu Val Glu Glu Ser Ser Lys Ala Arg Thr
            580                 585                 590

His Val Ser Asn Pro Ser Ser Leu Ala Thr Ser Leu Ser Ser Ser Arg
        595                 600                 605

Glu Gly Ser Pro Asp Arg Thr Ser Leu Pro Met Leu Ser Gly Met Pro
    610                 615                 620

Ser Thr Ala Ser Lys Leu Leu Ala Thr Asn Pro Asn Asn Val Asn Ser
625                 630                 635                 640

Trp Asp Pro Ser Pro His Leu Arg Pro Ala Leu Thr Leu Pro Gln Met
                645                 650                 655

Pro Val Phe Ala Ala Trp Thr Asp Ala
            660                 665

<210> SEQ ID NO 37
<211> LENGTH: 2125
<212> TYPE: DNA
<213> ORGANISM: Glycine max

<400> SEQUENCE: 37
atgaagcgca taaatgagag taacaacacc gatgatggaa acaatcataa ctggttgggg      60
ttctctctct caccccacat gaaaatggag gctacttcag cagccactgt tccgacaacc     120
ttctacatgt ccccttctca atctcacttg tccaacttcg gaatgtgtta cggtgtcgga     180
gaaaatggta acttccattc tccacttacg gttatgcctc tcaagtctga tgggtcactt     240
tgtatcttgg aagctctcaa agatcacaa acgcaagtga tggtgccaac ttcgtctccg      300
aaattggagg actttctagg tggtgcaact atgggaactc acgaatatgg aagccacgag     360
agaggtttga gcctagacag catctattat aactcccaaa acgcagaggc tcaacccaac     420
agagaccttc tttcacaacc cttcaggcaa caaggtcata tgagtgtcca acacacccct     480
tattactcag gccttgcttg ccatggttta tatcaagcac cgttggagga agaaacaaca     540
aaggaaacgc acgtgtcgga ttgcagctcc ctaatgcctc aaatgacaga aggcttgaaa     600
aactgggtgg ctccaacaag ggagttttca actcaccagc aggttttgga gcagcaaatg     660
aattgtggca tggggaatga gagaaatggt gtgtctttag gatctgtggg gtgtggagag     720
ttacagtctc taagcttatc tatgagtcct ggttctcagt ctagttgtgt cactgctcct     780
tctggaacag attctgttgc tgtggatgca agaagagag ggcatgctaa acttggtcag      840
aagcagcctg tgcatagaaa atctatcgac acatttgggc aaagaacctc gcagtataga     900
ggtgtcacaa ggcatagatg gactggtagg tatgaagcgc atttgtggga taatagttgc     960
aagaaggaag gcaaactag aaaggacga caagtgtatt tgggggggtta tgatatggag     1020 gagaaagctg caagagccta tgatctcgcg gcccttaagt actgggacc ttcaacgcat     1080 ataaactttt cgatagagaa ttaccaagtt caacttgagg aaatgaagaa catgagcaga     1140
caggaatacg ttgcacactt gagaagaaaa agcagcgggt tttctagagg tgcttcaata     1200
tacagagggg tcacaaggca tcaccaacat ggaagatggc aagcgaggat aggcagagtt     1260
gctgggaaca aagacctta ccttgggacg ttcagcaccc aagaggaagc agcagaagca      1320
tacgatgtag cggcgatcaa atttcgcggc gcaaatgcag tcacaaactt tgacatttca     1380
agatacgatg tggagagaat catggccagt agcaatctcc tcgctgggga gcttgcaagg     1440
```

```
cgtaagaaag ataacgatcc tagaaacaag gacatagact acaacaagag tgtagtaaca    1500
agtgtgaaca atgaggaaac ggttcaagtt caagcaggaa acaacaataa tgaaaacgac    1560
tcagagtgga agatggtttt atttaaccac ccttcacagc agcaacaggc aaatggcaat    1620
ggcagtgacc aaaaaataat gaactgtgga aattacagaa acagtgcatt ttctatggcc    1680
ctacaagatc ttattgggat tgattcggtg ggttctgggc agcataatat gctggacgag    1740
tctagcaaaa ttgggactca ttttcaaac acgtcatcgc tggtgacaag tttaagcagc    1800
tcaagagagg ctagtcctga aaaggggt ccctcgcttc tgttcccaat gcctccaatg    1860
gaaacaaaga ttgtgaaccc cattggtacc agtgttacct cttggctacc ctcaccaacg    1920
gttcaaatga ggccttctcc tgctatctct ttgtctcact tgccagtttt tgcttcttgg    1980
actgatactt aaatggagat aggcacggtc catttttcat gttatgttat gtaactaaaa    2040
tttacttttt tccttcatct tttatttcta atttgatttc ctaagtttaa aagctttaaa    2100
taaaaaaaaa aaaaaaaccg aacca                                          2125

<210> SEQ ID NO 38
<211> LENGTH: 1992
<212> TYPE: DNA
<213> ORGANISM: Glycine max

<400> SEQUENCE: 38
atgaagcgca taaatgagag taacaacacc gatgatggaa acaatcataa ctggttgggg     60
ttctctctct caccccacat gaaaatggag gctacttcag cagccactgt tccgacaacc    120
ttctacatgt cccttctca atctcacttg tccaacttcg gaatgtgtta cggtgtcgga    180
gaaaatggta acttccattc tccacttacg gttatgcctc tcaagtctga tgggtcactt    240
tgtatcttgg aagctctcaa aagatcacaa acgcaagtga tggtgccaac ttcgtctccg    300
aaattggagg actttctagg tggtgcaact atgggaactc acgaatatgg aagccacgag    360
agaggtttga gcctagacag catctattat aactcccaaa acgcagaggc tcaacccaac    420
agagaccttc tttcacaacc cttcaggcaa caaggtcata tgagtgtcca acacaccct    480 tattactcag gccttgcttg ccatggttta tatcaagcac cgttggagga agaaacaaca    540
aaggaaacgc acgtgtcgga ttgcagctcc ctaatgcctc aaatgacaga aggcttgaaa    600
aactgggtgg ctccaacaag ggagttttca actcaccagc aggttttgga gcagcaaatg    660
aattgtggca tgggaatga gagaaatggt gtgtctttag gatctgtggg gtgtggagag    720
ttacagtctc taagcttatc tatgagtcct ggttctcagt ctagttgtgt cactgctcct    780
tctggaacag attctgttgc tgtggatgca agaagagag gcatgctaa acttggtcag    840 aagcagcctg tgcatagaaa atctatcgac acatttgggc aaagaacctc gcagtataga    900
ggtgtcacaa ggcatagatg gactggtagg tatgaagcgc atttgtggga taatagttgc    960
aagaaggaag ggcaaactag gaaggacga caagtgtatt tgggggggtta tgatatggag   1020 gagaaagctg caagagccta tgatctcgcg gcccttaagt actggggacc ttcaacgcat   1080
ataaactttt cgatagagaa ttaccaagtt caacttgagg aaatgaagaa catgagcaga   1140
caggaatacg ttgcacactt gagaagaaaa agcagcgggt tttctagagg tgcttcaata   1200
tacagagggg tcacaaggca tcaccaacat ggaagatggc aagcgaggat aggcagagtt   1260
gctgggaaca aagacctta ccttgggacg ttcagcaccc aagaggaagc agcagaagca   1320
tacgatgtag cggcgatcaa atttcgcggc gcaaatgcag tcacaaactt tgacatttca   1380
agatacgatg tggagagaat catggccagt agcaatctcc tcgctgggga gcttgcaagg   1440
```

-continued

```
cgtaagaaag ataacgatcc tagaaacaag gacatagact acaacaagag tgtagtaaca      1500
agtgtgaaca atgaggaaac ggttcaagtt caagcaggaa acaacaataa tgaaaacgac      1560
tcagagtgga agatggtttt atttaaccac ccttcacagc agcaacaggc aaatggcaat      1620
ggcagtgacc aaaaaataat gaactgtgga aattacagaa acagtgcatt ttctatggcc      1680
ctacaagatc ttattgggat tgattcggtg ggttctgggc agcataatat gctggacgag      1740
tctagcaaaa ttgggactca tttttcaaac acgtcatcgc tggtgacaag tttaagcagc      1800
tcaagagagg ctagtcctga gaaaaggggt ccctcgcttc tgttcccaat gcctccaatg      1860
gaaacaaaga ttgtgaaccc cattggtacc agtgttacct cttggctacc ctcaccaacg      1920
gttcaaatga ggccttctcc tgctatctct ttgtctcact tgccagtttt tgcttcttgg      1980
actgatactt aa                                                           1992

<210> SEQ ID NO 39
<211> LENGTH: 663
<212> TYPE: PRT
<213> ORGANISM: Glycine max

<400> SEQUENCE: 39

Met Lys Arg Ile Asn Glu Ser Asn Asn Thr Asp Asp Gly Asn Asn His
 1               5                  10                  15

Asn Trp Leu Gly Phe Ser Leu Ser Pro His Met Lys Met Glu Ala Thr
            20                  25                  30

Ser Ala Ala Thr Val Pro Thr Thr Phe Tyr Met Ser Pro Ser Gln Ser
        35                  40                  45

His Leu Ser Asn Phe Gly Met Cys Tyr Gly Val Gly Glu Asn Gly Asn
    50                  55                  60

Phe His Ser Pro Leu Thr Val Met Pro Leu Lys Ser Asp Gly Ser Leu
65                  70                  75                  80

Cys Ile Leu Glu Ala Leu Lys Arg Ser Gln Thr Gln Val Met Val Pro
                85                  90                  95

Thr Ser Ser Pro Lys Leu Glu Asp Phe Leu Gly Gly Ala Thr Met Gly
            100                 105                 110

Thr His Glu Tyr Gly Ser His Glu Arg Gly Leu Ser Leu Asp Ser Ile
        115                 120                 125

Tyr Tyr Asn Ser Gln Asn Ala Glu Ala Gln Pro Asn Arg Asp Leu Leu
    130                 135                 140

Ser Gln Pro Phe Arg Gln Gln Gly His Met Ser Val Gln Thr His Pro
145                 150                 155                 160

Tyr Tyr Ser Gly Leu Ala Cys His Gly Leu Tyr Gln Ala Pro Leu Glu
                165                 170                 175

Glu Glu Thr Thr Lys Glu Thr His Val Ser Asp Cys Ser Ser Leu Met
            180                 185                 190

Pro Gln Met Thr Glu Gly Leu Lys Asn Trp Val Ala Pro Thr Arg Glu
        195                 200                 205

Phe Ser Thr His Gln Gln Val Leu Glu Gln Gln Met Asn Cys Gly Met
    210                 215                 220

Gly Asn Glu Arg Asn Gly Val Ser Leu Gly Ser Val Gly Cys Gly Glu
225                 230                 235                 240

Leu Gln Ser Leu Ser Leu Ser Met Ser Pro Gly Ser Gln Ser Ser Cys
                245                 250                 255

Val Thr Ala Pro Ser Gly Thr Asp Ser Val Ala Val Asp Ala Lys Lys
            260                 265                 270

Arg Gly His Ala Lys Leu Gly Gln Lys Gln Pro Val His Arg Lys Ser
```

```
                275                 280                 285
Ile Asp Thr Phe Gly Gln Arg Thr Ser Gln Tyr Arg Gly Val Thr Arg
290                 295                 300
His Arg Trp Thr Gly Arg Tyr Glu Ala His Leu Trp Asp Asn Ser Cys
305                 310                 315                 320
Lys Lys Glu Gly Gln Thr Arg Lys Gly Arg Gln Val Tyr Leu Gly Gly
                325                 330                 335
Tyr Asp Met Glu Lys Ala Ala Arg Ala Tyr Asp Leu Ala Ala Leu
    340                 345                 350
Lys Tyr Trp Gly Pro Ser Thr His Ile Asn Phe Ser Ile Glu Asn Tyr
    355                 360                 365
Gln Val Gln Leu Glu Glu Met Lys Asn Met Ser Arg Gln Glu Tyr Val
370                 375                 380
Ala His Leu Arg Arg Lys Ser Ser Gly Phe Ser Arg Gly Ala Ser Ile
385                 390                 395                 400
Tyr Arg Gly Val Thr Arg His His Gln His Gly Arg Trp Gln Ala Arg
                405                 410                 415
Ile Gly Arg Val Ala Gly Asn Lys Asp Leu Tyr Leu Gly Thr Phe Ser
                420                 425                 430
Thr Gln Glu Glu Ala Ala Glu Ala Tyr Asp Val Ala Ala Ile Lys Phe
            435                 440                 445
Arg Gly Ala Asn Ala Val Thr Asn Phe Asp Ile Ser Arg Tyr Asp Val
450                 455                 460
Glu Arg Ile Met Ala Ser Ser Asn Leu Leu Ala Gly Glu Leu Ala Arg
465                 470                 475                 480
Arg Lys Lys Asp Asn Asp Pro Arg Asn Lys Asp Ile Asp Tyr Asn Lys
                485                 490                 495
Ser Val Val Thr Ser Val Asn Asn Glu Glu Thr Val Gln Val Gln Ala
                500                 505                 510
Gly Asn Asn Asn Glu Asn Asp Ser Glu Trp Lys Met Val Leu Phe
        515                 520                 525
Asn His Pro Ser Gln Gln Gln Ala Asn Gly Asn Gly Ser Asp Gln
530                 535                 540
Lys Ile Met Asn Cys Gly Asn Tyr Arg Asn Ser Ala Phe Ser Met Ala
545                 550                 555                 560
Leu Gln Asp Leu Ile Gly Ile Asp Ser Val Gly Ser Gly Gln His Asn
                565                 570                 575
Met Leu Asp Glu Ser Ser Lys Ile Gly Thr His Phe Ser Asn Thr Ser
                580                 585                 590
Ser Leu Val Thr Ser Leu Ser Ser Arg Glu Ala Ser Pro Glu Lys
        595                 600                 605
Arg Gly Pro Ser Leu Leu Phe Pro Met Pro Met Glu Thr Lys Ile
    610                 615                 620
Val Asn Pro Ile Gly Thr Ser Val Thr Ser Trp Leu Pro Ser Pro Thr
625                 630                 635                 640
Val Gln Met Arg Pro Ser Pro Ala Ile Ser Leu Ser His Leu Pro Val
                645                 650                 655
Phe Ala Ser Trp Thr Asp Thr
                660

<210> SEQ ID NO 40
<211> LENGTH: 1458
<212> TYPE: DNA
<213> ORGANISM: Oryza sativa
```

```
<400> SEQUENCE: 40
ggcctctcct cctcctcctc acctgcacct gcaccaacgc gagagatcat ggcgaagaga    60
tcgtctcctg atcctgcatc atcttctcca tctgcatcat cctgccgtc gtctccttcc   120
tcctcttcct ccgaggattc ctcttcgccc atgtcgatgc cctgcaagag gagggcgagg   180
ccgaggacgg agaagagcac cggcaaggcc aagaggccca agaaggagag caaggaggtg   240
gctgatcctc cttccaatgg cggcggcggc ggcaagagga gttctatcta caggggagtc   300
accaggcatc ggtggactgg cagatttgag gcccatctgt gggacaagaa ttgctccact   360
tcacttcaga acaagaagaa agggaggcaa gtctatttgg gggcttatga tagtgaggaa   420
gcagctgctc gtgcatatga ccttgcagct cttaagtact ggggtcctga cagtgctc     480
aatttcccac tggaggaata tgagaaggag aggtcggaga tggagggcgt gtcgagggag   540
gagtacctgg cctccctccg ccgccggagc agcggtttct ccaggggtgt ctccaagtac   600
agaggcgttg ccaggcatca ccacaatggg cggtgggagg cacggatagg gcgggtcctg   660
gggaacaagt acctctacct gggtactttc gatactcaag aggaggcagc caaggcctat   720
gatcttgctg caattgaata ccgaggtgcc aatgcggtaa ccaacttcga catcagctgc   780
tacctggacc agccacagtt actggcacag ctgcaacagg aaccacagtt actgcacaa    840
ctgcaacaag agctacaggt ggtgccagca ttacatgaag agcctcaaga tgatgaccga   900
agtgagaatg cagtccaaga gctcagttcc agtgaagcaa atacatcaag tgacaacaat   960
gagccacttg cagccgatga cagcgctgaa tgcatgaatg aaccccttcc aattgttgat  1020
ggcattgaag aaagcctctg gagcccttgc ttggattatg aattggatac aatgcctggg  1080
gcttacttca gcaactcgat gaatttcagt gaatggttca atgatgaggc tttcgaaggc  1140
ggcatggagt acctatttga agggtgctcc agtataactg aaggcggcaa cagcatggat  1200
aactcaggtg tgacagaata caatttgttt gaggaatgca atatgttgga aaggacatt    1260
tcagattttt tagacaagga catttcagat tttttagata aggacatttc aatttcagat  1320
agggagcgaa tatctcctca agcaaacaat atctcctgcc ctcaaaaaat gatcagtgtg  1380
tgcaactgaa ttctctctgt gtgcgtgttt ctgggtgttg aaaatcttga gatatacagg  1440
gaagttttca ggttttta                                                1458

<210> SEQ ID NO 41
<211> LENGTH: 1341
<212> TYPE: DNA
<213> ORGANISM: Oryza sativa

<400> SEQUENCE: 41
atggcgaaga gatcgtctcc tgatcctgca tcatcttctc catctgcatc atcctcgccg    60
tcgtctcctt cctcctcttc ctccgaggat tcctcttcgc ccatgtcgat gccctgcaag   120
aggagggcga ggccgaggac ggagaagagc accggcaagg ccaagaggcc caagaaggag   180
agcaaggagg tggctgatcc ttcttccaat ggcggcggcg gcggcaagag gagttctatc   240
tacaggggag tcaccaggca tcggtggact ggcagatttg aggcccatct gtgggacaag   300
aattgctcca cttcacttca gaacaagaag aaagggaggc aagtctattt gggggcttat   360
gatagtgagg aagcagctgc tcgtgcatat gaccttgcag ctcttaagta ctggggtcct   420
gagacagtgc tcaatttccc actggaggaa tatgagaagg agaggtcgga gatggagggc   480
gtgtcgaggg aggagtacct ggcctccctc cgccgccgga gcagcggttt ctccagggg    540
gtctccaagt acagaggcgt tgccaggcat caccacaatg gcggtgggg ggcacggata    600
```

-continued

```
gggcgggtcc tggggaacaa gtacctctac ctgggtactt tcgatactca agaggaggca      660
gccaaggcct atgatcttgc tgcaattgaa taccgaggtg ccaatgcggt aaccaacttc      720
gacatcagct gctacctgga ccagccacag ttactggcac agctgcaaca ggaaccacag      780
ttactggcac aactgcaaca agagctacag gtggtgccag cattacatga agagcctcaa      840
gatgatgacc gaagtgagaa tgcagtccaa gagctcagtt ccagtgaagc aaatacatca      900
agtgacaaca atgagccact gcagccgat gacagcgctg aatgcatgaa tgaaccccctt      960
ccaattgttg atggcattga agaaagcctc tggagccctt gcttggatta tgaattggat     1020
acaatgcctg gggcttactt cagcaactcg atgaatttca gtgaatggtt caatgatgag     1080
gctttcgaag gcggcatgga gtacctattt gaagggtgct ccagtataac tgaaggcggc     1140
aacagcatgg ataactcagg tgtgacagaa tacaatttgt ttgaggaatg caatatgttg     1200
gagaaggaca tttcagattt tttagacaag gacatttcag atttttttaga taaggacatt     1260
tcaatttcag atagggagcg aatatctcct caagcaaaca atatctcctg ccctcaaaaa     1320
atgatcagtg tgtgcaactg a                                               1341
```

<210> SEQ ID NO 42
<211> LENGTH: 446
<212> TYPE: PRT
<213> ORGANISM: Oryza sativa

<400> SEQUENCE: 42

```
Met Ala Lys Arg Ser Ser Pro Asp Pro Ala Ser Ser Ser Pro Ser Ala
 1               5                  10                  15
Ser Ser Ser Pro Ser Ser Pro Ser Ser Ser Ser Glu Asp Ser Ser
             20                  25                  30
Ser Pro Met Ser Met Pro Cys Lys Arg Ala Arg Pro Arg Thr Glu
         35                  40                  45
Lys Ser Thr Gly Lys Ala Lys Arg Pro Lys Lys Glu Ser Lys Glu Val
 50                  55                  60
Ala Asp Pro Ser Ser Asn Gly Gly Gly Gly Lys Arg Ser Ser Ile
 65                  70                  75                  80
Tyr Arg Gly Val Thr Arg His Arg Trp Thr Gly Arg Phe Glu Ala His
                 85                  90                  95
Leu Trp Asp Lys Asn Cys Ser Thr Ser Leu Gln Asn Lys Lys Gly
            100                 105                 110
Arg Gln Val Tyr Leu Gly Ala Tyr Asp Ser Glu Glu Ala Ala Arg
        115                 120                 125
Ala Tyr Asp Leu Ala Ala Leu Lys Tyr Trp Gly Pro Glu Thr Val Leu
    130                 135                 140
Asn Phe Pro Leu Glu Glu Tyr Glu Lys Glu Arg Ser Glu Met Glu Gly
145                 150                 155                 160
Val Ser Arg Glu Glu Tyr Leu Ala Ser Leu Arg Arg Ser Ser Gly
                165                 170                 175
Phe Ser Arg Gly Val Ser Lys Tyr Arg Gly Val Ala Arg His His His
            180                 185                 190
Asn Gly Arg Trp Glu Ala Arg Ile Gly Arg Val Leu Gly Asn Lys Tyr
        195                 200                 205
Leu Tyr Leu Gly Thr Phe Asp Thr Gln Glu Glu Ala Ala Lys Ala Tyr
    210                 215                 220
Asp Leu Ala Ala Ile Glu Tyr Arg Gly Ala Asn Ala Val Thr Asn Phe
225                 230                 235                 240
Asp Ile Ser Cys Tyr Leu Asp Gln Pro Gln Leu Leu Ala Gln Leu Gln
```

|     |     |     |     | 245 |     |     |     |     | 250 |     |     |     |     | 255 |     |
| --- | --- | --- | --- | --- | --- | --- | --- | --- | --- | --- | --- | --- | --- | --- | --- |
| Gln | Glu | Pro | Gln | Leu | Leu | Ala | Gln | Leu | Gln | Gln | Glu | Leu | Gln | Val | Val |
|     |     |     | 260 |     |     |     |     | 265 |     |     |     |     | 270 |     |     |
| Pro | Ala | Leu | His | Glu | Glu | Pro | Gln | Asp | Asp | Asp | Arg | Ser | Glu | Asn | Ala |
|     |     |     | 275 |     |     |     |     | 280 |     |     |     |     | 285 |     |     |
| Val | Gln | Glu | Leu | Ser | Ser | Ser | Glu | Ala | Asn | Thr | Ser | Ser | Asp | Asn | Asn |
|     |     |     | 290 |     |     |     |     | 295 |     |     |     |     | 300 |     |     |
| Glu | Pro | Leu | Ala | Ala | Asp | Asp | Ser | Ala | Glu | Cys | Met | Asn | Glu | Pro | Leu |
| 305 |     |     |     |     | 310 |     |     |     |     | 315 |     |     |     |     | 320 |
| Pro | Ile | Val | Asp | Gly | Ile | Glu | Glu | Ser | Leu | Trp | Ser | Pro | Cys | Leu | Asp |
|     |     |     |     | 325 |     |     |     |     | 330 |     |     |     |     | 335 |     |
| Tyr | Glu | Leu | Asp | Thr | Met | Pro | Gly | Ala | Tyr | Phe | Ser | Asn | Ser | Met | Asn |
|     |     |     |     | 340 |     |     |     |     | 345 |     |     |     |     | 350 |     |
| Phe | Ser | Glu | Trp | Phe | Asn | Asp | Glu | Ala | Phe | Glu | Gly | Gly | Met | Glu | Tyr |
|     |     |     |     | 355 |     |     |     |     | 360 |     |     |     |     | 365 |     |
| Leu | Phe | Glu | Gly | Cys | Ser | Ser | Ile | Thr | Glu | Gly | Gly | Asn | Ser | Met | Asp |
|     |     |     | 370 |     |     |     |     | 375 |     |     |     |     | 380 |     |     |
| Asn | Ser | Gly | Val | Thr | Glu | Tyr | Asn | Leu | Phe | Glu | Glu | Cys | Asn | Met | Leu |
| 385 |     |     |     |     | 390 |     |     |     |     | 395 |     |     |     |     | 400 |
| Glu | Lys | Asp | Ile | Ser | Asp | Phe | Leu | Asp | Lys | Asp | Ile | Ser | Asp | Phe | Leu |
|     |     |     |     | 405 |     |     |     |     | 410 |     |     |     |     | 415 |     |
| Asp | Lys | Asp | Ile | Ser | Ile | Ser | Asp | Arg | Glu | Arg | Ile | Ser | Pro | Gln | Ala |
|     |     |     |     | 420 |     |     |     |     | 425 |     |     |     |     | 430 |     |
| Asn | Asn | Ile | Ser | Cys | Pro | Gln | Lys | Met | Ile | Ser | Val | Cys | Asn |     |     |
|     |     |     |     | 435 |     |     |     |     | 440 |     |     |     |     | 445 |     |

<210> SEQ ID NO 43
<211> LENGTH: 1845
<212> TYPE: DNA
<213> ORGANISM: Oryza sativa
<220> FEATURE:
<221> NAME/KEY: modified_base
<222> LOCATION: (1643)
<223> OTHER INFORMATION: a, c, g, t, unknown or other

<400> SEQUENCE: 43

```
cgagctcgga tccactagta acggccgcca gtgtgctgga attcgccctt aagcagtggt    60
aacaacgcag agtacgcggg gagaaaataa taataagaag aacagattgt ataatctggg   120
gtatttttct ccccaacttt cctctctcgg tttccccgag aaatttcttg ttgtttccg    180
catcactccc cactgagccg cctccttgct cgccgctcgc gttcgtcgtc gtctcgtcgt   240
ttccacaatc aatttgacgt cgcccctatt tatgtcctgc ctcggtagtt gattcctccc   300
catttctgtt gcctctcgcg gttgtggtaa tcgacgctgt aggattttt tcttcttctt    360
cttttgggtc ttcggaggag gcgtccggat cttcgtccc catcgatccc ttccggccac   420
ggacatttcg tgggtagagc gattgattgg tggcttaggg ttaatattgg gcaggaaatg   480
gagagctctt tgaaagagga gaaggctgcg ggcgaatcag gggatgatga aaggcggag   540
aggagctccc ctatcaatct gaattcgttg ccagcaactg cggcgtgtgc ggcgaccgcc   600
ccggatgagg atggcttgca ctctgcagtg gagtcaggag ctaaggattc gaacaccacg   660
aagggagttg agtctcttgg tactggtcac aagaagatcc cgaaacgtga ggtagttgat   720
gaagttgatg ttcagacctg tgccgaagga aagaacgatt cagtggtccc ttcaagcagc   780
aagaaccca tcaatgataa gaatgcaaag gcaaatgtgg cagagaatgg acagtctgct   840
gatggtatcc ctgaggatca gagagttact attcttagtg ttgtcaagaa ggatgagcct   900
```

-continued

| | |
|---|---|
| gctgatgatg ttagagattc agttaatcct gtaacagtcg taggttatag agatgagaag | 960 |
| ggtggaacta gtggtactgc tggaactacg gctgtgcgac ctgcaggcac ccggtcatct | 1020 |
| agtttccatg gtgtgaccag gcatagatgg agtggaaaat atgaagctca tctgtgggac | 1080 |
| agttcgtgca gaatgaagg gcggagaaga aagggaaggc aagtttattt aggaagttat | 1140 |
| gataccgagg aaaaagctgc caggtcatat gatgttgcag ctcttaaata ctggggccaa | 1200 |
| aatacaaagc tgaatttctc ggtttcagaa tacgaaaggg aactggagga cataagggac | 1260 |
| atgtctcgag aggaatgcgt aacatacctg agaagaagaa gtagctgctt ctcaagaggg | 1320 |
| gcttctattt atagaggagt tactagaagg cagaaagatg ggaggtggca ggcacgcata | 1380 |
| ggactggttg ctggaacaag agacatttac ctgggaactt tcaaaactga ggaagaagca | 1440 |
| gcggaggctt acgacattgc tgctattgag atccgtggca aaaatgcggt gaccaacttt | 1500 |
| gatcgaagca actacatgga agggtatg cactgtatag aaggggcagg cttgaagctg | 1560 |
| cttgcgtcta agccagaatg aaaacttgac ttggtggagc cgcatcgcat attagggttg | 1620 |
| tttcagtcat atttggagct tantggtaca tacagataca actggttgca gcttgttaat | 1680 |
| atctctgcgt tataatctac aaattacagc tcaattttcg attgactagc aaattcgtct | 1740 |
| cagcaagaaa gattttgagc atgtattata ggttgagtag ggtagatctg tacaacacct | 1800 |
| gagcaactca atatttatgt tctgctcaat ataacctatc attcc | 1845 |

<210> SEQ ID NO 44
<211> LENGTH: 1104
<212> TYPE: DNA
<213> ORGANISM: Oryza sativa

<400> SEQUENCE: 44

| | |
|---|---|
| atggagagct ctttgaaaga ggagaaggct gcgggcgaat caggggatga tgagaaggcg | 60 |
| gagaggagct cccctatcaa tctgaattcg ttgccagcaa ctgcggcgtg tgcggcgacc | 120 |
| gccccggatg aggatggctt gcactctgca gtggagtcag gagctaagga ttcgaacacc | 180 |
| acgaagggag ttgagtctct tggtactggt cacaagaaga tcccgaaacg tgaggtagtt | 240 |
| gatgaagttg atgttcagac ctgtgccgaa ggaaagaacg attcagtggt cccttcaagc | 300 |
| agcaagaacc ctatcaatga taagaatgca aaggcaaatg tggcagagaa tggacagtct | 360 |
| gctgatggta tccctgagga tcagagagtt actattctta gtgttgtcaa gaaggatgag | 420 |
| cctgctgatg atgttagaga ttcagttaat cctgtaacag tcgtaggtta tagagatgag | 480 |
| aagggtggaa ctagtggtac tgctggaact acggctgtgc gacctgcagg cacccggtca | 540 |
| tctagttccc atggtgtgac caggcataga tggagtggaa aatatgaagc tcatctgtgg | 600 |
| gacagttcgt gcagaatgga agggcggaga agaaagggaa ggcaagttta tttaggaagt | 660 |
| tatgataccg aggaaaaagc tgccaggtca tatgatgttg cagctcttaa atactggggc | 720 |
| caaaatacaa agctgaattt ctcggtttca gaatacgaaa gggaactgga ggacataagg | 780 |
| gacatgtctc gagaggaatg cgtaacatac ctaagaagaa gaagtagctg cttctcaaga | 840 |
| ggggcttcta tttatagagg agttactaga aggcagaaag atgggaggtg gcaggcacgc | 900 |
| ataggactgg ttgctggaac aagagacatt tacctgggaa ctttcaaaac tgaggaagaa | 960 |
| gcagcggagg cttacgacat tgctgctatt gagatccgtg gcaaaaatgc ggtgaccaac | 1020 |
| tttgatcgaa gcaactacat ggagaagggt atgcactgta tagaaggggc aggcttgaag | 1080 |
| ctgcttgcgt ctaagccaga atga | 1104 |

<210> SEQ ID NO 45

```
<211> LENGTH: 367
<212> TYPE: PRT
<213> ORGANISM: Oryza sativa

<400> SEQUENCE: 45

Met Glu Ser Ser Leu Lys Glu Lys Ala Gly Glu Ser Gly Asp
 1               5                  10                  15

Asp Glu Lys Ala Glu Arg Ser Ser Pro Ile Asn Leu Asn Ser Leu Pro
            20                  25                  30

Ala Thr Ala Ala Cys Ala Ala Thr Ala Pro Asp Glu Asp Gly Leu His
        35                  40                  45

Ser Ala Val Glu Ser Gly Ala Lys Asp Ser Asn Thr Thr Lys Gly Val
    50                  55                  60

Glu Ser Leu Gly Thr Gly His Lys Lys Ile Pro Lys Arg Glu Val Val
65                  70                  75                  80

Asp Glu Val Asp Val Gln Thr Cys Ala Glu Gly Lys Asn Asp Ser Val
                85                  90                  95

Val Pro Ser Ser Ser Lys Asn Pro Ile Asn Asp Lys Asn Ala Lys Ala
            100                 105                 110

Asn Val Ala Glu Asn Gly Gln Ser Ala Asp Gly Ile Pro Glu Asp Gln
        115                 120                 125

Arg Val Thr Ile Leu Ser Val Val Lys Lys Asp Glu Pro Ala Asp Asp
    130                 135                 140

Val Arg Asp Ser Val Asn Pro Val Thr Val Val Gly Tyr Arg Asp Glu
145                 150                 155                 160

Lys Gly Gly Thr Ser Gly Thr Ala Gly Thr Thr Ala Val Arg Pro Ala
                165                 170                 175

Gly Thr Arg Ser Ser Ser Phe His Gly Val Thr Arg His Arg Trp Ser
            180                 185                 190

Gly Lys Tyr Glu Ala His Leu Trp Asp Ser Ser Cys Arg Met Glu Gly
        195                 200                 205

Arg Arg Arg Lys Gly Arg Gln Val Tyr Leu Gly Ser Tyr Asp Thr Glu
    210                 215                 220

Glu Lys Ala Ala Arg Ser Tyr Asp Val Ala Ala Leu Lys Tyr Trp Gly
225                 230                 235                 240

Gln Asn Thr Lys Leu Asn Phe Ser Val Ser Glu Tyr Glu Arg Glu Leu
                245                 250                 255

Glu Asp Ile Arg Asp Met Ser Arg Glu Glu Cys Val Thr Tyr Leu Arg
            260                 265                 270

Arg Arg Ser Ser Cys Phe Ser Arg Gly Ala Ser Ile Tyr Arg Gly Val
    275                 280                 285

Thr Arg Arg Gln Lys Asp Gly Arg Trp Gln Ala Arg Ile Gly Leu Val
290                 295                 300

Ala Gly Thr Arg Asp Ile Tyr Leu Gly Thr Phe Lys Thr Glu Glu Glu
305                 310                 315                 320

Ala Ala Glu Ala Tyr Asp Ile Ala Ala Ile Glu Ile Arg Gly Lys Asn
                325                 330                 335

Ala Val Thr Asn Phe Asp Arg Ser Asn Tyr Met Glu Lys Gly Met His
            340                 345                 350

Cys Ile Glu Gly Ala Gly Leu Lys Leu Leu Ala Ser Lys Pro Glu
    355                 360                 365

<210> SEQ ID NO 46
<211> LENGTH: 2198
<212> TYPE: DNA
<213> ORGANISM: Oryza sativa
```

```
<220> FEATURE:
<221> NAME/KEY: modified_base
<222> LOCATION: (1031)
<223> OTHER INFORMATION: a, c, g, t, unknown or other

<400> SEQUENCE: 46
ggagagagca acgcaagaac ggcacgagag gctggcagcg agcgagcgtg tgcatggttg      60
gtgcgagcaa atggccagcg gcggcggcag cagcaactgg ttaggcttct cgctctcccc     120
gcacatgccg gccatggagg tgccgtcctc ctctgagcca tcgactgctg ctcatcatca     180
tcatcatcat catccacctg ctgctgctgc tgctgccgga gccatgtcgt ctcctcccga     240
cagcgccacg acctgcaact tcctcttctc ccctcctgca gcacagatgg tcgctccttc     300
acctggctac tactacgtcg gcggcgccta cggagacggg accagcaccg ccggcgtcta     360
ctactcgcac ctccctgtca tgcctatcaa gtccgatggc tccctctgca tcatggaagg     420
catgatgccg tcgtcatcgc caaagctcga ggacttcttg gggtgtggca atggcagtgg     480
ccatgacccg gccacctact atagccaggg ccaagaagca gaggatgcaa gcagggcggc     540
ctaccagcac caccagctag tcccctacaa ctaccagcca ttgacggaag cagagatgct     600
gcaagaggcc gcagcggcgc caatggagga cgcaatggcg gcggccaaga acttcctcgt     660
caccagctac ggcgcctgct acggcaacca ggagatgccg cagccgctca gcctctccat     720
gagcccaggg tcccagtcca gcagctgcgt cagtgcagct ccccagcagc atcagcagat     780
ggcggtggtc gctgcagctg ctgctgctgg tgatggccag ggaagcaaca gtaatgacgg     840
tggcgagcag cgtgtcggga agaagagggg caccgggaaa gggggccaaa agcagcctgt     900
tcaccggaag tccattgaca cgtttgggca gaggacatcg cagtataggg gcgtcaccag     960
gcacaggtgg actggaagat atgaagccca cctctgggat aacagttgca aaaaggatgg    1020
acagacaagg naagggaagg caagtatatc taggtggtta gacactgaag ataaagctgc    1080
gagggcttat gatctggctg cgctgaaata ctggggcta tctacgcata taaatttccc    1140
gttagaaaac taccgagatg agatcgagga gatggaaagg atgacaaggc aagaatatgt    1200
tgcgcacttg agaaggagaa gcagcggggtt ctctcgcggt gcttccatct accggggagt    1260
aacaaggcat caccagcatg gaagatggca agctcggatt ggcagggttg ctggcaacaa    1320
ggacttgtat ctcggcactt tcagcactca agaagaagca gcagaggcat acgacattgc    1380
tgccatcaag ttccgtggcc tgaacgcggt gacgaacttt gacatcacaa ggtacgacgt    1440
ggacaagatc atggagagca gctcgctgct gcctggtgag gcagcgcgta aggtgaaggc    1500
gatcgaggca gcgccggacc atgtgccaat aggccgcgag ctcggtgcga ccgaggaagc    1560
gagcgctgct actgtcacgg gcaccgactg gagaatggtg ctccatggat cacagcagca    1620
gcaagctgca gcgtgcaccg aagcaacggc agatcttcag aagggcttca tgggtgacgc    1680
gcactcggct ctccacggca ttgtcgggtt cgacgtcgag tcggcggcag ctgacgagat    1740
cgatgtcccg ggagggaaga tcagtggcat caacttctcg aactcgtctt cgctggtgac    1800
tagcctgagc aactcgaggg aggggagccc tgagaggctt ggcctcgcca tgctctacgc    1860
caagcatcat cccaccgccg tcagcctcgc cgccatgaac ccctggatgc cgatgccggc    1920
gccggccgca gctcacgtga tgaggccgcc gagtgccatt gctcatctcc ctgttttgc     1980 agcctggaca gatgcttaat tagagccatg ttgctgcttg ctcgatcttg cttttgatcg    2040 gctcttttg taaactaaag caagatcagc agcaatcagg tgcttatggt acttaaatta    2100
gctggaagcc tggagtagca tacttggtta tgatggtaag cactaggctg gtggtgtaag    2160
tgtttaacca gtaaacccat aggtaggaca ttcaagca                            2198
```

<210> SEQ ID NO 47
<211> LENGTH: 1929
<212> TYPE: DNA
<213> ORGANISM: Oryza sativa
<220> FEATURE:
<221> NAME/KEY: modified_base
<222> LOCATION: (961)
<223> OTHER INFORMATION: a, c, g, t, unknown or other

<400> SEQUENCE: 47

```
atggccagcg gcggcggcag cagcaactgg ttaggcttct cgctctcccc gcacatgccg      60
gccatggagg tgccgtcctc ctctgagcca tcgactgctg ctcatcatca tcatcatcat     120
catccacctg ctgctgctgc tgctgccgga gccatgtcgt ctcctcccga cagcgccacg     180
acctgcaact tcctcttctc ccctcctgca gcacagatgg tcgctccttc acctggctac     240
tactacgtcg gcggcgccta cggagacggg accagcaccg ccggcgtcta ctactcgcac     300
ctccctgtca tgcctatcaa gtccgatggc tccctctgca tcatggaagg catgatgccg     360
tcgtcatcgc caaagctcga ggacttcttg gggtgtggca atggcagtgg ccatgacccg     420
gccacctact atagccaggg ccaagaagca gaggatgcaa gcagggcggc ctaccagcac     480
caccagctag tccctacaa ctaccagcca ttgacggaag cagagatgct gcaagaggcc     540
gcagcggcgc caatggagga cgcaatggcg gcggccaaga acttcctcgt caccagctac     600
ggcgcctgct acggcaacca ggagatgccg cagccgctca gcctctccat gagcccaggg     660
tcccagtcca gcagctgcgt cagtgcagct ccccagcagc atcagcagat ggcggtggtc     720
gctgcagctg ctgctgctgg tgatggccag ggaagcaaca gtaatgacgg tggcgagcag     780
cgtgtcggga agaagagggg cacccgggaa ggggcaaa agcagcctgt tcaccggaag     840
tccattgaca cgtttgggca gaggacatcg cagtataggg gcgtcaccag gcacaggtgg     900
actggaagat atgaagccca cctctgggat aacagttgca aaaaggatgg acagacaagg     960
naagggaagg caagtatatc taggtggtta gacactgaag ataaagctgc gagggcttat    1020
gatctggctg cgctgaaata ctggggggcta tctacgcata taaatttccc gttagaaaac    1080
taccgagatg agatcgagga gatggaaagg atgacaaggc aagaatatgt tgcgcacttg    1140
agaaggagaa gcagcgggtt ctctcgcggt gcttccatct accggggagt aacaaggcat    1200
caccagcatg gaagatggca agctcggatt ggcagggttg ctggcaacaa ggacttgtat    1260
ctcggcactt tcagcactca agaagaagca gcagaggcat acgacattgc tgccatcaag    1320
ttccgtggcc tgaacgcggt gacgaacttt gacatcacaa ggtacgacgt ggacaagatc    1380
atggagagca gctcgctgct gcctggtgag gcagcgcgta aggtgaaggc gatcgaggca    1440
gcgccggacc atgtgccaat aggccgcgag ctcggtgcga ccgaggaagc gagcgctgct    1500
actgtcacgg gcaccgactg gagaatggtg ctccatggat cacagcagca gcaagctgca    1560
gcgtgcaccg aagcaacggc agatcttcag aagggcttca tgggtgacgc gcactcggct    1620
ctccacggca ttgtcgggtt cgacgtcgag tcggcggcag ctgacgagat cgatgtcccg    1680
ggagggaaga tcagtggcat caacttctcg aactcgtctt cgctggtgac tagcctgagc    1740
aactcgaggg aggggagccc tgagaggctt ggcctcgcca tgctctacgc caagcatcat    1800
cccaccgccg tcagcctcgc cgccatgaac ccctggatgc cgatgccggc gccggccgca    1860
gctcacgtga tgaggccgcc gagtgccatt gctcatctcc ctgttttgc agcctggaca    1920
gatgcttaa                                                             1929
```

```
<210> SEQ ID NO 48
<211> LENGTH: 642
<212> TYPE: PRT
<213> ORGANISM: Oryza sativa
<220> FEATURE:
<221> NAME/KEY: misc_feature
<222> LOCATION: (321)
<223> OTHER INFORMATION: Xaa is any amino acid

<400> SEQUENCE: 48
```

| | | | | | | | | | | | | | | | |
|---|---|---|---|---|---|---|---|---|---|---|---|---|---|---|---|
| Met | Ala | Ser | Gly | Gly | Ser | Ser | Asn | Trp | Leu | Gly | Phe | Ser | Leu | Ser | |
| 1 | | | | 5 | | | | | 10 | | | | | 15 | |
| Pro | His | Met | Pro | Ala | Met | Glu | Val | Pro | Ser | Ser | Ser | Glu | Pro | Ser | Thr |
| | | | 20 | | | | | 25 | | | | | 30 | | |
| Ala | Ala | His | His | His | His | His | His | Pro | Pro | Ala | Ala | Ala | Ala | | |
| | | 35 | | | | | 40 | | | | | 45 | | | |
| Ala | Gly | Ala | Met | Ser | Ser | Pro | Pro | Asp | Ser | Ala | Thr | Thr | Cys | Asn | Phe |
| | 50 | | | | | 55 | | | | | 60 | | | | |
| Leu | Phe | Ser | Pro | Pro | Ala | Ala | Gln | Met | Val | Ala | Pro | Ser | Pro | Gly | Tyr |
| 65 | | | | | 70 | | | | | 75 | | | | | 80 |
| Tyr | Tyr | Val | Gly | Gly | Ala | Tyr | Gly | Asp | Gly | Thr | Ser | Thr | Ala | Gly | Val |
| | | | | 85 | | | | | 90 | | | | | 95 | |
| Tyr | Tyr | Ser | His | Leu | Pro | Val | Met | Pro | Ile | Lys | Ser | Asp | Gly | Ser | Leu |
| | | | 100 | | | | | 105 | | | | | 110 | | |
| Cys | Ile | Met | Glu | Gly | Met | Met | Pro | Ser | Ser | Pro | Lys | Leu | Glu | Asp | |
| | | | 115 | | | | | 120 | | | | | 125 | | |
| Phe | Leu | Gly | Cys | Gly | Asn | Gly | Ser | Gly | His | Asp | Pro | Ala | Thr | Tyr | Tyr |
| | 130 | | | | | 135 | | | | | 140 | | | | |
| Ser | Gln | Gly | Gln | Glu | Ala | Glu | Asp | Ala | Ser | Arg | Ala | Ala | Tyr | Gln | His |
| 145 | | | | | 150 | | | | | 155 | | | | | 160 |
| His | Gln | Leu | Val | Pro | Tyr | Asn | Tyr | Gln | Pro | Leu | Thr | Glu | Ala | Glu | Met |
| | | | | 165 | | | | | 170 | | | | | 175 | |
| Leu | Gln | Glu | Ala | Ala | Ala | Ala | Pro | Met | Glu | Asp | Ala | Met | Ala | Ala | |
| | | | 180 | | | | | 185 | | | | | 190 | | |
| Lys | Asn | Phe | Leu | Val | Thr | Ser | Tyr | Gly | Ala | Cys | Tyr | Gly | Asn | Gln | Glu |
| | | 195 | | | | | 200 | | | | | 205 | | | |
| Met | Pro | Gln | Pro | Leu | Ser | Leu | Ser | Met | Ser | Pro | Gly | Ser | Gln | Ser | Ser |
| | 210 | | | | | 215 | | | | | 220 | | | | |
| Ser | Cys | Val | Ser | Ala | Ala | Pro | Gln | Gln | His | Gln | Gln | Met | Ala | Val | Val |
| 225 | | | | | 230 | | | | | 235 | | | | | 240 |
| Ala | Ala | Ala | Ala | Ala | Ala | Gly | Asp | Gly | Gln | Gly | Ser | Asn | Ser | Asn | Asp |
| | | | | 245 | | | | | 250 | | | | | 255 | |
| Gly | Gly | Glu | Gln | Arg | Val | Gly | Lys | Lys | Arg | Gly | Thr | Gly | Lys | Gly | Gly |
| | | | 260 | | | | | 265 | | | | | 270 | | |
| Gln | Lys | Gln | Pro | Val | His | Arg | Lys | Ser | Ile | Asp | Thr | Phe | Gly | Gln | Arg |
| | 275 | | | | | 280 | | | | | 285 | | | | |
| Thr | Ser | Gln | Tyr | Arg | Gly | Val | Thr | Arg | His | Arg | Trp | Thr | Gly | Arg | Tyr |
| | 290 | | | | | 295 | | | | | 300 | | | | |
| Glu | Ala | His | Leu | Trp | Asp | Asn | Ser | Cys | Lys | Lys | Asp | Gly | Gln | Thr | Arg |
| 305 | | | | | 310 | | | | | 315 | | | | | 320 |
| Xaa | Gly | Lys | Ala | Ser | Ile | Ser | Arg | Trp | Leu | Asp | Thr | Glu | Asp | Lys | Ala |
| | | | | 325 | | | | | 330 | | | | | 335 | |
| Ala | Arg | Ala | Tyr | Asp | Leu | Ala | Ala | Leu | Lys | Tyr | Trp | Gly | Leu | Ser | Thr |
| | | | 340 | | | | | 345 | | | | | 350 | | |
| His | Ile | Asn | Phe | Pro | Leu | Glu | Asn | Tyr | Arg | Asp | Glu | Ile | Glu | Glu | Met |
| | | | 355 | | | | | 360 | | | | | 365 | | |

```
Glu Arg Met Thr Arg Gln Glu Tyr Val Ala His Leu Arg Arg Ser
        370                 375                 380

Ser Gly Phe Ser Arg Gly Ala Ser Ile Tyr Arg Gly Val Thr Arg His
385                 390                 395                 400

His Gln His Gly Arg Trp Gln Ala Arg Ile Gly Arg Val Ala Gly Asn
                405                 410                 415

Lys Asp Leu Tyr Leu Gly Thr Phe Ser Thr Gln Glu Glu Ala Ala Glu
            420                 425                 430

Ala Tyr Asp Ile Ala Ala Ile Lys Phe Arg Gly Leu Asn Ala Val Thr
        435                 440                 445

Asn Phe Asp Ile Thr Arg Tyr Asp Val Asp Lys Ile Met Glu Ser Ser
    450                 455                 460

Ser Leu Leu Pro Gly Glu Ala Ala Arg Lys Val Lys Ala Ile Glu Ala
465                 470                 475                 480

Ala Pro Asp His Val Pro Ile Gly Arg Glu Leu Gly Ala Thr Glu Glu
                485                 490                 495

Ala Ser Ala Ala Thr Val Thr Gly Thr Asp Trp Arg Met Val Leu His
            500                 505                 510

Gly Ser Gln Gln Gln Ala Ala Cys Thr Glu Thr Ala Asp
        515                 520                 525

Leu Gln Lys Gly Phe Met Gly Asp Ala His Ser Ala Leu His Gly Ile
    530                 535                 540

Val Gly Phe Asp Val Glu Ser Ala Ala Ala Asp Glu Ile Asp Val Pro
545                 550                 555                 560

Gly Gly Lys Ile Ser Gly Ile Asn Phe Ser Asn Ser Ser Leu Val
                565                 570                 575

Thr Ser Leu Ser Asn Ser Arg Glu Gly Ser Pro Glu Arg Leu Gly Leu
            580                 585                 590

Ala Met Leu Tyr Ala Lys His His Pro Thr Ala Val Ser Leu Ala Ala
        595                 600                 605

Met Asn Pro Trp Met Pro Met Pro Ala Pro Ala Ala His Val Met
    610                 615                 620

Arg Pro Pro Ser Ala Ile Ala His Leu Pro Val Phe Ala Ala Trp Thr
625                 630                 635                 640

Asp Ala
```

<210> SEQ ID NO 49
<211> LENGTH: 2084
<212> TYPE: DNA
<213> ORGANISM: Triticum aestivum

<400> SEQUENCE: 49

```
atttcgtatt aataaaacga gcactatttt attttctac  tgtatttac  tcctggtgta    60
gtgctgccag aaaccgctgc aggtggtagc agtaaaagat ccagcaaata tccgatggtt   120
tcagagcgcc agtgcggcgg cgccctgtca agcgcgagat aaaatccgcc ggaccccgc   180
gatttccccc actccgcgtt tcctctctcg atttgtccaa atcttttgtt ctccttctcc   240
accggcgatt agtttgttgt ttccggcatc actccgcact aggccgcccc tcgccgcgc   300
tggcctcgtc gtttccttcc ccaattccgc cgcccaccc  cgcccgatat ttatttcctg   360
cctcggtatc catttccgtt gatagatttt tccagctttc gctgcctcgc cgttgctgct   420
aatatccgcg ctgggatatt tcttcttttg ctttcttggc cgcgcggctc ggcccgtccc   480
cctggaggcc tccggatctt tcgatcgcgg cgagcaggcg gctcaagata gttcgtgaat   540
aggaaggctg ataggtaggt tagggttttg ggagttgttt ttgtctctgc tccagtacat   600
```

```
agatgatgaa atccggggag gaagttagtc agggtcagca aatgaacggt tttgtggagg    660
agaaagctgc tggggaatct ggggatggtc ggaagatcga gaggagccct tccatcaatc    720
tgaattcctt gcctgcaatt gcccctgcca ctacggagat tggtgtcttg cactgtgcag    780
tggagtcaga ggccaacgat gcaagcactc agaagggaga tgagtccagt ggcactgatc    840
agaagaaggt cccgaagaat gaggaggttg atgaaggtga agttcaggcc tgtgcagatg    900
tgaagagcca ctcggttgac cctttgaata gcgagaacca tgccggggag aaggatgctt    960
tggtaactgt gccagaaaat gagggttgtg cggatggtgg cgataattat aagggagttc   1020
aagttctcag cattgtcaaa aggacgagtc tgaggaaat tgttgattct attaatcctg    1080
tgacggttgc ggagtataga gaggagaagg gcaccgccgg ttctacttct gcaattactg   1140
cggtgcgagc acctggctcc cgctcatctt gtttccatgg tgtgaccagg cataggtgga   1200
gtgggaaata tgaagctcat tgtgggaca gtacttgcag agtagaagga cggagaagga    1260
aaggaaagca agtttattta ggaagttatg atactgagca aaaagctgcc agggcatatg   1320
atgttgcagc tcttaaattc tttggactaa atacaaagct gaacttctca atttcggaat   1380
atgagaagga actggcggac atacaagaca tgtctccaga ggaatgtgtg acatactggg   1440 aagggggag tagttgcttc tcaagagggg cgtctattta cagaggagtt acaaggaggc    1500
agaaagatgg tcgatggcag gcacgcatag gactgattgc tggaactaga gacatttacc   1560
ttggaacttt caaaactgag gaagaagccg cagaagctta tgatattgct gccatcgaga   1620
tacgcggcaa aaatgcggtg accaactttg acagaagcaa ctacatggac aggggcatgc   1680
attgtataga aggcgcaggg ttgaagctgc ttgcaaccaa gccagaatag tacctgattt   1740
ggcatcgtat attgaacaga tttggttggc cgtattttgg agcctagtgg tacatacaga   1800
tagaagaact ggtcgcagcc tgtcattatc cgctgctgta tgattcttca gattatatat   1860
agttctttca gatagaattt cagtaattta gcatgctttg tgtccagaca agattttgac   1920
catgcattac tgttatagtg tttgtaggct agagttgcag tggaagatgt tgcttcattt   1980
cacatgtcta atcggagaa tacgttttac ttctaagttt tgatgcttgg tttaatgaaa    2040
tattcaagtg tatgttccaa aaaaaaaaaa aaaaaagcgg ccgc                    2084
```

<210> SEQ ID NO 50
<211> LENGTH: 1128
<212> TYPE: DNA
<213> ORGANISM: Triticum aestivum

<400> SEQUENCE: 50

```
atgatgaaat ccggggagga agttagtcag ggtcagcaaa tgaacggttt tgtggaggag     60
aaagctgctg ggaatctggg gatggtcgg aagatcgaga ggagcccttc catcaatctg    120
aattccttgc ctgcaattgc ccctgccact acggagattg tgtcttgca ctgtgcagtg    180 gagtcagagg ccaacgatgc aagcactcag aagggagatg agtccagtgg cactgatcag   240
aagaaggtcc cgaagaatga ggaggttgat gaaggtgaag ttcaggcctg tgcagatgtg   300
aagagccact cggttgaccc tttgaatagc gagaaccatg ccggggagaa ggatgctttg   360
gtaactgtgc cagaaaatga gggttgtgcg gatggtggcg ataattataa gggagttcaa   420
gttctcagca ttgtcaaaaa ggacgagtct gaggaaattg ttgattctat taatcctgtg   480
acggttgcgg agtatagaga ggagaagggc accgccggtt ctacttctgc aattactgcg   540
gtgcgagcac ctggctcccg ctcatcttgt ttccatggtg tgaccaggca taggtggagt   600
gggaaatatg aagctcattt gtgggacagt acttgcagag tagaaggacg agaaggaaa    660
```

```
ggaaagcaag tttatttagg aagttatgat actgagcaaa aagctgccag ggcatatgat    720
gttgcagctc ttaaattctt tggactaaat acaaagctga acttctcaat ttcggaatat    780
gagaaggaac tggcggacat acaagacatg tctccagagg aatgtgtgac atacttgaga    840
aggaggagta gttgcttctc aagagggggcg tctatttaca gaggagttac aaggaggcag    900
```

```
ggaaagcaag tttatttagg aagttatgat actgagcaaa aagctgccag ggcatatgat    720
gttgcagctc ttaaattctt tggactaaat acaaagctga acttctcaat ttcggaatat    780
gagaaggaac tggcggacat acaagacatg tctccagagg aatgtgtgac atacttgaga    840
aggaggagta gttgcttctc aagagggcg tctatttaca gaggagttac aaggaggcag    900
aaagatggtc gatggcaggc acgcatagga ctgattgctg aactagaga catttacctt    960 ggaactttca aaactgagga agaagccgca gaagcttatg atattgctgc catcgagata   1020
cgcggcaaaa atgcggtgac caactttgac agaagcaact acatggacag ggcatgcat   1080 tgtatagaag gcgcagggtt gaagctgctt gcaaccaagc cagaatag                1128
```

<210> SEQ ID NO 51
<211> LENGTH: 375
<212> TYPE: PRT
<213> ORGANISM: Triticum aestivum

<400> SEQUENCE: 51

Met Met Lys Ser Gly Glu Val Ser Gln Gly Gln Gln Met Asn Gly
1               5                   10                  15

Phe Val Glu Glu Lys Ala Ala Gly Glu Ser Gly Asp Gly Arg Lys Ile
            20                  25                  30

Glu Arg Ser Pro Ser Ile Asn Leu Asn Ser Leu Pro Ala Ile Ala Pro
        35                  40                  45

Ala Thr Thr Glu Ile Gly Val Leu His Cys Ala Val Glu Ser Glu Ala
    50                  55                  60

Asn Asp Ala Ser Thr Gln Lys Gly Asp Glu Ser Ser Gly Thr Asp Gln
65                  70                  75                  80

Lys Lys Val Pro Lys Asn Glu Glu Val Asp Glu Gly Glu Val Gln Ala
                85                  90                  95

Cys Ala Asp Val Lys Ser His Ser Val Asp Pro Leu Asn Ser Glu Asn
            100                 105                 110

His Ala Gly Glu Lys Asp Ala Leu Val Thr Val Pro Glu Asn Glu Gly
        115                 120                 125

Cys Ala Asp Gly Gly Asp Asn Tyr Lys Gly Val Gln Val Leu Ser Ile
    130                 135                 140

Val Lys Lys Asp Glu Ser Glu Glu Ile Val Asp Ser Ile Asn Pro Val
145                 150                 155                 160

Thr Val Ala Glu Tyr Arg Glu Glu Lys Gly Thr Ala Gly Ser Thr Ser
                165                 170                 175

Ala Ile Thr Ala Val Arg Ala Pro Gly Ser Arg Ser Ser Cys Phe His
            180                 185                 190

Gly Val Thr Arg His Arg Trp Ser Gly Lys Tyr Glu Ala His Leu Trp
        195                 200                 205

Asp Ser Thr Cys Arg Val Glu Gly Arg Arg Lys Gly Lys Gln Val
    210                 215                 220

Tyr Leu Gly Ser Tyr Asp Thr Glu Gln Lys Ala Ala Arg Ala Tyr Asp
225                 230                 235                 240

Val Ala Ala Leu Lys Phe Phe Gly Leu Asn Thr Lys Leu Asn Phe Ser
                245                 250                 255

Ile Ser Glu Tyr Glu Lys Glu Leu Ala Asp Ile Gln Asp Met Ser Pro
            260                 265                 270

Glu Glu Cys Val Thr Tyr Leu Arg Arg Arg Ser Ser Cys Phe Ser Arg
        275                 280                 285

Gly Ala Ser Ile Tyr Arg Gly Val Thr Arg Arg Gln Lys Asp Gly Arg
```

```
                 290                 295                 300
Trp Gln Ala Arg Ile Gly Leu Ile Ala Gly Thr Arg Asp Ile Tyr Leu
305                 310                 315                 320

Gly Thr Phe Lys Thr Glu Glu Ala Ala Glu Ala Tyr Asp Ile Ala
                325                 330                 335

Ala Ile Glu Ile Arg Gly Lys Asn Ala Val Thr Asn Phe Asp Arg Ser
                340                 345                 350

Asn Tyr Met Asp Arg Gly Met His Cys Ile Glu Gly Ala Gly Leu Lys
            355                 360                 365

Leu Leu Ala Thr Lys Pro Glu
    370                 375

<210> SEQ ID NO 52
<211> LENGTH: 2103
<212> TYPE: DNA
<213> ORGANISM: Glycine max

<400> SEQUENCE: 52
gcccttaagc agtggtaaca acgcagagta cgcggggatt cattttcatt caacccttct      60
ctctctctct ctcagataga ttctataaga tcgcagtttc caaagaagct aactgaagtt     120
caaaccccca taacctctct ttcacgttcc tcaacgacac ataaaacaca caccatggac     180
tcttcttctt catcaccgcc aaacagcacc aacaacaact ccctcgcttt ctctctttcc     240
aatcactttc ccaacccttc ttcctctccc ctttctctct tccactcctt cacctatcca     300
tctctctctc tcacaggcag caacacggtg gacgcaccgc tgagcccac cgctggagca      360 ggaccgacca acctctccat attcaccggc ggccccaagt tcgaggactt ctgggcggt      420 tccgccgcaa cagccaccac cgtcgcgtgt gcaccgccac agcttccgca gttctccacc     480
gacaacaaca accacctata cgattcggag ctgaagtcaa caatagccgc gtgcttccct     540
cgcgccttgg ccgccgaaca aagcaccgaa ccgcaaaaac catcccccaa gaaaaccgtc     600
gacaccttcg ggcaacgcac ctccatctac cgcggcgtga cccgacatag atggactggg     660
agatacgaag ctcatctatg gacaatagt tgcagaaggg aaggtcaaag caggaaagga      720
aggcaagttt acttgggtgg ttatgacaag gaggataagg cagccagagc ttatgatctc     780
gcagctctca gtactgggg tccaactacc accactaact ttcctatttc caactatgag      840
aaggaactgg aggagatgaa gaacatgact aggcaagagt ttgttgcttc tcttcgtagg     900
aagagcagtg gtttctctag agggcctct atatacagag gagtaacgag acaccaccag      960
catggccgat ggcaggcgag aataggcaga gttgccggaa acaaagacct ctaccttggc    1020
actttcagca cccaagaaga agctgctgag gcctatgaca ttgctgctat caaattcagg    1080
ggattaaatg cagtaacaaa ctttgacatg agtcgctacg acgtgaagag cattgcaaat    1140
agtactcttc ctattggtgg tttatctggc aagaacaaga actccacaga ttctgcatct    1200
gagagcaaaa gccatgagcc aagccaatcc gatggagatc catcatcggc ttcatcggtg    1260
acctttgcat cacagcaaca accttcaagc tccaacttaa gctttgccat acccattaag    1320
caagacccct cagattactg gtccatcttg gggtaccata atactcccct tgacaacagt    1380
ggcatcagga acactactag tactgttact acaactactt ttccatcctc caacaatggc    1440
actgctagta gtttgacacc cttcaacatg gagttctcaa gtgcccctc aagtaccggc    1500 agcgataaca atgccgcgtt tttcagtgga ggaggcatct tgttcagca acaaactagt    1560 catggtcatg gaaatgcaag cagtggttcc tcctcttctt ctttaagctg ttcaatccca    1620
ttcgccacgc ccatattttc tctaaatagc aatactagtt atgagagcag tgctggttat    1680
```

| | |
|---|---|
| ggaaactgga ttggacctac cctgcacaca ttccaatccc atgcaaaacc aagtctcttt | 1740 |
| caaacgccaa tatttggaat ggaatgagct catgcacgag ctgggatgag aatctgtgca | 1800 |
| tataatgatg aaaggggaag aaggacaata gtggtgatgg tgttttagca tgcaaagaag | 1860 |
| caaaggacgg actagtccct ttagctgatg cagtatttga atgagttgga ctgacagtca | 1920 |
| taatttcatg agaatcgtag ctatacctag cagctgacac tgtactaact caaacttcct | 1980 |
| ttgttatgtt ttgaatgaat tttcctttt cttttcgcc cctttattag cttttggtc | 2040 |
| ctgttaatat actgacatta tatcaaatga ggataatggg aagaaaaaaa aaatccttt | 2100 |
| gtt | 2103 |

<210> SEQ ID NO 53
<211> LENGTH: 1593
<212> TYPE: DNA
<213> ORGANISM: Glycine max

<400> SEQUENCE: 53

| | |
|---|---|
| atggactctt cttcttcatc accgccaaac agcaccaaca caactccct cgctttctct | 60 |
| cttccaatc actttcccaa cccttcttcc tctccccttt ctctcttcca ctccttcacc | 120 |
| tatccatctc tctctctcac aggcagcaac acggtggacg caccgcctga gcccaccgct | 180 |
| ggagcaggac cgaccaacct ctccatattc accggcggcc ccaagttcga ggactttctg | 240 |
| gcggttccg ccgcaacagc caccaccgtc gcgtgtgcac cgccacagct ccgcagttc | 300 |
| tccaccgaca caacaacca cctatacgat tcggagctga agtcaacaat agccgcgtgc | 360 |
| ttccctcgcg ccttggccgc cgaacaaagc accgaaccgc aaaaaccatc ccccaagaaa | 420 |
| accgtcgaca ccttcgggca acgcacctcc atctaccgcg gcgtgacccg acatagatgg | 480 |
| actgggagat acgaagctca tctatgggac aatagttgca aagggaagg tcaaagcagg | 540 |
| aaaggaaggc aagtttactt gggtggttat gacaaggagg ataaggcagc cagagcttat | 600 |
| gatctcgcag ctctcaagta ctggggtcca actaccacca ctaactttcc tatttccaac | 660 |
| tatgagaagg aactggagga gatgaagaac atgactaggc aagagtttgt tgcttctctt | 720 |
| cgtaggaaga gcagtggttt tctctagaggg gcctctatat acagaggagt aacgagacac | 780 |
| caccagcatg gccgatggca ggcgagaata ggcagagttg ccggaaacaa agacctctac | 840 |
| cttggcactt tcagcaccca agaagaagct gctgaggcct atgacattgc tgctatcaaa | 900 |
| ttcaggggat taaatgcagt aacaaacttt gacatgagtc gctacgacgt gaagagcatt | 960 |
| gcaaatagta ctcttcctat tggtggttta tctggcaaga caagaactc cacagattct | 1020 |
| gcatctgaga gcaaaagcca tgagccaagc caatccgatg gagatccatc atcggcttca | 1080 |
| tcggtgacct ttgcatcaca gcaacaacct tcaagctcca acttaagctt tgccataccc | 1140 |
| attaagcaag acccttcaga ttactggtcc atcttggggt accataatac tccccttgac | 1200 |
| aacagtggca tcaggaacac tactagtact gttactacaa ctacttttcc atcctccaac | 1260 |
| aatggcactg ctagtagttt gacacccttc aacatggagt tctcaagtgc ccctcaagt | 1320 |
| accggcagcg ataacaatgc cgcgttttc agtggaggag gcatctttgt tcagcaacaa | 1380 |
| actagtcatg gtcatggaaa tgcaagcagt ggttcctcct cttcttcttt aagctgttca | 1440 |
| atcccattcg ccacgcccat attttctcta aatagcaata ctagttatga gagcagtgct | 1500 |
| ggttatggaa actggattgg acctacctg cacacattcc aatcccatgc aaaaccaagt | 1560 |
| ctctttcaaa cgccaatatt tggaatggaa tga | 1593 |

<210> SEQ ID NO 54
<211> LENGTH: 530
<212> TYPE: PRT
<213> ORGANISM: Glycine max

<400> SEQUENCE: 54

```
Met Asp Ser Ser Ser Ser Pro Pro Asn Ser Thr Asn Asn Asn Ser
 1               5                  10                  15

Leu Ala Phe Ser Leu Ser Asn His Phe Pro Asn Pro Ser Ser Ser Pro
                20                  25                  30

Leu Ser Leu Phe His Ser Phe Thr Tyr Pro Ser Leu Ser Leu Thr Gly
                35                  40                  45

Ser Asn Thr Val Asp Ala Pro Pro Glu Pro Thr Ala Gly Ala Gly Pro
            50                  55                  60

Thr Asn Leu Ser Ile Phe Thr Gly Gly Pro Lys Phe Glu Asp Phe Leu
 65                  70                  75                  80

Gly Gly Ser Ala Ala Thr Ala Thr Thr Val Ala Cys Ala Pro Pro Gln
                85                  90                  95

Leu Pro Gln Phe Ser Thr Asp Asn Asn Asn His Leu Tyr Asp Ser Glu
                100                 105                 110

Leu Lys Ser Thr Ile Ala Ala Cys Phe Pro Arg Ala Leu Ala Ala Glu
            115                 120                 125

Gln Ser Thr Glu Pro Gln Lys Pro Ser Pro Lys Lys Thr Val Asp Thr
130                 135                 140

Phe Gly Gln Arg Thr Ser Ile Tyr Arg Gly Val Thr Arg His Arg Trp
145                 150                 155                 160

Thr Gly Arg Tyr Glu Ala His Leu Trp Asp Asn Ser Cys Arg Arg Glu
                165                 170                 175

Gly Gln Ser Arg Lys Gly Arg Gln Val Tyr Leu Gly Gly Tyr Asp Lys
                180                 185                 190

Glu Asp Lys Ala Ala Arg Ala Tyr Asp Leu Ala Ala Leu Lys Tyr Trp
            195                 200                 205

Gly Pro Thr Thr Thr Thr Asn Phe Pro Ile Ser Asn Tyr Glu Lys Glu
210                 215                 220

Leu Glu Glu Met Lys Asn Met Thr Arg Gln Glu Phe Val Ala Ser Leu
225                 230                 235                 240

Arg Arg Lys Ser Ser Gly Phe Ser Arg Gly Ala Ser Ile Tyr Arg Gly
                245                 250                 255

Val Thr Arg His His Gln His Gly Arg Trp Gln Ala Arg Ile Gly Arg
                260                 265                 270

Val Ala Gly Asn Lys Asp Leu Tyr Leu Gly Thr Phe Ser Thr Gln Glu
            275                 280                 285

Glu Ala Ala Glu Ala Tyr Asp Ile Ala Ala Ile Lys Phe Arg Gly Leu
290                 295                 300

Asn Ala Val Thr Asn Phe Asp Met Ser Arg Tyr Asp Val Lys Ser Ile
305                 310                 315                 320

Ala Asn Ser Thr Leu Pro Ile Gly Gly Leu Ser Gly Lys Asn Lys Asn
                325                 330                 335

Ser Thr Asp Ser Ala Ser Glu Ser Lys Ser His Glu Pro Ser Gln Ser
                340                 345                 350

Asp Gly Asp Pro Ser Ser Ala Ser Ser Val Thr Phe Ala Ser Gln Gln
            355                 360                 365

Gln Pro Ser Ser Ser Asn Leu Ser Phe Ala Ile Pro Ile Lys Gln Asp
370                 375                 380

Pro Ser Asp Tyr Trp Ser Ile Leu Gly Tyr His Asn Thr Pro Leu Asp
```

```
                    385                 390                 395                 400
Asn Ser Gly Ile Arg Asn Thr Thr Ser Thr Val Thr Thr Thr Phe
                    405                 410                 415

Pro Ser Asn Asn Gly Thr Ala Ser Ser Leu Thr Pro Phe Asn Met
                    420                 425                 430

Glu Phe Ser Ser Ala Pro Ser Ser Thr Gly Ser Asp Asn Asn Ala Ala
                    435                 440                 445

Phe Phe Ser Gly Gly Gly Ile Phe Val Gln Gln Gln Thr Ser His Gly
            450                 455                 460

His Gly Asn Ala Ser Ser Gly Ser Ser Ser Ser Leu Ser Cys Ser
465                 470                 475                 480

Ile Pro Phe Ala Thr Pro Ile Phe Ser Leu Asn Ser Asn Thr Ser Tyr
                    485                 490                 495

Glu Ser Ser Ala Gly Tyr Gly Asn Trp Ile Gly Pro Thr Leu His Thr
                500                 505                 510

Phe Gln Ser His Ala Lys Pro Ser Leu Phe Gln Thr Pro Ile Phe Gly
            515                 520                 525

Met Glu
    530

<210> SEQ ID NO 55
<211> LENGTH: 2193
<212> TYPE: DNA
<213> ORGANISM: Glycine max
<220> FEATURE:
<221> NAME/KEY: modified_base
<222> LOCATION: (1261)
<223> OTHER INFORMATION: a, c, g, t, unknown or other
<220> FEATURE:
<221> NAME/KEY: modified_base
<222> LOCATION: (1279)
<223> OTHER INFORMATION: a, c, g, t, unknown or other
<220> FEATURE:
<221> NAME/KEY: modified_base
<222> LOCATION: (1318)
<223> OTHER INFORMATION: a, c, g, t, unknown or other
<220> FEATURE:
<221> NAME/KEY: modified_base
<222> LOCATION: (1358)
<223> OTHER INFORMATION: a, c, g, t, unknown or other
<220> FEATURE:
<221> NAME/KEY: modified_base
<222> LOCATION: (1362)
<223> OTHER INFORMATION: a, c, g, t, unknown or other
<220> FEATURE:
<221> NAME/KEY: modified_base
<222> LOCATION: (1373)
<223> OTHER INFORMATION: a, c, g, t, unknown or other
<220> FEATURE:
<221> NAME/KEY: modified_base
<222> LOCATION: (1380)
<223> OTHER INFORMATION: a, c, g, t, unknown or other
<220> FEATURE:
<221> NAME/KEY: modified_base
<222> LOCATION: (1384)
<223> OTHER INFORMATION: a, c, g, t, unknown or other
<220> FEATURE:
<221> NAME/KEY: modified_base
<222> LOCATION: (1388)
<223> OTHER INFORMATION: a, c, g, t, unknown or other
<220> FEATURE:
<221> NAME/KEY: modified_base
<222> LOCATION: (1394)
<223> OTHER INFORMATION: a, c, g, t, unknown or other
<220> FEATURE:
<221> NAME/KEY: modified_base
<222> LOCATION: (1410)
<223> OTHER INFORMATION: a, c, g, t, unknown or other
<220> FEATURE:
<221> NAME/KEY: modified_base
```

```
<222> LOCATION: (1428)
<223> OTHER INFORMATION: a, c, g, t, unknown or other
<220> FEATURE:
<221> NAME/KEY: modified_base
<222> LOCATION: (1436)
<223> OTHER INFORMATION: a, c, g, t, unknown or other
<220> FEATURE:
<221> NAME/KEY: modified_base
<222> LOCATION: (1441)
<223> OTHER INFORMATION: a, c, g, t, unknown or other
<220> FEATURE:
<221> NAME/KEY: modified_base
<222> LOCATION: (1459)
<223> OTHER INFORMATION: a, c, g, t, unknown or other
<220> FEATURE:
<221> NAME/KEY: modified_base
<222> LOCATION: (1479)
<223> OTHER INFORMATION: a, c, g, t, unknown or other
<220> FEATURE:
<221> NAME/KEY: modified_base
<222> LOCATION: (1481)
<223> OTHER INFORMATION: a, c, g, t, unknown or other
<220> FEATURE:
<221> NAME/KEY: modified_base
<222> LOCATION: (1488)
<223> OTHER INFORMATION: a, c, g, t, unknown or other
<220> FEATURE:
<221> NAME/KEY: modified_base
<222> LOCATION: (1492)
<223> OTHER INFORMATION: a, c, g, t, unknown or other
<220> FEATURE:
<221> NAME/KEY: modified_base
<222> LOCATION: (1503)
<223> OTHER INFORMATION: a, c, g, t, unknown or other
<220> FEATURE:
<221> NAME/KEY: modified_base
<222> LOCATION: (1515)
<223> OTHER INFORMATION: a, c, g, t, unknown or other
<220> FEATURE:
<221> NAME/KEY: modified_base
<222> LOCATION: (1524)
<223> OTHER INFORMATION: a, c, g, t, unknown or other
<220> FEATURE:
<221> NAME/KEY: modified_base
<222> LOCATION: (1549)
<223> OTHER INFORMATION: a, c, g, t, unknown or other
<220> FEATURE:
<221> NAME/KEY: modified_base
<222> LOCATION: (1551)
<223> OTHER INFORMATION: a, c, g, t, unknown or other
<220> FEATURE:
<221> NAME/KEY: modified_base
<222> LOCATION: (1572)
<223> OTHER INFORMATION: a, c, g, t, unknown or other
<220> FEATURE:
<221> NAME/KEY: modified_base
<222> LOCATION: (1603)
<223> OTHER INFORMATION: a, c, g, t, unknown or other
<220> FEATURE:
<221> NAME/KEY: modified_base
<222> LOCATION: (1644)
<223> OTHER INFORMATION: a, c, g, t, unknown or other

<400> SEQUENCE: 55
gggctgtttc cgtcgatgag accacaactc gactgtgtaa cagggtaatc aaaatagata    60
aaataaaaaa tatacttcct ttgaccggtg accgtgcgaa ccggttcgaa gttggaacca   120
tgagagagat aatgtttata tattccatca tctgttccgt ttggatcctc tcacctctct   180
ctctctctct ctctctggtg ccatggaatc cggtagtgcc cgatgtttat attctctctg   240
gttctgaaat catcgccgag gaaataacaa atgcagcctc caaacctcgc gaagcttcct   300
tcacacactt ccttctattc cttgttcgtc gaacaagctc tttaacattc catcaccaca   360
acttcctacc tacaccttcc gatattgcat cttcaactgt tggttacat ttcacacgta    420 ataattattg tttctttcga ttggatcggt cggaaccatc gctcgaagag aatctccgga   480
```

```
gacgtagaag caatatcagt ttactgtatg tattggttcg gattaataat aataacgaaa      540
aaatagaaag aaaatcagag ttgaaaatag ccagaagaag attaagcgcg atgttggatc      600
ttaatctgaa tgccgagtcg actcagaaca acgagtcgct ggtgctgttg acaagtttc       660 ccgaagcttc gttgggaact tcgaattcct ccgtcgtgaa tgcggaggga tcgagcaacg      720
aggactcgtg ctccacacgc gccggcgacg tgttcgcctt cagtttcgga atccttaagg     780
tggaaggcgc gaacgaagtc gtcgccacgg cgacgaagga gctgtttccg gtgagctcgg     840
agaattggca ggggcagagt tcgacgtcgt cgtctcaggc gaggaagaat ttaatggatc      900
tcccgctgga tcatcaaaac ggtgaggtga aggtggttca ggttcagcca cagcctcagg     960
tgaagaagag taggagaggt ccaaggtctc ggagctctca gtacagagga gtcactttct    1020
acagaaggac cggaagatgg gaatcgcata tctgggattg cgggaagcaa gtctatttgg    1080
gtggatttga caccgctcat attgctgcta gggcctatga tcgaactgct attaagttca    1140
ggggacttga tgctgatatc aatttttgatc tcgttgatta tgaggaggat ctaaaacaga    1200
tgaagaatct ttcaagcagg agttcgtgca catacttcgc cgccacagta ccggttctca    1260
ngggcagttc gaaataccng gatacacttc acaagtggc cttgggaact cgatgggnat      1320
tcctggcaga agctatacag gcacttcagt gcataaanaa gntgtcctac ttnaccattn    1380
ttgnacgnag aacngagctt catcctggan aggtagcagg cgtttcangc aagagnaggt    1440 ncctattga gccagaatng ggaggagaga accggagtnt naagaagngg cntccggcct     1500
ggnctcaatt gggcnagcaa cccnagacat gtcccaaaga aaatagggnc nttttcagtt    1560
ccagtccatc cnttacaaca tgcatccggg aagaagttca agnatggaga ctaatgttaa    1620
ttcggttatt ggtgatcctt cttngaaaag gctggttgta cgaagagcgt ccttctgtat    1680
attccacttt cttttcccaat ctggaaagag cagagagaat gggcatagat ccttcaaaag    1740
gagttccaaa ctgggcgtgg cagacaaatg gccaggttaa tgccaccca gtaccaccgt     1800 tctctactgc agcatcatca ggattctcaa tttcagctac ttttccatca actgccatct    1860
ttccaacaaa atccatgaac ccaattcccc agagcttctg tttcacttca cacagcacac    1920
caggtagcaa tgcacctcaa ttctattacg aggtcaagtc ctcgcaggca ccatcccagc    1980
ctctatcttg taatacaagt ataaatggta gcccaccaca caagttctga agttcaattc    2040
tcaaaacgac agttaaaact ttttttttttt tttttcctgt ttgcatgatt tagggatcgg    2100
tacaatgttg ttgctcatgg tatgtttgta tgtgatgaaa agatttttttt cttcagagag   2160 aaagtgaaaa gaaaaaatgc atgatgtgtt tta                                  2193
```

<210> SEQ ID NO 56
<211> LENGTH: 1911
<212> TYPE: DNA
<213> ORGANISM: Glycine max
<220> FEATURE:
<221> NAME/KEY: modified_base
<222> LOCATION: (1142)
<223> OTHER INFORMATION: a, c, g, t, unknown or other
<220> FEATURE:
<221> NAME/KEY: modified_base
<222> LOCATION: (1160)
<223> OTHER INFORMATION: a, c, g, t, unknown or other
<220> FEATURE:
<221> NAME/KEY: modified_base
<222> LOCATION: (1199)
<223> OTHER INFORMATION: a, c, g, t, unknown or other
<220> FEATURE:
<221> NAME/KEY: modified_base
<222> LOCATION: (1239)
<223> OTHER INFORMATION: a, c, g, t, unknown or other

```
<220> FEATURE:
<221> NAME/KEY: modified_base
<222> LOCATION: (1243)
<223> OTHER INFORMATION: a, c, g, t, unknown or other
<220> FEATURE:
<221> NAME/KEY: modified_base
<222> LOCATION: (1254)
<223> OTHER INFORMATION: a, c, g, t, unknown or other
<220> FEATURE:
<221> NAME/KEY: modified_base
<222> LOCATION: (1261)
<223> OTHER INFORMATION: a, c, g, t, unknown or other
<220> FEATURE:
<221> NAME/KEY: modified_base
<222> LOCATION: (1265)
<223> OTHER INFORMATION: a, c, g, t, unknown or other
<220> FEATURE:
<221> NAME/KEY: modified_base
<222> LOCATION: (1269)
<223> OTHER INFORMATION: a, c, g, t, unknown or other
<220> FEATURE:
<221> NAME/KEY: modified_base
<222> LOCATION: (1275)
<223> OTHER INFORMATION: a, c, g, t, unknown or other
<220> FEATURE:
<221> NAME/KEY: modified_base
<222> LOCATION: (1291)
<223> OTHER INFORMATION: a, c, g, t, unknown or other
<220> FEATURE:
<221> NAME/KEY: modified_base
<222> LOCATION: (1309)
<223> OTHER INFORMATION: a, c, g, t, unknown or other
<220> FEATURE:
<221> NAME/KEY: modified_base
<222> LOCATION: (1317)
<223> OTHER INFORMATION: a, c, g, t, unknown or other
<220> FEATURE:
<221> NAME/KEY: modified_base
<222> LOCATION: (1322)
<223> OTHER INFORMATION: a, c, g, t, unknown or other
<220> FEATURE:
<221> NAME/KEY: modified_base
<222> LOCATION: (1340)
<223> OTHER INFORMATION: a, c, g, t, unknown or other
<220> FEATURE:
<221> NAME/KEY: modified_base
<222> LOCATION: (1360)
<223> OTHER INFORMATION: a, c, g, t, unknown or other
<220> FEATURE:
<221> NAME/KEY: modified_base
<222> LOCATION: (1362)
<223> OTHER INFORMATION: a, c, g, t, unknown or other
<220> FEATURE:
<221> NAME/KEY: modified_base
<222> LOCATION: (1369)
<223> OTHER INFORMATION: a, c, g, t, unknown or other
<220> FEATURE:
<221> NAME/KEY: modified_base
<222> LOCATION: (1373)
<223> OTHER INFORMATION: a, c, g, t, unknown or other
<220> FEATURE:
<221> NAME/KEY: modified_base
<222> LOCATION: (1384)
<223> OTHER INFORMATION: a, c, g, t, unknown or other
<220> FEATURE:
<221> NAME/KEY: modified_base
<222> LOCATION: (1396)
<223> OTHER INFORMATION: a, c, g, t, unknown or other
<220> FEATURE:
<221> NAME/KEY: modified_base
<222> LOCATION: (1405)
<223> OTHER INFORMATION: a, c, g, t, unknown or other
<220> FEATURE:
<221> NAME/KEY: modified_base
<222> LOCATION: (1430)
<223> OTHER INFORMATION: a, c, g, t, unknown or other
<220> FEATURE:
<221> NAME/KEY: modified_base
<222> LOCATION: (1432)
<223> OTHER INFORMATION: a, c, g, t, unknown or other
```

```
<220> FEATURE:
<221> NAME/KEY: modified_base
<222> LOCATION: (1453)
<223> OTHER INFORMATION: a, c, g, t, unknown or other
<220> FEATURE:
<221> NAME/KEY: modified_base
<222> LOCATION: (1484)
<223> OTHER INFORMATION: a, c, g, t, unknown or other
<220> FEATURE:
<221> NAME/KEY: modified_base
<222> LOCATION: (1525)
<223> OTHER INFORMATION: a, c, g, t, unknown or other

<400> SEQUENCE: 56
atgagagaga taatgtttat atattccatc atctgttccg tttggatcct ctcacctctc      60
tctctctctc tctctctggt gccatggaat ccggtagtgc ccgatgttta tattctctct     120
ggttctgaaa tcatcgccga ggaaataaca aatgcagcct ccaaacctcg cgaagcttcc     180
ttcacacact tccttctatt ccttgttcgt cgaacaagct ctttaacatt ccatcaccac     240
aacttcctac ctacaccttc cgatattgca tcttcaactg tttggttaca tttcacacgt     300
aataattatt gtttctttcg attggatcgg tcggaaccat cgctcgaaga aatctccgg      360
agacgtagaa gcaatatcag tttactgtat gtattggttc ggattaataa taataacgaa     420
aaaatagaaa gaaatcaga gttgaaaata gccagaagaa gattaagcgc gatgttggat      480
cttaatctga atgccgagtc gactcagaac aacgagtcgc tggtgctgtt ggacaagttt     540
cccgaagctt cgttgggaac ttcgaattcc tccgtcgtga atgcggaggg atcgagcaac     600
gaggactcgt gctccacacg cgccggcgac gtgttcgcct tcagtttcgg aatccttaag     660
gtggaaggcg cgaacgaagt cgtcgccacg gcgacgaagg agctgtttcc ggtgagctcg     720
gagaattggc aggggcagag ttcgacgtcg tcgtctcagg cgaggaagaa tttaatggat     780
ctcccgctgg atcatcaaaa cggtgaggtg aaggtggttc aggttcagcc acagcctcag     840
gtgaagaaga gtaggagagg tccaaggtct cggagctctc agtacagagg agtcactttc     900
tacagaagga ccggaagatg ggaatcgcat atctgggatt gcgggaagca agtctatttg     960
ggtggatttg acaccgctca tattgctgct agggcctatg atcgaactgc tattaagttc    1020
aggggacttg atgctgatat caattttgat ctcgttgatt atgaggagga tctaaaacag    1080
atgaagaatc tttcaagcag gagttcgtgc acatacttcg ccgccacagt accggttctc    1140
anggcagtt cgaaataccn gggatacact tcacaagtgg ccttgggaac tcgatgggna    1200
ttcctggcag aagctataca ggcacttcag tgcataaana agntgtccta cttnaccatt    1260
nttgnacgna gaacngagct tcatcctgga naggtagcag gcgtttcang caagagnagg    1320
tnccctattg agccagaatn gggaggagag aaccggagtn taagaagng gcntccggcc    1380
tggnctcaat tgggcnagca acccnagaca tgtcccaaag aaaatagggn cnttttcagt    1440
tccagtccat ccnttacaac atgcatccgg gaagaagttc aagnatggag actaatgtta    1500
attcggttat tggtgatcct tcttngaaaa ggctggttgt acgaagagcg tccttctgta    1560
tattccactt tcttttcccaa tctgaaagga gcagagagaa tgggcataga tccttcaaaa    1620
ggagttccaa actgggcgtg gcagacaaat ggccaggtta atgccacccc agtaccaccg    1680
ttctctactg cagcatcatc aggattctca atttcagcta cttttccatc aactgccatc    1740
tttccaacaa aatccatgaa cccaattccc cagagcttct gtttcacttc acacagcaca    1800
ccaggtagca atgcacctca attctattac gaggtcaagt cctcgcaggc accatcccag    1860
cctctatctt gtaatacaag tataaatggt agcccaccac acaagttctg a              1911
```

```
<210> SEQ ID NO 57
<211> LENGTH: 636
<212> TYPE: PRT
<213> ORGANISM: Glycine max
<220> FEATURE:
<221> NAME/KEY: misc_feature
<222> LOCATION: (381)
<223> OTHER INFORMATION: Xaa is any amino acid
<220> FEATURE:
<221> NAME/KEY: misc_feature
<222> LOCATION: (387)
<223> OTHER INFORMATION: Xaa is any amino acid
<220> FEATURE:
<221> NAME/KEY: misc_feature
<222> LOCATION: (400)
<223> OTHER INFORMATION: Xaa is any amino acid
<220> FEATURE:
<221> NAME/KEY: misc_feature
<222> LOCATION: (413)
<223> OTHER INFORMATION: Xaa is any amino acid
<220> FEATURE:
<221> NAME/KEY: misc_feature
<222> LOCATION: (415)
<223> OTHER INFORMATION: Xaa is any amino acid
<220> FEATURE:
<221> NAME/KEY: misc_feature
<222> LOCATION: (418)
<223> OTHER INFORMATION: Xaa is any amino acid
<220> FEATURE:
<221> NAME/KEY: misc_feature
<222> LOCATION: (421)..(422)
<223> OTHER INFORMATION: Xaa is any amino acid
<220> FEATURE:
<221> NAME/KEY: misc_feature
<222> LOCATION: (431)
<223> OTHER INFORMATION: Xaa is any amino acid
<220> FEATURE:
<221> NAME/KEY: misc_feature
<222> LOCATION: (437)
<223> OTHER INFORMATION: Xaa is any amino acid
<220> FEATURE:
<221> NAME/KEY: misc_feature
<222> LOCATION: (439)
<223> OTHER INFORMATION: Xaa is any amino acid
<220> FEATURE:
<221> NAME/KEY: misc_feature
<222> LOCATION: (441)
<223> OTHER INFORMATION: Xaa is any amino acid
<220> FEATURE:
<221> NAME/KEY: misc_feature
<222> LOCATION: (447)
<223> OTHER INFORMATION: Xaa is any amino acid
<220> FEATURE:
<221> NAME/KEY: misc_feature
<222> LOCATION: (454)
<223> OTHER INFORMATION: Xaa is any amino acid
<220> FEATURE:
<221> NAME/KEY: misc_feature
<222> LOCATION: (457)..(458)
<223> OTHER INFORMATION: Xaa is any amino acid
<220> FEATURE:
<221> NAME/KEY: misc_feature
<222> LOCATION: (462)
<223> OTHER INFORMATION: Xaa is any amino acid
<220> FEATURE:
<221> NAME/KEY: misc_feature
<222> LOCATION: (466)
<223> OTHER INFORMATION: Xaa is any amino acid
<220> FEATURE:
<221> NAME/KEY: misc_feature
<222> LOCATION: (469)
<223> OTHER INFORMATION: Xaa is any amino acid
<220> FEATURE:
<221> NAME/KEY: misc_feature
<222> LOCATION: (477)..(478)
<223> OTHER INFORMATION: Xaa is any amino acid
<220> FEATURE:
<221> NAME/KEY: misc_feature
<222> LOCATION: (485)
<223> OTHER INFORMATION: Xaa is any amino acid
```

```
<220> FEATURE:
<221> NAME/KEY: misc_feature
<222> LOCATION: (495)
<223> OTHER INFORMATION: Xaa is any amino acid
<220> FEATURE:
<221> NAME/KEY: misc_feature
<222> LOCATION: (509)
<223> OTHER INFORMATION: Xaa is any amino acid

<400> SEQUENCE: 57
```

Met Arg Glu Ile Met Phe Ile Tyr Ser Ile Ile Cys Ser Val Trp Ile
1               5                   10                  15

Leu Ser Pro Leu Ser Leu Ser Leu Val Pro Trp Asn Pro Val
            20                  25                  30

Val Pro Asp Val Tyr Ile Leu Ser Gly Ser Glu Ile Ala Glu Glu
        35                  40                  45

Ile Thr Asn Ala Ala Ser Lys Pro Arg Glu Ala Ser Phe Thr His Phe
    50                  55                  60

Leu Leu Phe Leu Val Arg Arg Thr Ser Ser Leu Thr Phe His His His
65                  70                  75                  80

Asn Phe Leu Pro Thr Pro Ser Asp Ile Ala Ser Ser Thr Val Trp Leu
                85                  90                  95

His Phe Thr Arg Asn Asn Tyr Cys Phe Phe Arg Leu Asp Arg Ser Glu
            100                 105                 110

Pro Ser Leu Glu Glu Asn Leu Arg Arg Arg Ser Asn Ile Ser Leu
        115                 120                 125

Leu Tyr Val Leu Val Arg Ile Asn Asn Asn Glu Lys Ile Glu Arg
    130                 135                 140

Lys Ser Glu Leu Lys Ile Ala Arg Arg Leu Ser Ala Met Leu Asp
145                 150                 155                 160

Leu Asn Leu Asn Ala Glu Ser Thr Gln Asn Asn Glu Ser Leu Val Leu
                165                 170                 175

Leu Asp Lys Phe Pro Glu Ala Ser Leu Gly Thr Ser Asn Ser Ser Val
            180                 185                 190

Val Asn Ala Glu Gly Ser Ser Asn Glu Asp Ser Cys Ser Thr Arg Ala
        195                 200                 205

Gly Asp Val Phe Ala Phe Ser Phe Gly Ile Leu Lys Val Glu Gly Ala
    210                 215                 220

Asn Glu Val Val Ala Thr Ala Thr Lys Glu Leu Phe Pro Val Ser Ser
225                 230                 235                 240

Glu Asn Trp Gln Gly Gln Ser Ser Thr Ser Ser Ser Gln Ala Arg Lys
                245                 250                 255

Asn Leu Met Asp Leu Pro Leu Asp His Gln Asn Gly Glu Val Lys Val
            260                 265                 270

Val Gln Val Gln Pro Gln Pro Gln Val Lys Lys Ser Arg Arg Gly Pro
        275                 280                 285

Arg Ser Arg Ser Ser Gln Tyr Arg Gly Val Thr Phe Tyr Arg Arg Thr
    290                 295                 300

Gly Arg Trp Glu Ser His Ile Trp Asp Cys Gly Lys Gln Val Tyr Leu
305                 310                 315                 320

Gly Gly Phe Asp Thr Ala His Ile Ala Ala Arg Ala Tyr Asp Arg Thr
                325                 330                 335

Ala Ile Lys Phe Arg Gly Leu Asp Ala Asp Ile Asn Phe Asp Leu Val
            340                 345                 350

Asp Tyr Glu Glu Asp Leu Lys Gln Met Lys Asn Leu Ser Ser Arg Ser
        355                 360                 365

```
Ser Cys Thr Tyr Phe Ala Ala Thr Val Pro Val Leu Xaa Gly Ser Ser
370                 375                 380

Lys Tyr Xaa Gly Tyr Thr Ser Gln Val Ala Leu Gly Thr Arg Trp Xaa
385                 390                 395                 400

Phe Leu Ala Glu Ala Ile Gln Ala Leu Gln Cys Ile Xaa Lys Xaa Ser
            405                 410                 415

Tyr Xaa Thr Ile Xaa Xaa Arg Arg Thr Glu Leu His Pro Gly Xaa Val
        420                 425                 430

Ala Gly Val Ser Xaa Lys Xaa Arg Xaa Pro Ile Glu Pro Glu Xaa Gly
            435                 440                 445

Gly Glu Asn Arg Ser Xaa Lys Lys Xaa Xaa Pro Ala Trp Xaa Gln Leu
450                 455                 460

Gly Xaa Gln Pro Xaa Thr Cys Pro Lys Glu Asn Arg Xaa Xaa Phe Ser
465                 470                 475                 480

Ser Ser Pro Ser Xaa Thr Thr Cys Ile Arg Glu Val Gln Xaa Trp
                485                 490                 495

Arg Leu Met Leu Ile Arg Leu Leu Val Ile Leu Leu Xaa Lys Gly Trp
            500                 505                 510

Leu Tyr Glu Glu Arg Pro Ser Val Tyr Ser Thr Phe Phe Pro Asn Leu
            515                 520                 525

Glu Arg Ala Glu Arg Met Gly Ile Asp Pro Ser Lys Gly Val Pro Asn
530                 535                 540

Trp Ala Trp Gln Thr Asn Gly Gln Val Asn Ala Thr Pro Val Pro Pro
545                 550                 555                 560

Phe Ser Thr Ala Ala Ser Ser Gly Phe Ser Ile Ser Ala Thr Phe Pro
            565                 570                 575

Ser Thr Ala Ile Phe Pro Thr Lys Ser Met Asn Pro Ile Pro Gln Ser
            580                 585                 590

Phe Cys Phe Thr Ser His Ser Thr Pro Gly Ser Asn Ala Pro Gln Phe
            595                 600                 605

Tyr Tyr Glu Val Lys Ser Ser Gln Ala Pro Ser Gln Pro Leu Ser Cys
610                 615                 620

Asn Thr Ser Ile Asn Gly Ser Pro Pro His Lys Phe
625                 630                 635

<210> SEQ ID NO 58
<211> LENGTH: 831
<212> TYPE: DNA
<213> ORGANISM: Pisum sativum

<400> SEQUENCE: 58
cgcaattttt tgtgaagctg agggaggatt ggattttaca cctattcaaa agtcattcaa      60
agtttgtccc tccattcaag gatgaatgta gattttcaa gcatcaaaca caagaatcac     120
tagcataaca tgctttgaaa cccacacact taaattaatg ttaggaatat caaatccaat     180
ataaaatcat agttgtcaat tacatactca atcaagtccc tttctttac ccaataaaca     240 tcaacatatt gcttcttcca ttaagcatat aaacatcaaa gtctaaaact agcaaaatgt     300
tgtttttagg atgacacatt tcatacatag tttaaagat acttgattcg attacaaaaa     360
gaaattacca atagtttagc acaaagtcta agcataatt aaagcatcac atgtgcagat     420
ttatgaaaaa aagattaaga ttgcccccttt catcacgggt cgaataatag cactacttgt     480
cactacatgt taaaaaaatg tcctctagta catcaaactt tttccattga ttccccttat     540
ccatgaaaaa aataaacaaa ttcttaagac acaaaaaaat ggccccacat cctttttct     600 ggcctagttt gtttgaattc attctaactc ttgaatatgt aacgaggccc actaaaaatc     660
```

```
aatcaatgat ttaacataaa aaatgaatag tttaattcca atttgctgca acatggtccg     720
tgaatatgac tcacgagaaa gatatatcaa aatatcaaaa tttcatagtt tttttcacca     780
tataaacctc atcactcatt ctattttttt aagtgcaaag cttcatagtt a              831
```